US007939267B2

(12) United States Patent
Moore et al.

(10) Patent No.: US 7,939,267 B2
(45) Date of Patent: *May 10, 2011

(54) DETECTION OF ACTIVATION OF ENDOTHELIAL CELLS AS SURROGATE MARKER FOR ANGIOGENESIS

(75) Inventors: Sean C. Moore, Durham, NC (US); Sharat Singh, Los Altos, CA (US); Hossein Salimi-Moosavi, Sunnyvale, CA (US); Liching Cao, Vallejo, CA (US); Jeff Sperinde, El Granada, CA (US)

(73) Assignee: Laboratory Corporation of America Holdings, Burlington, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 11/267,870

(22) Filed: Nov. 3, 2005

(65) Prior Publication Data

US 2006/0199231 A1 Sep. 7, 2006

Related U.S. Application Data

(60) Provisional application No. 60/625,694, filed on Nov. 4, 2004.

(51) Int. Cl.
*G01N 33/53* (2006.01)
*G01N 33/566* (2006.01)
*G01N 33/58* (2006.01)
*G01N 33/567* (2006.01)
*G01N 33/535* (2006.01)

(52) U.S. Cl. .......... 435/7.1; 435/7.2; 436/535; 436/544; 436/546; 436/824; 530/402; 530/412

(58) Field of Classification Search .......................... None
See application file for complete search history.

(56) References Cited

U.S. PATENT DOCUMENTS

| | | | |
|---|---|---|---|
| 4,230,558 A | 10/1980 | Fulwyler | |
| 4,318,846 A | 3/1982 | Khanna et al. | |
| 4,375,407 A | 3/1983 | Kronick | |
| 4,452,773 A | 6/1984 | Molday | |
| 4,650,750 A | 3/1987 | Giese | |
| 4,795,698 A | 1/1989 | Owen et al. | |
| 4,811,218 A | 3/1989 | Hunkapiller et al. | |
| 4,943,533 A | 7/1990 | Mendelsohn et al. | |
| 4,997,928 A | 3/1991 | Hobbs, Jr. | |
| 5,096,815 A | 3/1992 | Ladner et al. | |
| 5,183,884 A | 2/1993 | Kraus et al. | |
| 5,194,596 A * | 3/1993 | Tischer et al. ................ 530/399 |
| 5,233,409 A | 8/1993 | Schwab | |
| 5,340,716 A | 8/1994 | Ullman et al. | |
| 5,360,819 A | 11/1994 | Giese | |
| 5,403,484 A | 4/1995 | Ladner et al. | |
| 5,480,968 A | 1/1996 | Kraus et al. | |
| 5,508,164 A | 4/1996 | Kausch et al. | |
| 5,516,636 A | 5/1996 | McCapra | |
| 5,516,931 A | 5/1996 | Giese et al. | |
| 5,536,834 A | 7/1996 | Singh et al. | |
| 5,565,324 A | 10/1996 | Still et al. | |
| 5,565,552 A | 10/1996 | Magda et al. | |
| 5,597,531 A | 1/1997 | Liberti et al. | |
| 5,599,681 A | 2/1997 | Epstein et al. | |
| 5,602,273 A | 2/1997 | Giese et al. | |
| 5,622,929 A | 4/1997 | Willner et al. | |
| 5,646,001 A | 7/1997 | Terstappen et al. | |
| 5,665,582 A | 9/1997 | Kausch et al. | |
| 5,677,171 A | 10/1997 | Hudziak et al. | |
| 5,691,208 A | 11/1997 | Miltenyi et al. | |
| 5,698,271 A | 12/1997 | Liberti et al. | |
| 5,709,994 A | 1/1998 | Pease et al. | |
| 5,763,602 A | 6/1998 | Li et al. | |
| 5,772,997 A | 6/1998 | Hudziak et al. | |
| 5,811,098 A | 9/1998 | Plowman et al. | |
| 5,945,526 A | 8/1999 | Lee et al. | |
| 5,968,511 A | 10/1999 | Akita et al. | |
| 5,986,076 A | 11/1999 | Rothschild et al. | |
| 5,998,224 A | 12/1999 | Rohr et al. | |
| 6,001,673 A | 12/1999 | Marcinkiewicz | |
| 6,048,515 A | 4/2000 | Kresse et al. | |
| 6,096,723 A | 8/2000 | Menchen et al. | |
| 6,191,278 B1 | 2/2001 | Lee et al. | |

(Continued)

FOREIGN PATENT DOCUMENTS

EP 0484027 10/1991

(Continued)

OTHER PUBLICATIONS

Cao et al, J Biol chem. 271(6): 3154, Feb. 1996.*
Monestiroli et al, Cancer Research 61: 4341-4344, Jun. 1, 2001.*
Butthep et al, American J Hematology 70: 100-106, 2002.*
Peichev et al, Blood 95(3): 952-958, Feb. 2000.*
Chan et al, J Surgical Research 111: 120-126, 2003.*
Benjamin et al, Development 125:1591-1598, 1998.*
Autiero et al, Nature Medicine 9(7): 936-943, Jul. 2003.*
Avraham, H. K. et al., "Vascular Endothelial Growth Factor Regulates Focal Adhesion Assembly in Human Brain Microvascular Endothelial Cells Through Activation of the Focal Adhesion Kinase and Related Adhesion Focal Tyrosine Kinase," The Journal of Biological Chemistry, Sep. 19, 2003, pp. 36661-36668, vol. 278, No. 38.
Blagoev, B. et al., "A Proteomics Strategy to Elucidate Functional Protein-Protein Interactions Applied to EGF Signaling," Nature Biotechnology, Mar. 2003, pp. 315-318, vol. 21.

(Continued)

*Primary Examiner* — Phuong Huynh
(74) *Attorney, Agent, or Firm* — Kilpatrick Townsend & Stockton LLP

(57) ABSTRACT

Methods, compositions and kits are provided for assessing angiogenesis through sensitive, direct detection of activation of endothelial cells at molecular levels. In general, activation of endothelial cells is detected by measuring the levels of cellular components and their protein complexes participating in a specific angiogenesis signaling pathway in endothelial cells. The methods can be used for assessing status of diseases associated with undesirable angiogenesis, such as the likelihood of developing the disease, presence or absence of the disease, prognosis of the disease and the likelihood of response or resistance to a particular anti-angiogenic therapy. The methods can also be used to guide the design of effective therapeutic regimens targeting a specific angiogenic signaling pathway, as well as in conjunction with therapeutic intervention of diseases or conditions associated with undesirable angiogenesis.

19 Claims, 26 Drawing Sheets

U.S. PATENT DOCUMENTS

| | | | |
|---|---|---|---|
| 6,251,581 B1 | 6/2001 | Ullman et al. | |
| 6,261,535 B1 * | 7/2001 | Thorpe et al. | 424/1.49 |
| 6,346,384 B1 | 2/2002 | Pollner | |
| 6,365,362 B1 | 4/2002 | Terstappen et al. | |
| 6,372,907 B1 | 4/2002 | Lee et al. | |
| 6,488,390 B1 | 12/2002 | Lebens et al. | |
| 6,627,400 B1 * | 9/2003 | Singh et al. | 506/4 |
| 6,949,347 B2 * | 9/2005 | Singh et al. | 435/7.1 |
| 7,105,308 B2 * | 9/2006 | Chan-Hui et al. | 435/7.2 |
| 7,402,397 B2 * | 7/2008 | Chan-Hui et al. | 435/7.1 |
| 2002/0013126 A1 | 1/2002 | Raso | |
| 2002/0146726 A1 | 10/2002 | Matray et al. | |
| 2003/0170734 A1 | 9/2003 | Williams et al. | |
| 2003/0170915 A1 | 9/2003 | Singh et al. | |
| 2003/0235832 A1 | 12/2003 | Chenna et al. | |
| 2004/0126818 A1 * | 7/2004 | Chan-Hui et al. | 435/7.2 |
| 2004/0229293 A1 | 11/2004 | Chan Hui et al. | |

FOREIGN PATENT DOCUMENTS

| | | |
|---|---|---|
| EP | 0510688 | 4/1992 |
| EP | 0599274 | 11/1993 |
| WO | WO 96/40210 | 12/1996 |
| WO | WO 99/19488 | 4/1999 |
| WO | WO 01/84157 | 11/2001 |
| WO | WO 03/051669 | 6/2003 |
| WO | WO 2004/011900 | 2/2004 |

OTHER PUBLICATIONS

George, F. et al., "Rapid Isolation of Human Endothelial Cells from Whole Blood Using S-Endo1 Monoclonal Antibody Coupled to Immuno-Magnetic Beads: Demonstration of Endothelial Injury After Angioplasty," Thromb. Haemost., Jan. 1992, pp. 147-153, vol. 67, No. 1.

Sklar, L.A. et al., "Flow Cytometric Analysis of Ligand-Receptor Interactions and Molecular Assemblies," Annu. Rev. Biophys. Biomol. Struct., 2002, pp. 97-119, vol. 31.

Banks, R. et .al., "Circulating intercellular adhesion molecule-1 (ICAM-1), E-selectin and vascular cell adhesion molecule-1 (VCAM-1) in human malignancies," Br. J. Cancer, 1993, 68(1):122-4.

Beerepoot, L.V. et al., "Increased levels of viable circulating endothelial cells are an indicator of progressive disease in cancer patients," Annals of Oncology, 2004, 15:139-145.

Marron, M.B. et al., "Evidence for heterotypic interaction between the receptor tyrosine kinases TIE-1 and TIE-2," J. Biol. Chem., 2000, 275(50):39741-6.

Cheng, N. et al., "Blockade of EphA receptor tyrosine kinase activation inhibits vascular endothelial cell growth factor-induced angiogenesis," Mol. Cancer Res., 2002, No. 1(1):2-11.

Chou, M.T. et al., "Src Kinase becomes preferentially associated with the VEGFR, KDR/Flk-I, following VEGF stimulation of vascular endothelial cells," BMC Biochemistry, 2002, 3:32-43.

Chu, C. et al., "Receptor dimerization is not a factor in the signalling activity of a transforming variant epidermal growth factor receptor (EGFRvIII)," Biochem. J., 1997, 324 ( Pt 3):855-61.

Ciardiello, F. et al., "Inhibition of growth factor production and angiogenesis in human cancer cells by ZD1839 (Iressa), a selective epidermal growth factor receptor tyrosine kinase inhibitor," Clin. Cancer Res., 2001, 7(5):1459-65.

Colorado, P. et al., "Anti-angiogenic cues from vascular basement membrane collagen," Cancer Res., 2000, 60(9):2520-6.

Cuatrecasas, P., "Protein purification by affinity chromatography. Derivatizations of agarose and polyacrylamide beads," J. Biol. Chem., 1970, 245(12):3059-65.

D'Amato, T. et al., "Thalidomide is an inhibitor of angiogenesis," Proc. Natl. Acad. Sci. USA, 1994, 91(9):4082-5.

Davis, D. et al., "Surrogate markers in antiangiogenesis clinical trials," Br. J. Cancer, 2003, 89(1):8-14.

Dirix, L. et al., "Elevated levels of the angiogenic cytokines basic fibroblast growth factor and vascular endothelial growth factor in sera of cancer patients," Br. J. Cancer., 1997, 76(2):283-243.

Dixelius, J. et al., "Endostatin-induced tyrosine kinase signaling through the Shb adaptor protein regulates endothelial cell apoptosis," Blood, 2000, 95(11):3403-11.

Dumont, D. et al., "Vascularization of the mouse embryo: A study of flk-1, tek, tie, and vascular endothelial growth factor expression during development," Dev Dyn 203 (1) : 80-92, May 1995.

Erber, R. et al., "Combined inhibition of VEGF and PDGF signaling enforces tumor vessel regression by interfering with pericyte-mediated endothelial cell survival mechanisms," FASEB J., 2004, 18(2):338-340.

Fendly, B. et al., "Characterization of murine monoclonal antibodies reactive to either the human epidermal growth factor receptor or HER2/neu gene product," Cancer Res., 1990, 50(5):1550-8.

Ferrara, N., "Role of vascular endothelial growth factor in the regulation of angiogenesis," Kidney International, 1999, 56, 794-814.

Ferrara, N., "Vascular endothelial growth factor: basic science and clinical progress," Endocr. Rev., 2004, 25(4):581-611.

Folkman, J. et al., "Angiogenesis," J. Biol. Chem., 1992, 267:10931-10934.

Folkman, J., "How is blood vessel growth regulated in normal and neoplastic tissue? G.H.A. Clowes memorial Award lecture," Cancer Res., 1986, 46(2):467-73.

Folkman, J., "What is the evidence that tumors are angiogenesis dependent?" J. Natl. Cancer Inst., 1990, 82(1):4-6.

Fukumura, D. et al., "Tumor induction of VEGF promoter activity in stromal cells," Cell, Sep. 1998, 94(6):715-725.

Gadella Jr, T. and Jovin, T., "Oligomerization of epidermal growth factor receptors on A431 cells studied by time-resolved fluorescence imaging microscopy. A stereochemical model for tyrosine kinase receptor activation," J. Cell Biol., 1995, 129(6):1543-58.

Gale, N. et al., "Growth factors acting via endothelial cell-specific receptor tyrosine kinases: VEGFs, angiopoietins, and ephrins in vascular development," Genes Dev., 1999, 13(9):1055-66.

Gitay-Goren, H. et al., "The binding of vascular endothelial growth factor to its receptors is dependent on cell surface-associated heparin-like molecules," J. Biol. Chem., 1992, 267(9):6093-8.

Goligorsky, M. et al., "Workshop: endothelial cell dysfunction leading to diabetic nephropathy: focus on nitric oxide," Hypertension, 2001, 37(2):744-748.

Gutheil, J. et al., "Targeted antiangiogenic therapy for cancer using Vitaxin: a humanized monoclonal antibody to the integrin $a_v\beta_3$," Clin. Cancer Res., 2000, 6:3056-3061.

Hanahan, D. and Folkman, J., "Patterns and emerging mechanisms of the angiogenic switch during tumorigenesis," Cell, 1996, 86(3):353-64.

Bergers, G. et al., "Benefits of targeting both pericytes and endothelial cells in the tumor vasculature with kinase inhibitors," J. Clin. Invest., 2003, 111(9):1287-95.

Heldin, C. and Westermark, B., "Mechanism of action and in vivo role of platelet-derived growth factor," Physiol. Rev., 1999, 79(4):1283-316.

Humphrey, P. et al., "Anti-synthetic peptide antibody reacting at the fusion junction of deletion-mutant epidermal growth factor receptors in human glioblastoma," Proc. Natl. Acad. Sci. USA, 1990, 87(11):4207-11.

Hunter, I. et al., "Evidence for regulated dimerization of cell—cell adhesion molecule (C-CAM) in epithelial cells," Biochem. J., 1996, 320:847-53.

Willett, C.G. et al., "Direct evidence that the VEGF-specific antibody bevacizumab has antivascular effects in human rectal cancer," Nat. Med., 2004, 10(2):145-147.

Jouan, V. et al., "Inhibition of in vitro angiogenesis by platelet factor-4-derived peptides and mechanism of action," Blood, 1999, 94(3):984-93.

Kamphaus, G. et al., "Canstatin, a Novel Matrix-derived Inhibotor of Angiogenesis and Tumor Growth," J. Biol. Chem., 2000, 275:1209-1215.

Kanofsky, J., "Singlet oxygen production by lactoperoxidase," J. Biol. Chem., 1983, 258(10):5991-3.

Kanthou, C. and Tozer, G.M., "The tumor vascular targeting agent combretastatin A-4-phosphate induces reorganization of the actin cytoskeleton and early membrane blebbing in human endothelial cells," Blood, 2002, 99(6):2060-9.

Kerbel, R. et al., "Establishing a link between oncogenes and tumor angiogenesis," Mol. Med., 1998, 4(5):286-95.

Kraus, M. et al., "Isolation and characterization of ERBB3, a third member of the ERBB/epidermal growth factor receptor family: evidence for overexpression in a subset of human mammary tumors," Proc. Natl. Acad. Sci. USA, 1989, 86(23):9193-7.

Lee, L. et al., "New energy transfer dyes for DNA sequencing," Nucleic Acids Res., 1997, 25(14):2816-22.

Levitt, N. et al., "Phase I and pharmacological study of the oral matrix metalloproteinase inhibitor, MMI270 (CGS27023A), in patients with advanced solid cancer," Clin. Cancer Res., 2001, 7(7):1912-22.

Maeshima, Y. et al., "Identification of the anti-angiogenic site within vascular basement membrane-derived tumstatin," J. Biol. Chem., 276(18):15240-8. Epub Feb. 7, 2001.

Mancuso, P. et al., Resting and activated endothelial cells are increased in the peripheral blood of cancer patients,' Blood, 2001, 97(11):3658-61.

Matthews, W. et al., "A receptor tyrosine kinase cDNA isolated from a population of enriched primitive hematopoietic cells and exhibiting close genetic linkage to c-kit," Proc. Natl. Acad. Sci. USA, 1991, 88(20): 9026-9030.

Miao, H, et al., "Neuropilin-1 expression by tumor cells promotes tumor angiogenesis and progression," FASEB J., 2000, 14(15):2532-9.

Monestiroli, S. et al., "Kinetics and viability of circulating endothelial cells as surrogate angiogenesis marker in an animal model of human lymphoma," Cancer Res., 2001, 61(11):4341-4.

Morgan, B. et al., "Dynamic contrast-enhanced magnetic resonance imaging as a biomarker for the pharmacological response of PTK787/ZK 222584, an inhibitor of the vascular endothelial growth factor receptor tyrosine kinases, in patients with advanced colorectal cancer and liver metastases: results from two phase I studies," J. Clin. Oncol., 2003, 21(21):3955-64.

Mustonen, T. et al., "Endothelial receptor tyrosine kinases involved in angiogenesis," J. Cell. Biol., 1995, 129(4):895-8.

Nicosia, R., "What is the role of vascular endothelial growth factor-related molecules in tumor angiogenesis?" Am. J. Pathol., 1998, 153(1):11-6.

Ogawa, K. et al., "The ephrin-A1 ligand and its receptor, EphA2, are expressed during tumor neovascularization," Oncogene, 2000, 19(52):6043-52.

Saucier, C. et al., "The Shc adaptor protein is critical for VEGF induction by Met/HGF and ErbB2 receptors and for early onset of tumor angiogenesis," Proc. Natl. Acad. Sci. USA, 2004, 101(8):2345-50.

Pietras, K. et al., "Inhibition of platelet-derived growth factor receptors reduces interstitial hypertension and increases transcapillary transport in tumors," Cancer Res., 2001, 61: 2929-2934.

Plowman, G. et al., "Ligand-specific activation of HER4/p180erbB4, a fourth member of the epidermal growth factor receptor family," Proc. Natl. Acad. Sci. USA, 1993, 90(5):1746-50.

Polakowski, I. et al., "A ribonuclease inhibitor expresses anti-angiogenic properties and leads to reduced tumor growth in mice," Am. J. Pathol., 1993, 143(2):507-17.

Racila, E. et al., Detection and characterization of carcinoma cells in the blood, Proc Natl. Acad. Sci. USA, 1998, 95(8):4589-94.

Dayanir, V. et al., "Identification of tyrosine residues in vascular endothelial growth factor receptor-2/FLK-1 involved in activation of phosphatidylinositol 3-kinase and cell proliferation," J. Biol. Chem., 2001, 276(21):17686-92.

Relf, M. et al., "Expression of the angiogenic factors vascular endothelial cell growth factor, acidic and basic fibroblast growth factor, tumor growth factor beta-1, platelet-derived endothelial cell growth factor, placenta growth factor, and pleiotrophin in human primary breast cancer and its relation to angiogenesis," Cancer Res., 1997, 57(5):963-9.

Venkataraman, G. et al., "A stereochemical approach to pyranose ring flexibility: its implications for the conformation of dermatan sulfate," Proc. Natl. Acad. Sci. USA, 1994, 91(13):6171-5.

Semba, K. et al., "A v-erbB-related protooncogene, c-erbB-2, is distinct from the c-erbB-1/epidermal growth factor-receptor gene and is amplified in a human salivary gland adenocarcinoma," Proc. Natl. Acad. Sci. USA, 1985, 82(19):6497-6501.

Shi, Q. et al., "Evidence for circulating bone marrow-derived endothelial cells," Blood, 1998, 92(2):362-367.

Shibuya, M., "Structure and function of VEGF/VEGF-receptor system involved in angiogenesis," Cell Struct. Funct., 2001, 26(1):25-35.

Singh, R. et al., "Interferons alpha and beta down-regulate the expression of basic fibroblast growth factor in human carcinomas," Proc. Nat. Acad. Sci. USA, 1995, 92(10):4562-6.

Soker, S. et al., "Characterization of novel vascular endothelial growth factor (VEGF) receptors on tumor cells that bind VEGF165 via its exon 7-encoded domain," J. Biol. Chem., 1996, 271(10):5761-7.

Steele-Perkins, G. et al., "Expression and characterization of a functional human insulin-like growth factor I receptor," J. Biol. Chem., 1988, 263(23):11486-92.

Talks, K. and Harris, A., "Current status of antiangiogenic factors," Br. J. Haematol., 2000, 109(3):477-89.

Tallquist, M. et al., "Growth factor signaling pathways in vascular development," Oncogene, 1999, 18(55):7917-32.

Tille, J.-C. et al., "Vascular endothelial growth factor (VEGF) receptor-2 antagonists inhibit VEGF—and basic fibroblast growth factor-induced angiogenesis in vivo and in vitro," J. Pharmacol. Exp. Ther., 2001, 299(3):1073-85.

Troyanovsky, B. et al., "Angiomotin: an angiostatin binding protein that regulates endothelial cell migration and tube formation," J. Cell Biol., 2001, 152(6):1247-54.

Ullman, E. et al., "Luminescent oxygen channeling immunoassay: measurement of particle binding kinetics by chemiluminescence," Proc. Natl. Acad. Sci. USA, 1994, 91(12):5426-30.

Ullrich, A. et al., "Insulin-like growth factor I receptor primary structure: comparison with insulin receptor suggests structural determinants that define functional specificity," EMBO J., 1986, 5(10):2503-12.

Valenzuela, D. et al., "Angiopoietins 3 and 4: diverging gene counterparts in mice and humans," Proc. Natl. Acad. Sci. USA, 1999, 96(5):1904-9.

Vapaatalo, H. et al., "Clinically important factors influencing endothelial function," Med. Sci. Monit. 2001, 7(5):1075-85.

Xia, W. et al., "Truncated ErbB2 receptor (p95ErbB2) is regulated by heregulin through heterodimer formation with ErbB3 yet remains sensitive to the dual EGFR/ErbB2 kinase inhibitor GW572016," Oncogene, 2004, 23(3):646-53.

Yahata, Y. et al., "Nuclear translocation of phosphorylated STAT3 is essential for vascular endothelial growth factor-induced human dermal microvascular endothelial cell migration and tube formation," J. Biol. Chem., 2003, 278(41):40026-31.

Zachary, I., "VEGF signalling: integration and multi-tasking in endothelial cell biology," Biochem. Soc. Trans., 2003, 31(Pt 6):1171-7.

Author Unknown, "Bevacizumab. Anti-VEGF Monoclonal Antibody, Avastin, Rhumab-VEGF," 2002, Drugs R&D, 3:28-30.

Bergers, G. and Benjamin, L., "Tumorigenesis and the Angiogenic Switch," 2003, Nat. Rev. Cancer, 3:401-10.

Beutner, S. et al., "Synthetic Singlet Oxygen Quenchers," 2000, Methods Enzymol., 319:226-41.

Blume-Jensen, P. and Hunter, T., "Oncogenic kinase signaling," 2001, Nature, 411:355-365.

Boehm, T. et al., "Antiangiogenic therapy of experimental cancer does not induce acquired drug resistance," 1997, Nature, 390:404-407.

Carmeliet, P. et al., "Role of HIF-1 α in hypoxia-mediated apoptosis, cell proliferation and tumour angiogenesis," 1998, Nature, 394:485-490.

Carpenter, G., "Receptors for Epidermal Growth Factor and Other Polypeptide Mitogens," 1987, Annu. Rev. Biochem., 56:881-914.

Chen, H. et al., "VEGF, VEGFRs expressions and activated STATs in ovarian epithelial carcinoma," 2004, Gynecol. Oncol., 94:630-635.

Corti, R. et al., "Endothelial Dysfunction and Hypertension," 2000, Vascular Endothelium in Human Physiology and Pathophysiology, Valiance, P. and Webb, D., eds., pp. 109-128.

Cross, M. et al., "FGF and VEGF function in angiogenesis: signalling pathways, biological responses and therapeutic inhibition," 2001, Trends Pharmacol. Sci., 22:201-207.

Dameron, K. et al., "Control of Angiogenesis in Fibroblasts by p53 Regulation of Thrombospondin-1," 1994, Science, 265:1582-1584.

Davis, S. et al., "Isolation of Angiopoietin-1, a Ligand for the TIE2 Receptor, by Secretion-Trap Expression Cloning," 1986, Cell, 87:1161-1169.

De Vries, C. et al., "The *fms*-Like Tyrosine Kinase, a Receptor for Vascular Endothelial Growth Factor," 1992, Science, 255:989-991.

DiGabriele, A. et al., "Structure of a heparin-linked biologically active dimer of fibroblast growth factor," 1998, Nature, 393:812-817.

Di Mascio, P. et al.,"Singlet molecular oxygen production in the reaction of peroxynitrite with hydrogen peroxide," 1994, FEBS Lett., 355:287-289.

Eatock, M. et al., "A Phase 1 Study of the Matrix Metalloproteinase Inhibitor MMI270 (Previously Termed CGS27023A) with 5FU and Folinic Acid," 1999, American Soc. Clinical Oncology, 18:209a.

Ferrara, N, et al., "The biology of VEGF and its receptors," 2003, Nat. Med., 9:669-676.

Ferrara, N. and Alitalo, K., "Clinical applications of angiogenic growth factors and their inhibitors," 1999, Nat. Med., 5:1359-1364.

Folkman, J., "Tumor Angiogenesis," 1995, The Molecular Basis of Cancer, Chapter 10, Mendelsohn, J. et al., eds, pp. 206-232, W.B. Saunders Company.

Folkman, J. and Klagsbrun, M., "Angiogenic Factors," 1987, Science, 235:442-447.

Fotsis, T. et al., "The endogenous oestrogen metabolite 2-methoxyoestradiol inhibits angiogenesis and suppresses tumour growth," 1994, Nature, 368:237-239.

Gadducci, A. et al., "Pretreatment Plasma Levels of Fibrinopeptide-A (FPA), D-Dimer (DD), and von Willebrand Factor (vWF) in Patients with Ovarian Carcinoma," 1994, Gynecol. Oncol., 53:352-356.

Ghossein, R. et al., "Molecular Detection and Characterization of Circulating Tumor Cells and Micrometastases in Prostatic, Urothelial, and Renal Cell Carcinomas," 2001, Semin. Surg. Oncol., 20:304-311.

Giese, R.W., "Electrophoric release tags: ultrasensitive molecular labels providing multiplicity," 1983, Trends Anal. Chem., 2:166-168.

Haber, P. et al., "Computer Simulation for the Simultaneous Optimization of Any Two Variables and Any Chromatographic Procedure," 2000, J. Chromatogr. Sci., 38:386-392.

Haller, H., "Endothelial Function—General Considerations," 1997, Drugs, 53(Suppl 1):1-10.

Hoekman, K., "SU6668, a Multitargeted Angiogenesis Inhibitor," 2001, Cancer J., 7(Suppl. 3):134-138.

Holmqvist, K. et al., "The Adaptor Protein Shb Binds to Tyrosine 1175 in Vascular Endothelial Growth Factor (VEGF) Receptor-2 and Regulates VEGF-dependent Cellular Migration," 2004, J. Biol. Chem., 21:22267-22275.

Izumi, Y. et al., "Tumour biology: Herceptin acts as an anti-angiogenic cocktail," 2002, Nature, 416:279-280.

Kaban, K. and Herbst, R., "Angiogenesis as a target for cancer therapy," 2002, Hematol. Onc. Clin. N. Amer., 16:1125-1171.

Kandel, E. and Hay, N., "The Regulation and Activities of the Multifunctional Serine/Threonine Kinase Akt/PKB," 1999. Exp. Cell. Res., 253:210-229.

Kerbel, R and Folkman, J., "Clinical Translation of Angiogenesis Inhibitors," 2002, Nat. Rev. Cancer, 2:727-739.

Kerbel, R., "Inhibition of Tumor Angiogenesis as a Strategy to Circumvent Acquired Resistance to Anti-Cancer Therapeutic Agents," 1991, BioEssays, 13:31-36.

Kim, I. et al., "Molecular cloning and characterization of a novel angiopoietin family protein, angiopoietin-3," 1999, FEBS Lett., 443:353-356.

Lewis, J. et al., "Computer simulation for the prediction of separation as a function of pH for reversed-phase high-performance liquid chromatography. I. Accuracy of a theory-based model," 1992, J. Chromatogr., 592:183-195.

Lewis, J. et al., "Computer simulation for the prediction of separation as a function of pH for reversed-phase high-performance liquid chromatography. II. Resolution as a function of simultaneous change in pH and solvent strength," 1992, J. Chromatogr., 592:197-208.

Lowes, V. et al., "Integration of Signals from Receptor Tyrosine Kinases and G Protein-Coupled Receptors," 2002, Neurosignals, 11:5-19.

Maeshima, Y. et al., "Tumstatin, an Endothelial Cell-Specific Inhibitor of Protein Synthesis," 2002, Science, 295:140-143.

Maisonpierre, P. et al., "Angiopoietin-2, a Natural Antagonist for Tie2 That Disrupts in vivo Angiogenesis," 1997, Science, 277:55-60.

Martin J. and Burch, P., "Production of Oxygen Radicals by Photosensitization," 1990, Methods Enzymol., 186:635-645.

Mezquita, J. et al., "Characterization of a Novel Form of Angiopoietin-2 (Ang-2B) and Expression of VEGF and Angiopoietin-2 During Chicken Testicular Development and Regression," 1999, Biochem. Biophys. Res. Commun., 260:492-498.

Miltenyi, S. et al., "High Gradient Magnetic Cell Separation with MACS," 1990, Cytometry, 11:231-238.

Mitsiades, C. et al., "The Akt Pathway: Molecular Targets for Anti-Cancer Drug Development," 2004, Curr. Cancer Drug Targets., 4:235-256.

Moreno, J. et al., "Changes in Circulating Carcinoma Cells in Patients with Metastatic Prostate Cancer Correlate with Disease Status," 2001, Urology, 58:386-392.

Naicker, S. and Bhoola, K., "Endothelins: vasoactive modulators of renal function in health and disease," 2001, Pharmacol. Ther., 90:61-88.

Nakamura, M. et al., "Separation of a Breast Cancer Cell Line from Human Blood Using a Quadrupole Magnetic Flow Sorter," 2001, Biotechnol. Prog., 17:1145-1155.

Needleman, S. and Wunsch, C., "A General Method Applicable to the Search for Similarities in the Amino Acid Sequence of Two Proteins," 1970, J. Mol. Biol., 48:443-453.

Neuchrist, C. et al., "Vascular Endothelial Growth Factor Receptor 2 (VEGFR2) Expression in Squamous Cell Carcinomas of the Head and Seck," 2001, Laryngoscope, 111:1834-1841.

Nicholson, K and Anderson, N., "The protein kinase B/Akt signalling pathway in human malignancy," 2002, Cell. Signal., 14:381-395.

Oh, P. et al., "Subtractive proteomic mapping of the endothelial surface in lung and solid tumours for tissue-specific therapy," 2004, Nature, 429:629-635.

O'Reilly, M. et al., "Angiostatin: A Novel Angiogenesis Inhibitor That Mediates the Suppression of Metastases by a Lewis Lung Carcinoma," 1994, Cell, 79:315-328.

O'Reilly, M. et al., "Endostatin: An Endogenous Inhibitor of Angiogenesis and Tumor Growth," 1997, Cell, 88:277-285.

Outinen, K. et al., "Optimization of selectivity in high-performance liquid chromatography using desirability functions and mixture designs according to PRISMA," 1998, Eur. J. Pharm. Sci., 6:197-205.

Pelicci, G. et al., "A Novel Transforming Protein (SHC) with an SH2 Domain is Implicated in Mitogenic Signal Transduction," 1992, Cell, 70:93-104.

Pierlot, C. et al., "Naphthalene Endoperoxides as Generators of Singlet Oxygen in Biological Media," 2000, Methods Enzymol., 319:3-20.

Plowman, G. et al., "Heregulin induces tyrosine phosphorylation of HER4/p180$^{erbB4}$," 1993, Nature, 366:473-475.

Radbruch, A. et al., "High-Gradient Magnetic Cell Sorting," 1994, Methods in Cell Biology, vol. 42, Chapter 23, Darzynkiewicz, Z. et al., eds., Academic Press, New York.

Rak, J. et al., "Oncogenes and Angiogenesis: Signaling Three-Dimensional Tumor Growth," 2000, J. Investig. Dermatol. Symp. Proc., 5:24-33.

Reimer, C. et al., "Antineoplastic Effects of Chemotherapeutic Agents are Potentiated by NM-3, an Inhibitor of Angiogenesis," 2002, Cancer Res., 62:789-795.

Safarik, I. and Safarikova, M., "Use of magnetic techniques for the isolation of cells," 1999, J. Chromatogr. B., 722(1-2):33-53.

Schaap, A. et al., "Polymer-Based Sensitizers for Photooxidations II," 1975, J. Am. Chem. Soc., 97:3741-3745.

Schlessinger, J., "Cell Signaling by Receptor Tyrosine Kinases," 2000, Cell, 103:211-225.

Selvin, P., "The renaissance of fluorescence resonance energy transfer," 2000, Nat. Struct. Biol., 7:730-734.

Sessler, J. et al., "Optical Methods for Tumor Treatment and Early Diagnosis: Mechanisms and Techniques," 1991, SPIE, 1426:318-329.

Shibuya, M. et al., "Nucleotide sequence and expression of a novel human receptor-type tyrosine kinase gene (*flt*) closely related to the *fms* family," 1990, Oncogene, 5:519-524.

Smith, T. and Waterman, M., "Comparison of Biosequences," 1981, Advances in Applied Mathematics, 2:482-489.

Smith, C., "Endothelial adhesion molecules and their role in inflammation," 1993, Can. J. Physiol. Pharmacol., 71:76-87.

Soker, S. et al., "Neuropilin-1 is Expressed by Endothelial and Tumor Cells as an Isoform-Specific Receptor for Vascular Endothelial Growth Factor," 1998, Cell, 92:735-745.

Spivak-Kroizman, T. et al., "Heparin-Induced Oligomerization of FGF Molecules is Responsible for FGF Receptor Dimerization, Activation, and Cell Proliferation," 1994, Cell, 79:1015-1024.

St. Croix, B. et al., "Genes Expressed in Human Tumor Endothelium," 2000, Science, 289:1197-1202.

Strong, L. et al., "Antibody-targeted Photolysis. Photophysical, Biochemical, and Pharmacokinetic Properties of Antibacterial Conjugates," 1994, Ann. N.Y. Acad. Sci., 745:297-320.

Taylor, S. and Folkman, J., "Protamine is an inhibitor of angiogenesis," 1982, Nature, 297:307-312.

Teischer, B. et al., "Potentiation of Cytotoxic Cancer Therapies by TNP-470 Alone and With Other Anti-Angiogenic Agents," 1994, Int. J. Cancer, 57:920-925.

Terman, B. et al., "Identification of a new endothelial cell growth factor receptor tyrosine kinase," 1991, Oncogene, 6:1677-1683.

Terman, B. et al., "Identification of the KDR Tyrosine Kinase as a Receptor for Vascular Endothelial Cell Growth Factor," 1992, Biochem. Biophys. Res. Commun., 187:1579-1586.

Weidner, N. et al., "Tumor Angiogenesis and Metastasis—Correlation in Invasive Breast Carcinoma," 1991, N. Engl. J. Med., 324:1-8.

Wheeless, L. et al., "Optics, Light Sources, Filters, and Optical Systems," 1985, Flow Cytometry: Instrumentation and Data Analysis, pp. 21-76, Academic Press, New York.

Wold, F., "Posttranslation Protein Modification: Perspectives and Prospectives," 1983, Posttranslational Covalent Modification for Proteins, Johnson, B.C., ed., pp. 1-12, Academic Press, New York.

Xu, Y. et al., "Endothelial and Macrophage Upregulation of Urokinase Receptor Expression in Human Renal Cell Carcinoma," 1997, Hum. Pathol., 28:206-213.

Yamamoto, T. et al., "Similarity of protein encoded by the human c-erb-B-2 gene to epidermal growth factor receptor," 1986, Nature, 319:230-234.

Yancopoulos, G. et al., "Vascular-specific growth factors and blood vessel formation," 2000, Nature, 407:242-248.

Yarmush, M. et al., "Antibody Targeted Photolysis," 1993, Crit. Rev. Ther. Drug Carrier Syst., 10:197-252.

Zhang, X. et al., "Synthesis of Releasable Electrophore Tags for Applications in Mass Spectrometry," 2002, Bioconjug. Chem., 13:1002-1012.

Zigeuner, R. et al., "Isolation of Circulating Cancer Cells From Whole Blood by Immunomagnetic Cell Enrichment and Unenriched Immunocytochemistry in vitro," 2003, J. Urol., 169:701-705.

NCBI Accession No. NP_005154, AKT1 kinase [Homo sapiens], Jul. 16, 2010.

NCBI accession No. NP_852664, phosphatidylinositol 3-kinase regulatory subunit alpha isoform 1 [Homo sapiens], Jul. 16, 2010.

NCBI Accession No. NP_852556, phosphatidylinositol 3-kinase regulatory subunit alpha isoform 2 [Homo sapiens], Jul. 16, 2010.

NCBI Accession No. NP_852665, phosphatidylinositol 3-kinase regulatory subunit alpha isoform 3 [Homo sapiens], Jul. 16, 2010.

NCBI Accession No. X 03363, (title unknown), Jul. 16, 2010.

Theory and Practice of Histological Techniques, 1977, Bancroft, J.D. and Stevens A, eds., Churchill Livingstone, Edinburgh.

Immobilized Enzymes Research and Development, 1978, Chibata, I., ed., Halsted Press, New York.

Protective Groups in Organic Synthesis, 1991, $2^{nd}$ Edition, Greene, T. and Wuts, P., John Wiley and Sons, New York.

Gel Electrophoresis of Proteins, A Practical Approach, 1981, Hames, B.D. and Rickwood, D., eds., IRL Press, Oxford.

Antibodies: A Laboratory Manual, 1988, Harlow, E. and Lane, D., eds., Cold Springs Harbor Laboratory Press, New York.

Bioconjugate Techniques, 1996, Hermanson, G., ed., Academic Press, New York.

Basic Methods in Antibody Production and Characterization, 2000, Howard, G. and Bethell, D., eds., CRC Press.

Manual of Histological Staining Method of the Armed Forces Institute of Pathology, 1960, $3^{rd}$ edition, Luna, L.G., ed., The Blakston Division McGraw-Hill Book Company, New York, NY.

High Resolution Chromatography: A Practical Approach, 1999, Millner, P., ed., Oxford University Press, New York.

HPLC of Macromolecules: A Practical Approach, 1989, Oliver, R., ed., Oxford University Press, Oxford, England.

Histochemistry. Theory and Applied, 1980, $4^{th}$ ed., Pearse, A., ed., Churchill Livingstone, Edinburgh.

Proteome Research: Two Dimensional Gel Electrophoresis and Identification Methods, 2000, Rabilloud, T., ed., Springer Verlag, Berlin.

Protein Purification. Principles and Practice, 1982, Scopes, R., ed., Springer-Verlag, New York.

Practical HPLC Method Development, 1988, Snyder, R. et al., eds., John Wiley & Sons, New York.

The Armed Forces Institute of Pathology Advanced Laboratory Methods in Histology and Pathology, 1994, Mikel, U., ed., Armed Forces Institute of Pathology, American Registry of Pathology, Washington, D.C.

Column Handbook for Size Exclusion Chromatography, 1999, Wu, C.-S. et al., ed., Academic Press, San Diego.

Zola, H., Monoclonal Antibodies-A Manual of Techniques, 1987, CRC Press.

Brantley, D. et al., "Soluble Eph A receptors inhibit tumor angiogenesis and progression in vivo," 2002, Oncogene, 21:7011-7026.

Fernandez, A. et al., "Angiogenic Potential of Prostate Carcinoma Cells Overexpressing bcl-2," 2001, J. Natl. Cancer Instit., 93:208-213.

Sasisekharan, R. et al., "Heparinase inhibits neovascularization," 1994, Proc. Natl. Acad. Sci. USA, 91:1524-1528.

* cited by examiner

Measurement of Homodimer Complexes

Measurement of Cell Surface Receptor Dimers

Pro32-NHS

Pro36-NHS

Pro44-NHS

Pro46-NHS

Pro52-NHS

Pro53-NHS

Pro99-NHS

DETECTION OF ACTIVATION OF ENDOTHELIAL CELLS AS SURROGATE MARKER FOR ANGIOGENESIS

This application claims the benefit of U.S. Provisional Application No. 60/625,694, filed Nov. 4, 2004, the contents of which is incorporated by reference in its entirety.

FIELD OF THE INVENTION

The present invention relates generally to methods for accessing angiogenesis through detection of the status of endothelial cell activation and more particularly to methods of determining angiogenic signal transduction pathway activation at a molecular level, and for using such status information to select patients responsive to pathway-specific drugs, and to rationally design effective therapy with drugs that specifically modulate angiogenesis signal transduction pathways.

DESCRIPTION OF RELATED ART

Angiogenesis is the fundamental process by which new blood vessels are formed. The process involves the migration of vascular endothelial cells into tissue, followed by the condensation of such endothelial cells into vessels. Angiogenesis may occur naturally or be induced by an angiogenic agent. The process is essential to a variety of normal body activities, such as reproduction, development and wound repair. Although the process is not completely understood, it involves a complex interplay of molecules that stimulate and molecules that inhibit the growth and migration of endothelial cells, the primary cells of the capillary blood vessels. Under normal conditions, these molecules appear to maintain the microvasculature in a quiescent state (i.e., without capillary growth) for prolonged periods which can last for several years or even decades. The turnover time for an endothelial cell is about 1,000 days. Under appropriate conditions, however (e.g., during wound repair), these same cells can undergo rapid proliferation and turnover within a much shorter period, and five days is typical under these circumstances. (Folkman et al. (1989) J. Biol. Chem., 267:10931-10934; and Folkman et al. (1987) Science 235: 442-447).

Although angiogenesis is a highly regulated process under normal conditions, many diseases (characterized as "angiogenic diseases") are driven by persistent unregulated angiogenesis. In such disease state, unregulated angiogenesis can either cause a particular disease directly or exacerbate an existing pathological condition. For example, ocular neovascularization has been implicated as the most common cause of blindness and underlies the pathology of approximately 20 eye diseases. In certain previously existing conditions such as arthritis, newly formed capillary blood vessels invade the joints and destroy cartilage. In diabetes, new capillaries formed in the retina invade the vitreous humor, causing bleeding and blindness.

Both the growth and metastasis of solid tumors are also angiogenesis-dependent (Folkman (1986) J. Cancer Res. 46:467-473; Folkman (1989) J. Nat. Cancer Inst. 82:4-6; Folkman et al. (1995) "Tumor Angiogenesis," Chapter 10, pp. 206-32, in The Molecular Basis of Cancer, Mendelsohn et al., eds., W. B. Saunders). It has been shown, for example, that tumors which enlarge to greater than 2 mm. in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner (1991) New Eng. J. Med. 324:1-8).

Cancer cells begin to promote angiogenesis early in tumorigenesis. This "angiogenic switch" (Hanahan et al. (1996) Cell 86:353-364) is characterized by oncogene-driven tumour expression of pro-angiogenic proteins (Rak et al. (2000) J. Invest. Dermatol. Symp. Proc. 5:24-33), such as vascular endothelial growth factor (VEGF), basic fibroblast growth factor (bFGF), interleukin-8 (IL-8), placenta-like growth factor (PLGF), transforming growth-factor-p (TGF-P), platelet-derived endothelial growth factor (PEGF), pleiotrophin and others (Relf et al. (1997) Cancer Res. 57:963-969; Carmeliet et al. (1998) Nature 394:485-490; and Fukumura et al. (1998) Cell 94:715-725). Tumour-associated hypoxic conditions also activate hypoxia-inducible factor-1a (HIF-1a) (Carmeliet et al., supra), which promotes upregulation of several angiogeneic factors. Fibroblasts in or near the tumour bed begin to produce pro-angiogenic factors, and tumors also recruit progenitor endothelial cells from bone marrow (Shi et al. (1998) Blood 92: 362-367). The angiogenic switch also involves downregulation of angiogenesis suppressor proteins, such as thrombospondin (Dameron et al. (1994) Science 265:1582-1584).

When used as drugs in tumor-bearing animals, natural inhibitors of angiogenesis can prevent the growth of small tumors (O'Reilly et al. (1994) Cell 79:315-328). Indeed, in some protocols, the application of such inhibitors leads to tumor regression and dormancy even after cessation of treatment (O'Reilly et al. (1997) Cell, 88, 277-285). Moreover, supplying inhibitors of angiogenesis to certain tumors can potentiate their response to other therapeutic regimens (e.g., chemotherapy) (see, e.g., Teischer et al. (1994) Int. J. Cancer 57: 920-25).

At present, there is no quantitative method for determining the total angiogenic output of a patient's tumor burden, so surrogate markers, such as angiogenic proteins present in serum, plasma, and urine. It is recognized that a significant change in the level of angiogenic proteins after initiation of treatment might provide an early indication of antiangiogenic activity before clinically demonstrable reduction in tumor size. Elevated angiogenic growth factors, proteases, and endothelial adhesion molecules have been detected in sera of patients with malignant diseases (Dirix et al. (1997) Br. J. Cancer 76:238-243). These important promoters of tumor angiogenesis include VEGF, bFGF, urokinase-type plasminogen activator and its soluble receptor (Xu et al. (1997) Hum Pathol 28:206-213), E-selectin and vascular cell adhesion molecules-1 (VCAM-1) (Banks et al. (1993) Br. J. Cancer 68:122-124), and von Willebrand's factor (vWF) (Gadducci et al. (1994) Gynecol. Oncol. 53:352-356). Of the many mediators of angiogenesis, VEGF and bFGF have been frequently measured as potential surrogate markers of antiangiogenic activity in many clinical studies.

Laser scanning cytometry (LSC) has also been used for quantitative analysis of antiangiogenic activity in clinical studies. In LSC measurement automated lasers detect individual cells within the mapped region of tumor biopsy samples based on multicolor immunofluorescence staining of biomarkers. Each cell is plotted on a scattergram based on its relative fluorescence intensity. LSC-generated scattergrams display the percentage of cell populations, for example, apoptotic endothelial cells. Alternative, cellular protein expression levels, e.g., phosphorylated VEGF receptor-2, may be measured by histogram analysis. See review by Davis et al. (2003) Br. J. Cancer 89:8-14.

Other techniques have been developed to assess changes in microvessel density, tumor blood flow, vascular permeability and in some cases metabolism, such as radiologic techniques including positron emission tomography (PET), magnetic resonance imaging, dynamic computed tomography and three-dimensional ultrasound. See review by Davis et al. (2003) Br. J. Cancer 89:8-14; and Morgan et al. (2003) J. Clin. Oncol. 21: 3955) For example, microvessal density (MVD) which is measured by counting the distance between vessels is used as a marker for angiogenesis based on the rational that as the distances decrease, the blood vessel density has increased, suggesting that the tumor is extremely angiogenic; and conversely, decease in MVD after therapy suggests that the antiangiogenic therapy is efficacious. Interstitial fluid pressure (IFP) is also used as a marker based on the rational that as the density of blood vessels increase, the interstitial pressures increases. Jain et al. (2004) Nat. Med. 10:145-147.

Recently ex vivo analyses of isolated peripheral blood cells have been used to monitor surrogate markers of antiangiogenic activity. In one study, a cytokine release assay was used to measure the effort of MM1270 (a matrix metalloproteinase inhibitor, previously termed CGS270231, Eatock et al. (1999) J. Clin. Oncol. 18:209a) on release of tumor necrosis factor-α from ex vivo stimulated peripheral blood cells (Levitt et al. (2001) Clin. Cancer Res. 7:1912-1922). Flow cytometry has also been used to quantify activated circulating endothelial cells from the peripheral blood of cancer patients in an effort to assess the effects of antiangiogenic activity (Mancuso et al. (2001) Blood 97:3658-3661; and Monestiroli et al. (2001) Cancer Res. 61:4341-4344). Mancuso et al. found that resting and activated endothelial cells are increased in newly diagnosed cancer patients and decline after cure; and Monestiroli et al. demonstrated that there was a strong correlation between circulating endothelial cells (CEC) and tumor volume and between CEC and tumor-generated VEGF.

There are various disadvantages associated with above approaches to assessing tumor angiogenesis. Although bFGF and VEGF levels have been developed as useful surrogate markers for determining the response to thalidomide or IFN-α therapy, there is an urgent need for surrogate markers to determine efficacy of other types of anti-angiogenic therapies. For most tumors, it is unlikely that quantification of circulating factors will serve as useful surrogate markers. Tumors can generate various positive and negative regulators of angiogenesis. Bergers et al. (2003) Nature Review 3:401-410. To determine whether a tumor is growing or regressing, it would be necessary to quantify the plasma or urine concentration of all of these mediators, which is not feasible at present. Quantification of microvessel density, although valuable as a predictor of future risk of metastasis or mortality, has not proven to be a useful indicator of efficacy of current anti-angiogenic therapy. Kerbel et al. (2002) Nature Review 2:727-739. In addition, the above methods do not directly measure activation of endothelial cells and are difficult to employ in practice.

SUMMARY OF THE INVENTION

The present invention provides an innovative approach to assessing angiogenesis through sensitive, direct detection of activation of cells that contribute to or promote angiogenesis, e.g., endothelial cells, stroma cells or tumor cells, at a molecular level. In general, activation of such cells is detected by measuring the levels of cellular components and their protein complexes participating in a specific angiogenesis signaling pathway in these cells. Compared with the currently available techniques for assessing angiogenesis, the methods provided in the present invention can sensitively and conveniently measure angiogenesis and detect the earliest indication of angiogenesis. Because the inventive methods can be employed to directly monitor a specific angiogenic signaling pathway, a more rational, patient-tailored therapy can be developed by targeting the specific pathway. Moreover, the inventive methods can also be used for assessing status of diseases associated with aberrant angiogenesis, such as the likelihood of developing the disease, presence or absence of the disease, prognosis of the disease and the likelihood of response or resistance to a particular anti-angiogenic therapy.

In one aspect, the present invention provides methods for detecting activation of endothelial cells in a test sample. The methods comprise the step of measuring the level of a protein complex in the endothelial cells in a test sample, wherein the protein complex is formed between a first cellular component and a second cellular component that are cellular components in an angiogenesis signaling pathway. A difference in the level of the protein complex relative to the level of the protein complex in a reference sample detects activation of endothelial cells in the test sample.

The protein complexes is formed between the first and second cellular components. The first and second cellular components can be any known cellular components in an angiogenesis signaling pathway, including but not limited to VEGFR, Nrp, heparin sulphate, VE-cadherin, Tie, VEGF, PIGF, PDGFR, EphA, EphB, Flt, FGFR, Stat, BAD, RSK, P13K, FAK, Src, P70S6K, SHC, SHC, Akt, Erk, JNK, P38, and MEK. In preferred embodiments, the protein complex is VEGFR1 homodimers, VEGFR2 homodimers, VEGFR1-VEGFR2 heterodimers, VEGFR2-VEGFR3 heterodimers, VEGFR2-SHC complexes, or VEGFR3-SHC complexes.

Test samples for use in the present invention may come from a wide variety of sources, including cell cultures, animal or plant tissues, patient biopsies, patient blood sample etc. In some embodiments, the test sample is a blood sample or a fixed tissue sample. In some embodiments, the test sample is obtained from an individual who is suspected of having a disease associated with undesirable angiogenesis, and wherein detecting activation of endothelial cells in the test sample indicates that the individual has the disease.

In some embodiments, the test sample may contain circulating endothelial cells, circulating endothelial cell progenitors or tumor endothelium. In certain embodiments, the methods further comprise isolating circulating endothelial cells or circulating endothelial cell progenitors. In preferred embodiments, circulating endothelial cells or circulating endothelial cell progenitors are isolated by immunomagnetic isolation.

The level of a protein complex in the endothelial cells can be measured by any techniques known to those of skill in the art. For example, immunoaffinity-based methods, cross-linking assays, or fluorescence resonance energy transfer can be utilized.

In preferred embodiments, assays using releasable molecular tags are used to detect protein complexes in the endothelial cells. In such embodiments, the step of measuring the protein complex in the endothelial cells comprises mixing (i) the test sample; (ii) a cleaving probe, which is capable of binding the first cellular component and has a cleavage-inducing moiety with an effective proximity; and (iii) one or more binding compounds, wherein each of the binding compounds is capable of binding the first or second cellular component and wherein each of the one or more binding compounds has one or more molecular tags each attached thereto by a cleavable linkage; wherein cleavage of the cleavable linkage(s) within the effective proximity of the cleaving-inducing moiety of the cleaving probe releases the molecular tag(s), wherein detecting the released molecular tag(s) provides a measurement of the protein complex. The cleaving probes, binding compounds, cleavage-inducing moiety and cleavable linkages are described in detail herein.

In some embodiments, the methods further comprise separating the released molecular tag(s). In other embodiments, The methods further comprise measuring the level of an effector protein in the angiogenesis signaling pathway that has a post-translational modification site in the endothelial cells in the test sample. The effector proteins are described herein.

In another aspect, the present invention provides methods for determining a disease status of an individual who has or likely has a disease associated with undesirable angiogenesis. The methods comprise measuring the level of a protein complex in the endothelial cells in a test sample from an individual, wherein the protein complex is formed between a first cellular component and a second cellular component that are cellular components in an angiogenesis signaling pathway. A difference between the level of the protein complex in the test sample and a reference level of the protein complex indicates the disease status of the patient.

In another aspect, the present invention provides methods for screening patients to determine the likelihood that a patient will respond to treatment by an anti-angiogenic agent. The methods comprise measuring the level of a protein complex in the endothelial cells in a test sample from a patient, wherein the protein complex is formed between a first cellular component and a second cellular component that are cellular components in an angiogenesis signaling pathway. An increase in the level of the protein complex in the test sample from the patient relative to a reference level characteristic of normal endothelial cells indicates that the likelihood that the patient will respond to treatment by an anti-angiogenic agent.

In another aspect, the present invention provides methods for determining whether a patient will respond to treatment by an anti-angiogenic agent. The methods comprise measuring the level of a protein complex in the endothelial cells in a test sample from a patient who has been treated with an anti-angiogenic agent, wherein the protein complex is formed between a first cellular component and a second cellular component that are cellular components in an angiogenesis signaling pathway. An increase in the level of the protein complex in the vascular (or CEC/CECP) endothelial cells from the test sample relative to a reference level of the protein complex in endothelial cells in the patient prior to the treatment, indicates that the patient is likely to respond to the treatment by the anti-angiogenic agent.

In another aspect, the present invention provides methods for determining whether a patient has developed resistance to treatment of an anti-angiogenic agent. The methods comprise measuring the level of a protein complex in the endothelial cells in a test sample from a patient who has been treated with an anti-angiogenic agent, wherein the protein complex is formed between a first cellular component and a second cellular component that are cellular components in an angiogenesis signaling pathway. An increase in the level of the protein complex in the endothelial cells from the test sample relative to a reference level of the protein complex in the endothelial cells in the patient prior to treatment, indicates that the patient has likely developed resistance to the treatment of the anti-angiogenic agent.

In another aspect, the present invention provides methods for detecting activation of endothelial cells in a test sample. The methods comprise measuring in a test sample the levels of two or more different cellular components that participate in one or more angiogenesis signaling pathways. A difference in the levels of the two or more different cellular components relative to reference levels of the two or more different cellular components, indicates activation of endothelial cells in a test sample.

The two or more cellular components can be any known cellular components that participate in one or more angiogenesis signaling pathway and are described in detail herein.

In some embodiments, the test sample may contain circulating endothelial cells, circulating endothelial cell progenitors or tumor endothelium. In certain embodiments, the methods further comprise isolating circulating endothelial cells or circulating endothelial cell progenitors. In preferred embodiments, circulating endothelial cells or circulating endothelial cell progenitors are isolated by immunomagnetic isolation.

The level of the two or more cellular components can be measured by any techniques known to those of skill in the art. For example, immunoaffinity-based methods, cross-linking assays, or fluorescence resonance energy transfer can be utilized.

In preferred embodiments, assays using releasable molecular tags are used to detect the level of two more cellular components in the endothelial cells. In such embodiments, the step of measuring the levels of two or more different cellular components in the endothelial cells comprises mixing (i) the test sample; (ii) a cleaving probe, which is capable of binding one of the two or more cellular components and has a cleavage-inducing moiety with an effective proximity; and (iii) one or more binding compounds, wherein each of the two or more cellular components is bound by at least one member of the one or more binding compounds, and wherein each of the binding compounds has one or more molecular tags each attached thereto by a cleavable linkage; wherein cleavage of the cleavable linkage(s) within the effective proximity of the cleaving-inducing moiety of the cleaving probe releases the molecular tag(s), wherein detecting the released molecular tag(s) provides a measurement of the levels of two or more different cellular components in the endothelial cells. The cleaving probes, binding compounds, cleavage-inducing moiety and cleavable linkages are described in detail herein.

In some embodiments, the methods further comprise separating the released molecular tag(s). In other embodiments, The methods further comprise measuring the level of an effector protein in the angiogenesis signaling pathway that has a post-translational modification site in the endothelial cells in the test sample. The effector proteins are described herein.

DEFINITIONS

Figure 1:
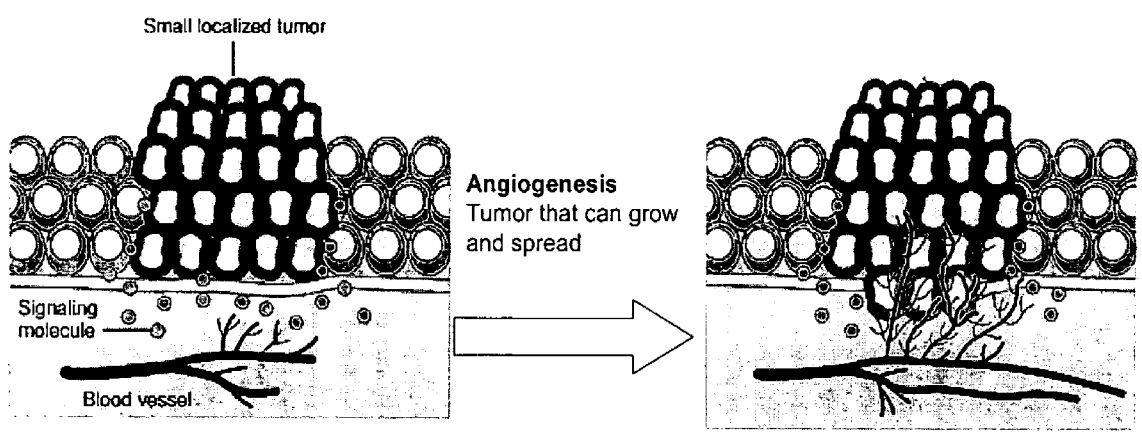
FIG. 1 illustrates the role angiogenesis plays in the growth and metastasis of a small localized tumor.

"Akt protein" means a human protein that is a member of the set of PKBa/Akt1, PKBb/Akt2, PKBg/Akt3, PKBg-1, and proteins having substantially identical amino acid sequences thereof, and that has protein kinase activity whenever phosphorylated by a PI3K protein. In one aspect, an Akt protein has kinase activity whenever either or both of a tyrosine at a location number from 305 to 310 is phosphorylated and a serine at location number from 470 to 475 is phosphorylated. Akt proteins are described under various NCBI accession numbers, including NP_005154, and in Nicholson et al., Cellular Signalling, 14: 381-395 (2002); Kandel et al., Exp. Cell. Res., 253: 210-229 (1999); and like references, all of which are incorporated herein by references.

"Effector protein" means an intracellular protein that is a component of a signal transduction pathway and that may be chemically altered resulting in the acquisition or loss of an activity or property. Such chemical alteration may include any of the post-translational modifications listed below as well as processing by proteinases. In one aspect, effector proteins are chemically modified by phosphorylation and acquire protein kinase activity as a result of such phosphorylation. In another aspect, effector proteins are chemically modified by phosphorylation and lose protein kinase activity as a result of such phosphorylation. In another aspect, effector proteins are chemically modified by phosphorylation and lose the ability to form stable complexes with particular proteins as a result of such phosphorylation. Exemplary effector proteins include, but are not limited to, Akt proteins, Erk proteins, p38 proteins, and Jnk proteins. In regard to post-translational modifications of effector proteins, an effector protein may have one or more sites, referred to herein as a "post-translational modification site," which are characteristic amino acids of the effector protein where a post-translational modification may be attached or removed in the course of a signal transduction event.

"MAPK protein" means a human protein of the set of Erk1 proteins, Erk2 proteins (collectively referred to as Erk1/2 proteins), p38 proteins, Jnk proteins, and proteins having amino acid sequences substantially identical thereto.

"Phosphatidylinositol 3 kinase protein," or equivalently a "PI3K protein," means a human intracellular protein of the set of human proteins describe under NCBI accession numbers NP_852664, NP_852556, and NP_852665, and proteins having amino acid sequences substantially identical thereto.

"Substantially identical" in reference to proteins or amino acid sequences of proteins in a family of related proteins that are being compared means either that one protein has an amino acid sequence that is at least fifty percent identical to the other protein or that one protein is an isoform or splice variant of the same gene as the other protein. In one aspect, substantially identical means one protein, or amino acid sequence thereof, is at least eighty percent identical to the other protein, or amino acid sequence thereof.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained. Guidance in the production and selection of antibodies for use in immunoassays, including such assays employing releasable molecular tag (as described below) can be found in readily available texts and manuals, e.g. Harlow and Lane, Antibodies: A Laboratory Manual (Cold Spring Harbor Laboratory Press, New York, 1988); Howard and Bethell, Basic Methods in Antibody Production and Characterization (CRC Press, 2001); Wild, editor, The Immunoassay Handbook (Stockton Press, New York, 1994), and the like.

"Antibody binding composition" means a molecule or a complex of molecules that comprises one or more antibodies, or fragments thereof, and derives its binding specificity from such antibody or antibody fragment. Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photosensitizers, or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Antigenic determinant," or "epitope" means a site on the surface of a molecule, usually a protein, to which a single antibody molecule binds; generally a protein has several or many different antigenic determinants and reacts with antibodies of many different specificities. A preferred antigenic determinant is a phosphorylation site of a protein.

"Binding moiety" means any molecule to which molecular tags can be directly or indirectly attached that is capable of specifically binding to an analyte. Binding moieties include, but are not limited to, antibodies, antibody binding compositions, peptides, proteins, nucleic acids, and organic molecules having a molecular weight of up to 1000 daltons and consisting of atoms selected from the group consisting of hydrogen, carbon, oxygen, nitrogen, sulfur, and phosphorus. Preferably, binding moieties are antibodies or antibody binding compositions.

"Complex" as used herein means an assemblage or aggregate of molecules in direct or indirect contact with one another. In one aspect, "contact," or more particularly, "direct contact" in reference to a complex of molecules, or in reference to specificity or specific binding, means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" usually refers to a stable aggregate of two or more proteins, and is equivalently referred to as a "protein-protein complex." Most typically, a "complex" refers to a stable aggregate of two proteins. As used herein, an "intracellular complex" or "intracellular protein-protein complex," refers to a complex of proteins normally found in the cytoplasm or nucleus of a biological cell, and may include complexes of one or more intracellular proteins and a surface membrane receptor. In another aspect, a complex is a stable aggregate comprising two proteins, or from 2 to 4 proteins, or from 2 to 6 proteins. As used herein, a "signaling complex" is an intracellular protein-protein complex that is a component of a signaling pathway.

"Dimer" in reference to cell surface membrane receptors means a complex of two or more membrane-bound receptor proteins that may be the same or different. Dimers of identical receptors are referred to as "homodimers" and dimers of different receptors are referred to as "heterodimers." Dimers usually consist of two receptors in contact with one another. Dimers may be created in a cell surface membrane by passive processes, such as Van der Waal interactions, and the like, as described above in the definition of "complex," or dimers may be created by active processes, such as by ligand-induced dimerization, covalent linkages, interaction with intracellular components, or the like, e.g. Schlessinger, Cell, 103: 211-225 (2000).

"Disease status" includes, but is not limited to, the following features: likelihood of contracting a disease, presence or absence of a disease, prognosis of disease severity, and likelihood that a patient will respond to treatment by a particular therapeutic agent that modulate an angiogenesis signal transduction pathway. In regard to cancer, "disease status" further includes detection of precancerous or cancerous cells or tissues, the selection of patients that are likely to respond to treatment by a therapeutic agent that inhibits angiogenesis of tumors, and the ameliorative effects of treatment with such therapeutic agents.

"Her receptor" is a receptor protein tyrosine kinase which belongs to the ErbB receptor family and includes EGFR ("Her1"), ErbB2 ("Her2"), ErbB3 ("Her3") and ErbB4 ("Her4") receptors. The Her receptor generally comprises an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The Her receptor may be a native sequence ErbB receptor or an amino acid sequence variant thereof. Preferably the ErbB receptor is native sequence human ErbB receptor. In one aspect, the Her receptor includes truncated versions of Her receptors, including but not limited to, EGFRvIII and p95Her2, disclosed in Chu et al., Biochem. J., 324: 855-861 (1997); Xia et al., Oncogene, 23: 646-653 (2004); and the like. As used herein, a "Her receptor complex" is a complex or receptor complex containing at least one Her receptor.

The terms "ErbB1", "epidermal growth factor receptor" and "EGFR" and "Her1" are used interchangeably herein and refer to native sequence EGFR as disclosed, for example, in Carpenter et al. Ann. Rev. Biochem. 56:881-914 (1987), including variants thereof (e.g. a deletion mutant EGFR as in Humphrey et al. PNAS (USA) 87:4207-4211 (1990)). erbB1 refers to the gene encoding the EGFR protein product. Examples of antibodies which bind to EGFR include MAb 579 (ATCC CRL RB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.).

"Her2", "ErbB2" "c-Erb-B2" are used interchangeably. Unless indicated otherwise, the terms "ErbB2" "c-Erb-B2" and "Her2" when used herein refer to the human protein. The human ErbB2 gene and ErbB2 protein are, for example, described in Semba et al., PNAS (USA) 82:6497-650 (1985) and Yamamoto et al. Nature 319:230-234 (1986) (Genebank accession number X03363). Examples of antibodies that specifically bind to Her2 are disclosed in U.S. Pat. Nos. 5,677, 171; 5,772,997; Fendly et al., Cancer Res., 50: 1550-1558 (1990); and the like.

"ErbB3" and "Her3" refer to the receptor polypeptide as disclosed, for example, in U.S. Pat. Nos. 5,183,884 and 5,480, 968 as well as Kraus et al. PNAS (USA) 86:9193-9197 (1989), including variants thereof. Examples of antibodies which bind Her3 are described in U.S. Pat. No. 5,968,511, e.g. the 8B8 antibody (ATCC HB 12070).

The terms "ErbB4" and "Her4" herein refer to the receptor polypeptide as disclosed, for example, in EP Pat Appln No 599,274; Plowman et al., Proc. Natl. Acad. Sci. USA, 90:1746-1750 (1993); and Plowman et al., Nature, 366:473-475 (1993), including variants thereof such as the Her4 isoforms disclosed in WO 99/19488.

"Insulin-like growth factor-1 receptor" or "IGF-1R" means a human receptor tyrosine kinase substantially identical to those disclosed in Ullrich et al., EMBO J., 5: 2503-2512 (1986) or Steele-Perkins et al., J. Biol. Chem., 263: 11486-11492 (1988).

"Isolated" in reference to a polypeptide or protein means substantially separated from the components of its natural environment. Preferably, an isolated polypeptide or protein is a composition that consists of at least eighty percent of the polypeptide or protein identified by sequence on a weight basis as compared to components of its natural environment; more preferably, such composition consists of at least ninety-five percent of the polypeptide or protein identified by sequence on a weight basis as compared to components of its natural environment; and still more preferably, such composition consists of at least ninety-nine percent of the polypeptide or protein identified by sequence on a weight basis as compared to components of its natural environment. Most preferably, an isolated polypeptide or protein is a homogeneous composition that can be resolved as a single spot after conventional separation by two-dimensional gel electrophoresis based on molecular weight and isoelectric point. Protocols for such analysis by conventional two-dimensional gel electrophoresis are well known to one of ordinary skill in the art, e.g. Hames and Rickwood, Editors, Gel Electrophoresis of Proteins: A Practical Approach (IRL Press, Oxford, 1981); Scopes, Protein Purification (Springer-Verlag, New York, 1982); Rabilloud, Editor, Proteome Research: Two-Dimensional Gel Electrophoresis and Identification Methods (Springer-Verlag, Berlin, 2000).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Pathway-specific drug" means a drug designed to inhibit or block a signal transduction pathway by interacting with, or targeting, a component of the pathway to inhibit or block a protein-protein interaction, such as receptor dimerization, or to inhibit or block an enzymatic activity, such as a kinase activity or a phosphatase activity. Tables 1 and 2 (shown in Section 5 entitled "Examples of Antiangiogenic Agents" below) list exemplary angiogenesis inhibitors that target various angiogenesis pathways.

"Percent identical," or like term, used in respect of the comparison of a reference sequence and another sequence (i.e. a "candidate" sequence) means that in an optimal alignment between the two sequences, the candidate sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms described by Needleman and Wunsch, J. Mol. Biol., 48: 443-453 (1970)("GAP" program of Wisconsin Sequence Analysis Package, Genetics Computer Group, Madison, Wis.). Other software packages in the art for constructing alignments and calculating percentage identity or other measures of similarity include the "Best-Fit" program, based on the algorithm of Smith and Waterman, Advances in Applied Mathematics, 2: 482-489 (1981) (Wisconsin Sequence Analysis Package, Genetics Computer Group, Madison, Wis.). In other words, for example, to obtain a polypeptide having an amino acid sequence at least 95 percent identical to a reference amino acid sequence, up to five percent of the amino acid residues in the reference sequence many be deleted or substituted with another amino acid, or a number of amino acids up to five percent of the total amino acid residues in the reference sequence may be inserted into the reference sequence. These alterations of the reference sequence many occur at the amino or carboxy terminal positions of the reference amino acid sequence or anywhere between those terminal positions, interspersed either individually among residues in the reference sequence of in one or more contiguous groups with in the references sequence. It is understood that in making comparisons with reference sequences of the invention that candidate sequence may be a component or segment of a larger polypeptide or polynucleotide and that such comparisons for the purpose computing percentage identity is to be carried out with respect to the relevant component or segment.

"Platelet-derived growth factor receptor" or "PDGFR" means a human receptor tyrosine kinase protein that is substantially identical to PDGFRα or PDGFRβ, or variants thereof, described in Heldin et al., Physiological Reviews, 79: 1283-1316 (1999). In one aspect, the invention includes determining the status of cancers, pre-cancerous conditions, fibrotic or sclerotic conditions by measuring one or more dimers of the following group: PDGFRα homodimers, PDGFRβ homodimers, and PDGFRα-PDGFRβ heterodimers. In particular, fibrotic conditions include lung or kidney fibrosis, and sclerotic conditions include atherosclerosis. Cancers include, but are not limited to, breast cancer, colorectal carcinoma, glioblastoma, and ovarian carcinoma. Reference to "PDGFR" alone is understood to mean "PDGFRα" or "PDGFRβ." PDGFRs are disclosed in Heldin et al., Physiological Reviews, 79: 1283-1316 (1999), and in various NCBI accession numbers.

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological cell, folded into a defined three-dimensional structure. Proteins are generally from about 5,000 to about 5,000,000 or more in molecular weight, more usually from about 5,000 to about 1,000,000 molecular weight, and may include post-translational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, farnesylation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation, and ubiquitination, e.g. Wold, F., Post-translational Protein Modifications: Perspectives and Prospects, pgs. 1-12 in Post-translational Covalent Modification of Proteins, B. C. Johnson, Ed., Academic Press, New York, 1983. In one aspect, post-translational modifications are usually phosphorylations of proteins that are components of a signaling pathway. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, and the like.

"Reference sample" means one or more cell, xenograft, or tissue samples that are representative of a normal or non-diseased state to which measurements on patient samples are compared to determine whether a receptor complex is present in excess or is present in reduced amount in the patient sample. The nature of the reference sample is a matter of design choice for a particular assay and may be derived or determined from normal tissue of the patient him- or herself, or from tissues from a population of healthy individuals. Preferably, values relating to amounts of receptor complexes in reference samples are obtained under essentially identical experimental conditions as corresponding values for patient samples being tested. Reference samples may be from the same kind of tissue as that the patient sample, or it may be from different tissue types, and the population from which reference samples are obtained may be selected for characteristics that match those of the patient, such as age, sex, race, and the like. Typically, in assays of the invention, amounts of receptor complexes on patient samples are compared to corresponding values of reference samples that have been previously tabulated and are provided as average ranges, average values with standard deviations, or like representations.

"Receptor complex" means a complex that comprises at least one cell surface membrane receptor. Receptor complexes may include a dimer of cell surface membrane receptors, or one or more intracellular proteins, such as adaptor proteins, that form links in the various signaling pathways.

"Receptor tyrosine kinase," or "RTK," means a human receptor protein having intracellular kinase activity and being selected from the RTK family of proteins described in Schlessinger, Cell, 103: 211-225 (2000); and Blume-Jensen and Hunter (cited above). "Receptor tyrosine kinase dimer" means a complex in a cell surface membrane comprising two receptor tyrosine kinase proteins. In some aspects, a receptor tyrosine kinase dimer may comprise two covalently linked receptor tyrosine kinase proteins.

"Response index" means a number that is a value of a function that depends on one or more measured quantities or arithmetic expressions thereof. "Function" as used herein has its conventional mathematical definition. The measured quantities include the amounts of cell surface receptors, cell surface receptor complexes, signaling complexes, and post-translational modifications thereof. The function and arithmetic expressions employed depend on several factors including, but not limited to, the pathway-specific drug being considered, the type of disease, genotype of a patient, and the like.

"Sample" or "tissue sample" or "patient sample" or "patient cell or tissue sample" or "specimen" each means a collection of similar cells obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like. In one aspect of the invention, tissue samples or patient samples are fixed, particularly conventional formalin-fixed paraffin-embedded samples. Such samples are typically used in an assay for receptor complexes in the form of thin sections, e.g. 3-10 µm thick, of fixed tissue mounted on a microscope slide, or equivalent surface. Such samples also typically undergo a conventional re-hydration procedure, and optionally, an antigen retrieval procedure as a part of, or preliminary to, assay measurements.

"Separation profile" in reference to the separation of molecular tags means a chart, graph, curve, bar graph, or other representation of signal intensity data versus a parameter related to the molecular tags, such as retention time, mass, or the like, that provides a readout, or measure, of the number of molecular tags of each type produced in an assay. A separation profile may be an electropherogram, a chromatogram, an electrochromatogram, a mass spectrogram, or like graphical representation of data depending on the separation technique employed. A "peak" or a "band" or a "zone" in reference to a separation profile means a region where a separated compound is concentrated. There may be multiple separation profiles for a single assay if, for example, different molecular tags have different-fluorescent labels having distinct emission spectra and data is collected and recorded at multiple wavelengths. In one aspect, released molecular tags are separated by differences in electrophoretic mobility to form an electropherogram wherein different molecular tags correspond to distinct peaks on the electropherogram. A measure of the distinctness, or lack of overlap, of adjacent peaks in an electropherogram is "electrophoretic resolution," which may be taken as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like. Electropherograms may be analyzed to associate features in the data with the presence, absence, or quantities of molecular tags using analysis programs, such as disclosed in Williams et al., U.S. patent publication 2003/0170734 A1.

"SHC" (standing for "Src homology 2/α-collagen-related") means any one of a family of adaptor proteins (66, 52, and 46 kDalton) in RTK signaling pathways substantially identical to those described in Pelicci et al., Cell, 70: 93-104 (1992). In one aspect, SHC means the human versions of such adaptor proteins.

"Signaling pathway" or "signal transduction pathway" means a series of molecular events usually beginning with the interaction of cell surface receptor and/or receptor dimer with an extracellular ligand or with the binding of an intracellular molecule to a phosphorylated site of a cell surface receptor. Such beginning event then triggers a series of further molecular interactions or events, wherein the series of such events or interactions results in a regulation of gene expression, for example, by regulation of transcription in the nucleus of a cell, or by regulation of the processing or translation of mRNA transcripts.

"Specific" or "specificity" in reference to the binding of one molecule to another molecule, such as a binding compound, or probe, for a target analyte or complex, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like.

"Spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al., pgs. 21-76, in Flow Cytometry: Instrumentation and Data Analysis (Academic Press, New York, 1985).

"Substantially identical" in reference to proteins or amino acid sequences of proteins in a family of related proteins that are being compared means either that one protein has an amino acid sequence that is at least fifty percent identical to the other protein or that one protein is an isoform or splice variant of the same gene as the other protein. In one aspect, substantially identical means one protein, or amino acid sequence thereof, is at least eighty percent identical to the other protein, or amino acid sequence thereof.

"VEGF receptor" or "VEGFR" as used herein refers to a cellular receptor for vascular endothelial growth factor (VEGF), ordinarily a cell-surface receptor found on vascular endothelial cells, as well as variants thereof which retain the ability to bind human VEGF. VEGF receptors include VEGFR1 (also known as Flt1), VEGFR2 (also know as Flk1 or KDR), and VEGFR3 (also known as Flt4). These receptors are described in DeVries et al., *Science* 255:989 (1992); Shibuya et al., *Oncogene* 5:519 (1990); Matthews et al., *Proc. Nat. Acad. Sci.* 88:9026 (1991); Terman et al., Oncogene 6:1677 (1991); Terman et al., *Biochem. Biophys. Res. Commun.* 187:1579 (1992). Dimers of VEGF receptors are described in Shibuya, Cell Structure and Function, 26: 25-35 (2001); and Ferrara et al., Nature Medicine, 9: 669-676 (2003). In one aspect, the invention includes assessing aberrant angiogenesis, or diseases characterized by aberrant angiogenesis, by measuring one or more dimers of the following group: VEGFR1 homodimers, VEGFR2 homodimers, VEGFR1-VEGFR2 heterodimers, and VEGFR2-VEGFR3 heterodimers.

DETAILED DESCRIPTION OF THE INVENTION

Angiogenesis is the development of new blood vessels from existing microvessels. The process of generating new blood vessels plays an important role in embryonic development, in the inflammatory response, in the development of metastases (tumor induced angiogenesis or TIA), in diabetic retinopathy, in the formation of the arthritic panus and in psoriasis. Under normal physiological conditions, humans or animals only undergo angiogenesis in very specific, restricted situations. For example, angiogenesis is normally observed in wound healing, in fetal and embryonal development and in the formation of the corpus luteum, endometrium and placenta. The control of angiogenesis is a highly regulated system involving angiogenic stimulators and inhibitors. The control of angiogenesis has been found to be altered in certain disease states and, in many cases, the pathological damage associated with the disease is related to the uncontrolled angiogenesis.

It is well established that angiogenesis is an important requirement for the growth and metastasis of tumors (Folkman (1987) Science 235:442-447; Folkman (1990) J. Nat. Can. Inst. 82:4-6; Talks et al. (2000) Brit. J. Haematol. 109: 477-489; and Napoleone et al. (1999) Kidney Internatl. 56:794-814). FIG. 1 illustrates the role angiogenesis plays in the growth and metastasis of a small localized tumor.

A wide variety of methods and compositions have been developed for inhibiting undesirable, aberrant angiogenesis, either by competitively inhibiting an angiogenesis factor or by some other mechanisms. Complete or partial suppression of vascular growth by a number of different strategies has been consistently associated with suppression of tumor expansion and even reduction of tumor burden. However, none of the treatment is effective for all the cancer patients who have the same cancer and symptoms. The traditional diagnosis is based primarily on tumor size, appearance and staging of the disease. Others have used a single biomarker of tumor, such as expression levels of the Her-2/neu gene or serum levels of VEGF, to predict patients' response to treatment, but most of the single marker alone does not correlate with it very well.

The inventors believe that since angiogenesis is a complex biological process with various factors involved, a more sophisticated analysis of multiple cellular components is needed to sensitively and accurately assess tumor angiogenesis in response to various antiangiogenic interventions. Due to differences in pharmacogenomic profiles, patients can have different degrees of response to the treatment of a specific antiangiogenic agent that targets a particular angiogenic factor or pathway. Further, blockage of one angiogenic pathway may trigger activation of alternatives ones, resulting in the development of resistance to the antiangiogenic agent. Thus, the inventors believe that unconventional approaches should be taken to circumvent the problems associated with multiple, complex angiogenic pathways in the diagnosis, prevention and therapeutic treatment of diseases or conditions associated with undesirable, aberrant angiogenesis.

The present invention provides an innovative approach to assessing angiogenesis through sensitive, direct detection of activation of cells that contribute to angiogenesis, e.g., endothelial cells or tumor cells, at a molecular level. In general, activation of such cells, e.g., endothelial cells, is detected by measuring the levels of multiple cellular components (not all interactions are cellular) and their protein complexes participating in a specific angiogenesis signaling pathway in endothelial cells. Compared with the currently available techniques for assessing angiogenesis, the methods provided in the present invention can sensitively and conveniently measure angiogenesis and detect the earliest indication of angiogenesis without counting blood vessels and measuring interstitial fluid pressure. Because the inventive methods can be employed to directly monitor a specific angiogenic signaling pathway, a more rational, patient-tailored therapy can be developed by targeting the specific pathway. Moreover, the inventive methods can also be used for assessing status of diseases associated with aberrant angiogenesis, such as the likelihood of developing the disease, presence or absence of the disease, prognosis of the disease and the likelihood of response or resistance to a particular anti-angiogenic therapy.

According to the invention, status of endothelial cell activation can be assessed by analyzing a patient's peripheral blood samples. Compared to biopsy and measurement of interstitial fluid pressure, this approach is much less invasive and the analysis can be performed more frequently to allow closer monitoring of the patient's prognosis.

In one aspect of the invention, a method is provided for detecting activation of endothelial cells by measuring the level of a protein complex (should be more than one complex at a time) in the endothelial cells in a test sample (e.g., a sample containing CEC, CECP or endothelium). The protein complex is formed between a first cellular component and a second cellular component that are cellular components in an angiogenesis signaling pathway. The first and second cellular components are preferably angiogenic receptor (e.g., receptor tyrosine kinases (RTK)), their post-translational modifications and downstream effector proteins. The method may optionally include measurement of levels of individual cellular components.

RTK are glycoproteins that are activated by binding of their cognate ligands to the extracellular region. (Lowes V L, et al. (2002) Neurosignals 11:5-19). Ligand binding stabilizes a dimeric configuration of the extracellular domains that is required for a subsequent transduction of the extracellular signal to the cytoplasm. This is achieved by phosphorylation of tyrosine residues on the cytoplasmic portion of the receptors themselves (trans-autophosphorylation) and on downstream signaling proteins. Downregulation of RTK occurs via receptor-mediated endocytosis, ubiquitin-directed proteolysis and dephosphorylation by protein tyrosine phosphatases.

Figure 2:
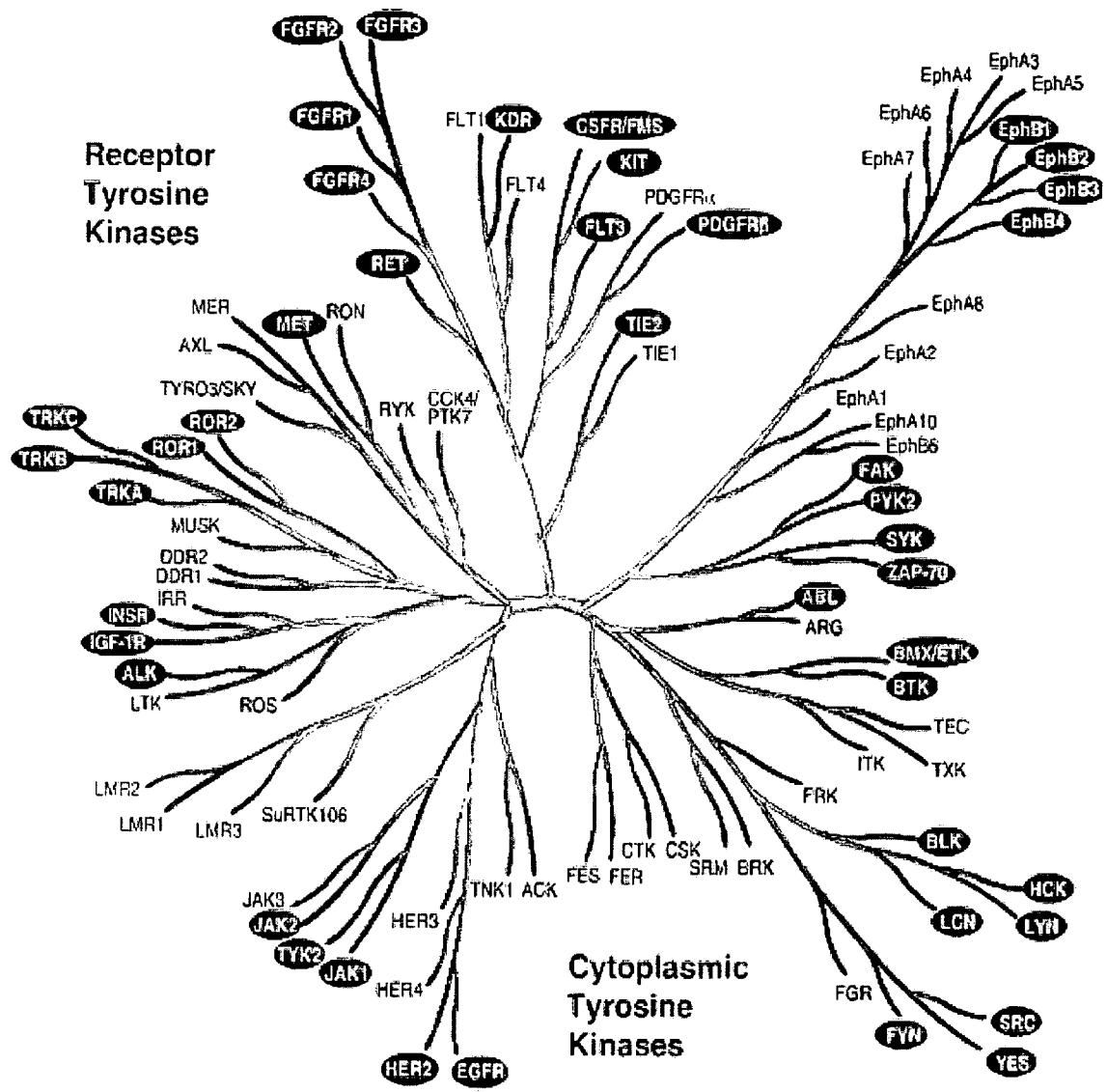
FIG. 2 illustrates exemplary families of receptor tyrosine kinase (RTK).
Figure 3:
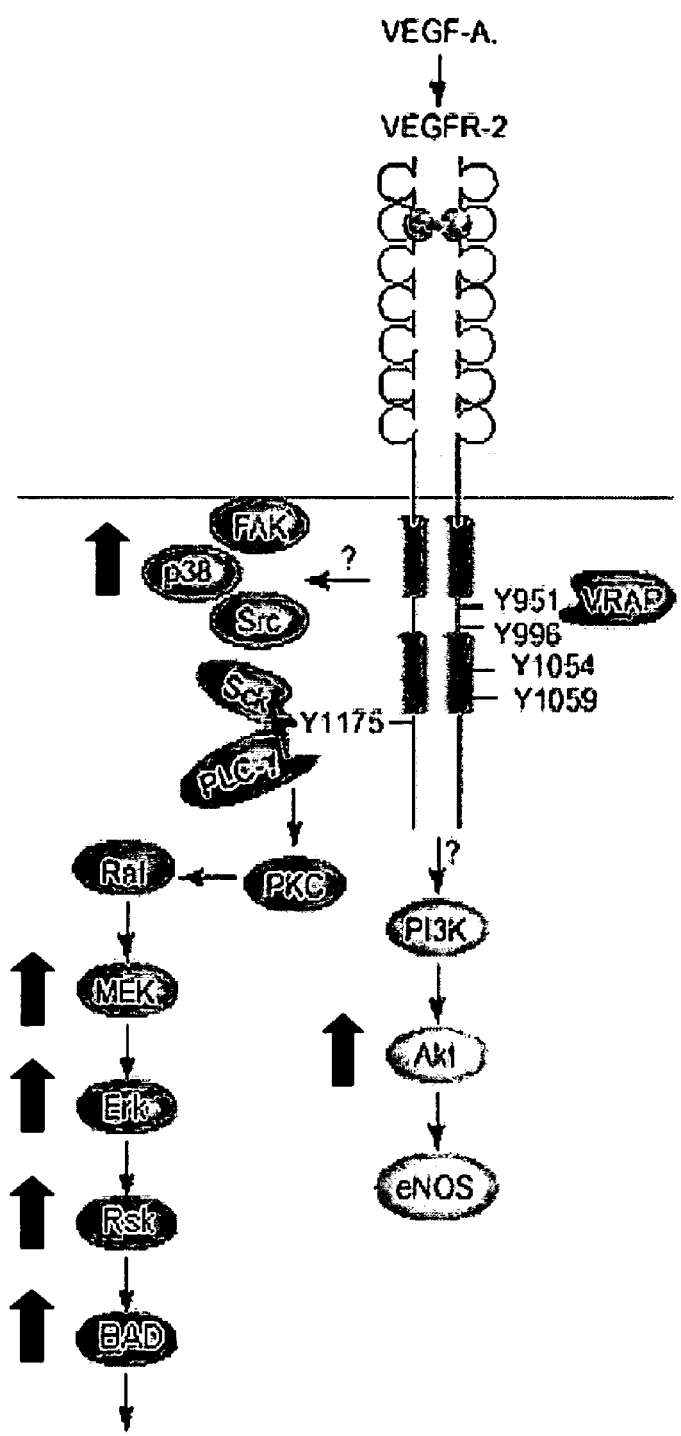
FIG. 3 illustrates exemplary signal transduction pathways of VEGFR2 in response to VEGF.

As illustrated in FIG. 2, RTK comprises many families of receptors for the epidermal growth factor (EGFR), vascular endothelial growth factor (VEGFR), angiopoietin, nerve growth factor (NGFR), fibroblast growth factor (FGFR), platelet-derived growth factor (PDGFR), insulin and ephrin receptor families, Met and Ror families. Lowes V L, et al. (2002) Neurosignals 11:5-19. In particular, VEGFR2 is the major mediator of the mitogenic, angiogenic and permeability-enhancing effects of VEGF. As illustrated in FIG. 3, in response to VEGF, endothelial cells are activated through homodimerization of VEGFR2 which triggers a series of downstream signaling events involving effector proteins such as Erk (MAP kinase), Jnk (Jun kinase), MEK (MAP kinase kinase), FAK (focal adhesion kinase), p38, Src (a tyrosine kinase), PKC (phosphokinase C), Rsk (Ribosomal S6 Protein Kinase), BAD, PI3K (phosphoinositide 3-kinase), Akt (a serine-threonine protein kinase) and eNOS (endothelial nitric oxide synthase).

Examples of the protein complexes to be evaluated include, but are not limited to, protein complexes formed by VEGFR, PDGFR, FGFR, Tie, EphA and B. The triggered intracellular protein complexes in response to these receptors to be evaluated include, but are not limited to, Stat, BAD, RSK, PI3K, FAK, Src, P70S6K, SHC, SHC, Akt, Erk, JNK, P38, and MEK. The extracellular protein interactions to be evaluated involve, but are not limited to, VE-cadherin, heparin sulphate. In particular, the following dimers are preferably evaluated: 1) VEGFR-1, 2, 3 homodimers; 2) VEGFR-1, 2, 3 phosphorylation; 3) VEGFR-2/Nrp-1, Nrp-2 heterodimer; 4) VEGFR-2/heparin sulphate complex; 5) VEGFR-2, VE-cadherin complex; 6) Tie 1/Tie 2 heterodimer; 7) Tie 1 endodomain/Tie 2 heterodimer; 8) VEGF/PlGF heterodimer; 9) PDGFR homo- and heterodimers; 10) EphA-1, 2, 3, 4, 5, 6, 7, 8, 10, EphB-1, 2, 3, 4, 6 homo- and heterodimers; 11) Flt3 homo- and heterodimers 12) FGFR-1, 2, 3, 4 homo- and heterodimers.

In another aspect of the invention, a method is provided for detecting activation of endothelial cells by measuring the levels of a first cellular component and a second cellular component that participate in an angiogenesis signaling pathway in the endothelial cells in a test sample (e.g., a sample containing CEC, CECP or endothelium). The first and second cellular components are preferably angiogenic receptor (e.g., receptor tyrosine kinases (RTK)), their post-translational modifications and downstream effector proteins.

By measuring levels of multiple cellular components and their complexes that participate in a specific angiogenic pathway in endothelial cells, angiogenesis can be assessed at molecular levels to provide extremely valuable information on the mechanisms of action. Such information can be used to assess status of a disease associated with undesirable angiogenesis, to select patients for clinical trials of antiangiogenic drugs, and to guide diagnosis and therapy of such a disease by targeting the specific angiogenic pathway.

Thus, in another aspect of the invention, a method is provided for determining a disease status of an individual who has or likely has a disease associated with undesirable angiogenesis. The method comprises: providing a test sample comprising endothelial cells from the individual; measuring the level of a protein complex in the endothelial cells from the test sample, wherein the protein complex is formed between a first cellular component and a second cellular component that are cellular components in an angiogenesis signaling pathway, and comparing the level of the protein complex with a reference level of the protein complex, wherein a difference in the level of the protein complex indicates the disease status of the patient. For example, a test sample containing CEC or CECP isolated from peripheral blood of the individual can be analyzed for activation of endothelial cells which may be indicated by increased levels of VEGFR2 homodimers and heterodimers, and optionally increased levels of phosphorylated VEGFR. As a surrogate marker of angiogenesis, activation of endothelial cells in the individual indicates that he/she is likely to have a disease associated with undesirable angiogenesis.

In yet another aspect of the invention, a method is provided for screening patients to determine the likelihood that a patient will respond to treatment by an anti-angiogenic agent. The method comprises: providing a test sample comprising endothelial cells from the patient to be screened; measuring the level of a protein complex in the endothelial cells from the test sample, wherein the protein complex is formed between a first cellular component and a second cellular component that are cellular components in an angiogenesis signaling pathway; and classifying those patients having an increased level of the protein complex relative to a reference level characteristic of normal endothelial cells as being more likely to respond to treatment by an anti-angiogenic agent. For example, a test sample containing CEC or CECP isolated from peripheral blood of the patient (or a test sample containing tumor endothelium of the patient) can be analyzed for activation of endothelial cells which may be indicated by increased levels of VEGFR2 homodimers and heterodimers, and optionally increased levels of phosphorylated VEGFR. As a surrogate marker of angiogenesis, activation of endothelial cells in the patient indicates that the patient is likely to respond to treatment of an anti-angiogenic agent.

In yet another aspect of the invention, a method is provided for determining whether a patient will respond to treatment by an anti-angiogenic agent. The method comprises: providing a test sample comprising endothelial cells from the patient who has been treated with an anti-angiogenic agent; measuring the level of a protein complex in the endothelial cells from the test sample, wherein the protein complex is formed between a first cellular component and a second cellular component that are cellular components in an angiogenesis signaling pathway; and comparing the level of the protein complex relative to a reference level of the protein complex in endothelial cells in the patient prior to the treatment, wherein a decreased level of the protein complex in the vascular (or CEC/CECP) endothelial cells from the test sample indicates that the patient is likely to respond to the treatment by the anti-angiogenic agent. For example, a test sample containing CEC or CECP isolated from peripheral blood of the patient (or a test sample containing tumor endothelium of the patient) can be analyzed for inhibition of activation of endothelial cells which may be indicated by decreased levels of VEGFR2 homodimers and heterodimers, and optionally decreased levels of phosphorylated VEGFR. As a surrogate marker of angiogenesis, inhibition of activation of endothelial cells in the patient indicates that the patient has likely responded to treatment of an anti-angiogenic agent.

In yet another aspect of the invention, a method is provided for determining whether a patient has developed resistance to treatment of an anti-angiogenic agent. The method comprises: providing a test sample comprising endothelial cells from the patient who has been treated with an anti-angiogenic agent; measuring level of a protein complex in the endothelial cells from the test sample, wherein the protein complex is formed between a first cellular component and a second cellular component that are cellular components in an angiogenesis signaling pathway; and comparing the level of the protein complex relative to a reference level of the protein complex in the endothelial cells in the patient prior to treatment, wherein a increased level of the protein complex in the endothelial cells from the test sample indicates that the patient has likely developed resistance to the treatment of the anti-angiogenic agent. For example, a test sample containing CEC or CECP isolated from peripheral blood of the patient (or a test sample containing tumor endothelium of the patient) can be analyzed for activation of endothelial cells which may be indicated by decreased levels of VEGFR2 homodimers and heterodimers, and optionally decreased levels of phosphorylated VEGFR. As a surrogate marker of angiogenesis, activation of endothelial cells in the patient indicates that the patient has likely developed resistance to treatment of an anti-angiogenic agent.

In yet another aspect of the invention, a method is provided for detecting activation of endothelial cells. The method comprises: providing a test sample comprising endothelial cells; measuring in the test sample levels of two or more different cellular components that participate in one or more angiogenesis signaling pathways, and comparing the levels of the two or more different cellular components with reference levels of the two or more different cellular components, wherein a difference in the levels of the two or more different cellular components indicates the disease status of the patient. Cellular components that participate in one or more angiogenesis signaling pathways include, but are not limited to, surface adhesion molecules, procoagulant factors, endothelins, growth factor receptors, nitric oxide, endothelial nitric oxide synthase (eNOS), inducible nitric oxide synthase (iNOS), prostaglandins 12 (PGI2), tissue factors, heme oxygenase (HO), such as HO-1, tissue plasminogen activator (tPA), mitochondria superoxide dismutase (MnSOD), Cu/Zn superoxide dismutase (Cu/Zn SOD), tumor growth factor-beta (TGF-β), cyclooxygenase 1 (COX-1), cyclooxygenase-2 (COX-2), vascular cell adhesion molecule (VCAM), such as VCAM-1, intercellular adhesion molecule (ICAM), such as ICAM-1, vascular endothelial growth factor (VEGF), VEGF receptor, E-selectin, and P-selectin. For example, indication of activation of endothelial cells can include one or more of the following: production of endothelin, decrease in nitric oxide (NO), decrease in tissue plasminogen activator, thrombomodulin, PGI2, release of von Willebrand factor, increase in VCAM-1, E-selectin, and plasminogen activator inhibitor-1. More examples of such angiogenic cellular components are described in detail in the following section entitled "Examples of Cellular Components and Protein Complexes in Angiogenesis Signaling Pathways." Preferably, the levels of multiple cellular components are efficiently measured by assays using releasable molecular tags.

According to the present invention, angiogenesis of an organism, preferably a human, can be assessed by directly measuring activation of endothelial cells. The status of activation of endothelial cells can be determined by measuring multiple cellular components, and/or one or more protein complex in a sample containing endothelial cells. The status of activation of endothelial cells can be determined at a given time point, and correlated with future events, e.g., thereby predicting the likelihood of developing a disease associated with undesirable angiogenesis, presence or absence of the disease, prognosis of the disease and the likelihood of response or resistance to a particular therapeutic regimen. The term "therapeutic regimen", as used herein, refers to treatments aimed at the elimination or amelioration of symptoms and events associated with conditions of a disease, in particular, a disease associated with undesirable angiogenesis. In addition to pharmaceutical interventions, such treatments can include without limitation one or more of alteration in diet, lifestyle, and exercise regimen; invasive and noninvasive surgical techniques; and radiotherapy. Pharmaceutical interventions can include administration of a therapeutic agent, such as an antiangiogenic agent. Specific examples of such an antiangiogenic agent are described in detail in the following section entitled "Examples of Antiangiogenic Agents."

Any of the above methods may further comprise the step of treating the individual or patient with a pharmaceutically effective amount of a therapeutic agent, preferably an anti-angiogenic agent. The pharmaceutically effective amount of a therapeutic agent depends on several factors such as, the age, weight, and the severity of the condition under treatment, as well as the route of administration, dosage form and regimen and the desired result, and additionally the potency of the particular therapeutic agent employed in the composition. In addition, account should be taken of the recommended maximum daily dosages for the therapeutic agent. A unit dosage formulation such as a tablet or capsule, will usually contain, for example, from 0.1 mg to 500 mg of an antiangiogenic agent. Preferably, a unit dose formulation will contain 0.1 to 100 mg of an antiangiogenic agent. The antiangiogenic agent may be administered to the patient up to six times daily, conveniently 1 to 4 times daily and preferably 1 to 2 times daily, so that a dose of the antiangiogenic agent in the general range of 0.01 to 100 mg/kg, preferably 0.1 to 10 mg/kg, more preferably 0.1 to 5 mg/kg, is administered daily. A therapeutically effective amount of the therapeutic agent for treating the disease can be administered prior to, concurrently with, or after the onset of the disease or symptom.

The following is a detailed description of various aspects of the invention, including preferred embodiments, as well as examples of various elements of the inventions.

1. Examples of Cellular Components and Protein Complexes in Angiogenesis Signaling Pathways The protein complexes or protein-protein interactions play very important structural and functional roles in almost all biological processes. For example, cell surface receptor-mediated signal transduction, nuclear receptor-mediated signaling events, transcription, translation, post-translational modification, and protein secretion, all require protein-protein interaction, either transient, or stable interaction. Protein interaction can be receptor-receptor interaction, receptor-ligand interaction, receptor-adaptor protein interaction, non-receptor protein kinase-kinase interaction, or kinase-adaptor protein interaction. Protein complexes referred here can be those formed in different cell types or tissues, such as endothelial cells and pericytes, which triggers the diverse array of molecular interaction and signaling leading to angiogenesis.

Several families of receptor tyrosine kinases (RTKS) have emerged as critical mediators of angiogenesis: vascular endothelial growth factor (VEGF), fibroblast growth factor (FGF), PDGF (platelet-derived growth factor), Tie, and Ehp RTK families (Gale, et al. Genes Dev. 1999 13:1055-1066; Yancopoulos, et al. Nature 2000 407:242-248). They are potent angiogenic factors, functioning via their cognate receptors, during embryogenesis and tumorogenesis.

Vascular endothelial growth factor is a potent, multifunctional, endothelial cell specific growth factor. It stimulates proliferation and migration of endothelial cells and is regarded as a key contributor to the growth of cancer and vascular diseases. VEGF activities are mediated by high affinity receptor tyrosine kinases VEGFR1 (Flt-1) and VEGFR2 (KDR or Flk-1), and they are mainly expressed on endothelial cells (F), as well as, for example, on stroma cells or tumor cells, see e.g., U.S. patent Pub. No. 2004/0229293, filed Mar. 30, 2004, the contents of which is incorporated by reference in its entirety; Neuchrist et al., 2001, Laryngoscope, 111 (10): 1834-41, the contents of which is incorporated by reference in its entirety. Recent studies have found a third VEGF receptor, neuropilin (NRP-1), expressed by endothelial cells and tumor cells (Soker, et al. Cell 1998 92:735-745). Induction of NRP-1 expression in tumor cells in vivo resulted in larger and more vascular tumors (Soker, et al. J. Biol. Chem 1996 271:5761-5767; Miao, et al. FASEB J. 2000 14:2532-2539).

The receptor tyrosine kinases Tie-1 and Tie-2, predominantly expressed on endothelial cells, have also been shown to be essential for developmental vascularization where they promote microvessel maturation and stability (Tallquist, et al. Oncogene, 1999 18:7917-7932). Several ligands, designated the angiopoietins, have been identified for Tie-2 (Davis, et al. Cell 1996 87:1161-1169; Kim, et al. FEBS Lett, 1999 443: 353-356; Maisonpierre, et al. Science 1997 277: 55-60; Mezquita, et al. Biochem. Biophys Res Commun 1999 260: 492-298; Valenzuela, et al. Proc. Natl, Acad, Sci. USA 1999 96:1904-1909). Angiopoietin-1 (Ang-1) (Tallquist, et al. Oncogene, 1999 18:7917-7932) and angiopoietin-2 (Ang-2) are the best characterized of the ligands. Binding of Ang-1 induces tyrosine phosphorylation of Tie-2 and activation of its signaling pathway, whereas Ang-2 has been reported to antagonize these effects in endothelia cells (Davis, et al. Cell 1996 87:1161-1169; Maisonpierre, et al. Science 1997 277: 55-60).

The Eph family of RTKs and their ligands (EphB and EphA) are also ritical regulators for vascular development. For example, the expression of ephrinA1 and its receptor EphA2 was detected in breast cancers and associated vasculature (Ogawa, et al. Oncogene 2000 19:6043-6052). Moreover, blocking EphA receptor activation impaired tumor angiogenesis (Brantley, et al. Oncogene 2003 21:7011-7026). Chang, et al. had provided evidence that Eph RTKs and their ligands are necessary for induction of maximal angiogenesis by VEGF. Furthermore it was revealed that ephrinA1 is a downstream target gene product that is induced by VEGF (Cheng, et al. Mol. Cancer Res 2002 1:2-11).

Fibroblast growth factors (FGFs) form a large family of structurally related, multifunctional proteins that regulates an array of biological processes. Like VEGF, stimulates survival, proliferation, migration and differentiation of primary and stable endothelial cells. Dimeric FGF-2 binds to two FGF receptors in the presence of heparin or heparin sulfate, which leads to receptor dimerization and intermolecular autophosphorylation (DiGabriele, et al. Nature 1998 393:812-817).

PDGFs and their cognate tyrosine kinase alpha- and beta-receptors also involved in multiple tumor-associated processes including autocrine growth stimulation of tumor cells, recruitment and regulation of tumor fibroblasts, and stimulation of tumor angiogenesis. PDGF receptor signaling has been implicated in tumor pericyte recruitment. The interaction between endothelial cells and pericytes plays a critical role in stabilizing blood vessels (particularly the newly formed vessels), endothelial cell proliferation and survival (Erber, et al. FASEB J. 2004 18:338-340). PDGF receptors in the tumor stroma have also been shown to function as regulators of tumor interstitial fluid pressure (Pietra, et al. Cancer Res. 2001 61:2929-2934).

It is well established that the binding of these ligand typically results their receptor dimerization and initiates the downstream signal transduction event, mainly through the phosphorylation of specific tyrosine residues within the intracellular domain of the receptor.

Many intracellular signaling proteins are activated directly through receptor binding, such as Crk and PLC-r (phospholipase C-r), in the case of FGFR-mediated signaling, to activate MAPK (mitogen-activated protein kinase), JNK kinases and to mediate Ca2++ release and DAG generation, respectively. Some direct protein-protein interactions have also been identified in VEGFR-1-mediated signaling. For example, tyrosine residues 1213 and 1333 of VEGFR-1 have been shown to interact with several signaling molecules, based on their SH2-domain-binding specificity. In VEGFR-2, Sck (Shc-like protein), PLC-r and VRAP (VEGF receptor-associated protein) directly interact with the receptor (Cross, et al. 2001 Trends in Pharmacological Sci. 22:201-207).

Some proteins might interact with the receptor via indirect mechanisms, or the direct binding (or binding sites) is yet to be identified. In FGFR triggered signaling, Crk might transduce its signal through the complex of FRS-2, Shp-1, Grb2 and Sos before it relayed to Ras, Raf, MEK and MAPK pathway. Grb2 has been postulated to interact with Shc along with Sos, which would ultimately modulate MAPK pathway (Cross, et al. 2001 Trends in Pharmacological Sci. 22:201-207). Shc and Grb14 have been implicated in FGFR-1 activation by cascading signaling to p42/44 MAPK leading to proliferation. PI3K might also participate in FGF signaling as a downstream molecule of PLC-r. In VEGFR-2, many intracellular signaling proteins, such as Akt, STATs (signal transducers and activators of transcription), FAK (focal adhesion kinase), p38 MAPK, eNOS (endothelia nitric oxide synthase), Src and PI3K (phosphoinositide 3-kinase) are implicated as important downstream signaling molecules in response to activation of VEGFR-2, even though the exact mechanism(s) of the protein complex formation remains to be elucidated (Cross, et al. 2001 Trends in Pharmacological Sci. 22:201-207).

Akt, a serine/threonine kinase, functions intracellularly to integrate upstream signals from receptors (e.g. VEGFRs, HER2/neu, IGFR), and regulate the phosphorylation of its multiple downstream effectors, such as NFkB, mTOR, Forkhead, BAD, GSK-3 and MDM-2. These phosphorylation events in turn can also modulate the effects of Akt on cell growth, proliferation, protection from pro-apoptotic stimuli, and stimulation of angiogenesis (Mitsiades, et al. Curr Cancer Drug Targets, 2004 4:235-256).

STAT is another critical pathway downstream of VEGFRs. It has been shown that dominant-negative STAT3 completely abolished VEGF-induced nuclear translocation of phosphorylated STAT3 and inhibited endothelial migration in vitro (Yahata, et al. J. Biolo. Chem. 2003 278:40026-40031), which demonstrated the role of phosphorylated STAT3 in VEGF-triggered signaling pathways. Most recent studies have provided in vivo evidence, which indicated that the expression of phosphorylated STAT3 and STAT5, but not phosphorylated STAT1 or STAT6, were observed to be elevated only in ovarian epithelial carcinoma. Normal ovarian tissues, or benign ovarian tumors expressed significantly lower levels of phosphorylated STAT3 and STAT5. The over expression of phosphorylated STAT3 and STAT5 appeared to correlate with the activation of VEGFR (Chen, et al. Gynecol. Oncol. 2004 94:630-635).

The essential roles of protein-protein interaction extend beyond the cell surface receptor-ligand interaction and its triggered intracellular pathways. Though the key receptors, their ligands (e.g. growth factors) and the related networks formed by the intracellular kinases and proteins play the central roles in signal transduction leading to pro-angiogenesis, the extracellular matrix components and other molecules are also indispensable part of the angiogenesis processes in vivo. Indeed, several extracellular molecules have been shown to possess unique anti-angiogenic function (Fotsis, et al. Nature 368:237-239; Polakowski, et al. Am J. Pathol. 1993 143-507-517). The mechanisms of action of most of these molecules are poorly defined, nonetheless, some of these angiogenesis inhibitors were found to be either heparin analogs or heparin binding substances (Taylor, et al. Nature, 1982 297:307-312; Jouan, et al. Blood 1999 94:984-993). Heparins are linear anionic polysaccharide chains, and they are typically heterogeneously sulphated on alternating L-iduronic and D-glusocamino sugars. They are nearly ubiquitous in animal tissues as heparin sulphate proteoglycans on cell surfaces and in the extracellular matrix (DiGabriele, et al. Nature 1998 393:812-817).

Heparin sulphate can bind to the various forms of VEGFAs, for example, to modulate the affinity of VEGFAs to its receptor. In fact the binding of VEGF165 to its receptors requires cell surface heparin sulfates and the binding can be regulated by exogenous heparin (Gitay-Goren, et al. J. Biol. Chem. 1992 267:6093-6098). These observations together with the recent results showing that heparin-degrading enzymes can inhibit the tumor angiogenesis (Sasisekharan, et al. Proc. Natl. Acad. Sci. USA, 1994 91, 1524-1528) suggest that heparin sulfates may play an important regulatory role in the angiogenesis processes. The requirement for heparin-like molecule to modulate receptor-ligand binding is not unique for VEGFA/VEGFR interaction, as it has been well-studied that FGF binding to FGFR and the activation of the receptor also requires heparin-like molecules (Spivak-Kroizman, et al. Cell 1994 79:1015-1024).

In some embodiments of the present invention, the cellular components participating in angiogenesis pathways include receptors for angiogenic growth factors. As described above, these receptors belong to the family of the receptor tyrosine kinase and are intimately involved in tumor development and metastasis. Example of the receptor tyrosine kinase include, but are not limited to, receptor for fibrin (VE-cadherin), receptors for VEGF (Flt1 and KDR/flk-1), receptor for VEGF-C and VEGF-D (Flt4), receptor for VEGF-165 (NP-1 and NP-2), receptors for angiopoeitin-1, -2, -3, and -4 (Tie 1 and Tie 2), receptors for FGF (FGF-R1, -R2, -R3 and -R4), receptor for PDGF (PDGF-R), receptor for ephrine A1-5 (Eph A1-8), and receptor for ephrine B1-5 (Eph B1-8).

The cellular components participating in angiogenesis pathways also include receptors for anti-angiogenic protein factors. Examples of such receptors include, but are not limited to, receptor for angiostatin (angiostatin-R, also called Annexin II), receptor for angiostadin (angiostadin binding protein I), low-affinity receptors for glypicans, receptor for endostatin (endostatin-R), the receptor for endothelin-1 (endothelin-A receptor), receptor for angiocidin (angiocidin-R), the receptor angiogenin (angiogenin-R), receptors for thromospondin-1 and thromospondin-2 (CD36 and CD47), and the receptor for tumstatin (tumstatin-R).

The cellular components participating in angiogenesis pathways also include G protein coupled receptors (GPCR). Examples of such GPCR include, but are not limited to, receptor for sphingosie-1-phosphate or SPP and for lysophosphatidic acid or LSA (edg receptor), cytokine receptors such as receptor for tumor necrosis factor-α or TNF-α (TNF-α receptor) and receptor for interleukin-8 or IL-8 (IL-8 receptor), protease receptors such as receptor for urokinase (urokinase receptor), and integrins such as receptor for thromospondin-1 and -2 ($\alpha v \beta 3$ integrin and $\alpha 2 v \beta 1$ integrin) and receptor for fibronectin ($\alpha v \beta 3$ integrin), and matrix metalloproteases.

Various protein complexes formed by the cellular components in endothelial cells play important roles in activation of endothelial cells, leading to angiogenesis. For example, in response to the release of VEGF by the tumor mass, angiogenesis is stimulated in adjacent endothelial cells via formation of protein complexes of receptors for VEGF. Normally, capillary endothelial cells turn over extremely slowly (thousands of days) and are kept quiescent through contact with specialized cells, called pericytes. When VEGF is expressed by the tumor mass, endothelial cells closely adjacent to the VEGF+ tumor cells will up-regulate expression of VEGF receptor (VEGFR) molecules KDR/flk-1 and/or flt-1. Upon binding of their ligand, these receptors dimerize and transduce an intracellular signal through tyrosine phosphorylation. Binding of VEGF to its cognate VEGF receptors on endothelial cells initiates a chemotaxic effect in these cells through signal transduction. New capillaries sprout from the endothelial vessels towards the VEGF+ tumor cells. During angiogenesis, the endothelial cells rapidly proliferate by dividing up to every five days. Thus, by measuring formation of protein complexes of VEGFR and/or other cellular components in the VEGF-dependent angiogenic signaling pathway, activation of endothelial cells can be detected in a pathway-specific manner.

The Tie receptors for angiopoietin also play important roles in stimulation of angiogenesis. The Tie receptors, Tie-1 and Tie-2 (Tie stands for Tyrosine kinase receptors with immunoglobulin and EGF homology domains), are among many receptor tyrosine kinases (RTK) expressed on endothelial cells. Mustonen (1995) J. Cell. Biol. 129:895). Angiopoietin-1 (Ang-1) is the major physiological ligand for Tie-2 which is responsible for recruiting and sustaining periendothelial support cells (Davis et al. (1996) Cell 87:1161-1169). Angiopoietin-2 (Ang-2) is found to be responsible in disrupting vessel formation in the developing embryo by antagonizing the effects of Ang-1 and Tie 2. Tie 1 and Tie 2 are homologous to each other, but unlike the VEGF receptors, they contain matrix association motifs in their extracellular domains. Both are expressed very early in development (Dumont et al. (1995) Dev. Dyn. 203:80-92). Tie-2 is expressed in the blood islands and in intraembryonic angioblasts, where it appears earlier than von Willebrand factor. The Tie 1 and Tie 2 receptors are single-transmembrane, tyrosine kinase receptors. They are the only receptor tyrosine kinases, other than those receptors for VEGF, that are largely restricted to endothelial cells in their expression.

The Tie receptors are proteins of approximately 125 kDa, with a single putative transmembrane region. The extracellular domain of these receptors is uniquely divided into three regions that have a pattern of cysteine expression found in EGF-like domains; two regions that have some weak homology to and structural characteristics of immunoglobulin-like domains; and three regions with homology to the fibronectin III repeat structure. The intracellular portion of Tie 2 is most closely related (~40% identity) to the kinase domains of FGF-R1, PDGF-R and c-kit. The intracellular portions of Tie 2 contain all of the features of tyrosine kinases. It is well established that Tie 2 and its ligand Ang1 play crucial roles in the maturation of blood vessels in healthy angiogenesis by inducing endothelial cells to recruit and incorporate pericytes and smooth muscle cells into the vessel wall, and remodeling and stabilizing the immature network of blood vessels formed under the effect of VEGF. Herbst et al. (2002) Hematol. Oncol. Clin. N. Am. 16:1125-1171.

In some embodiments of the present invention, the cellular components and protein complexes participating in angiogenesis signaling pathways include, but are not limited to, 1) VEGFR-1, 2, 3 homodimers and heterodimers (Ferrara (2004) Endocrine Reviews 25 (4):581-611);

2) phosphorylated VEGFR-1, 2, 3 (Ferrara (2004), supra);

3) VEGFR-2/Nrp-1, VEGFR-2/Nrp-2 heterodimers (Ferrara (2004), supra; and Herbst et al. (2002); Neuropilin-1 forms a ternary complex with VEGFR-2 and VEGF and potentiates the effects of VEGF);

4) VEGFR-2/heparin sulphate complex (Nicosia (1998) Am. J. Pathol. 153:11-16; Heparin binds to certain isoforms of VEGF with a higher affinity than other isoforms and sequesters VEGF to the extracellular matrix);

5) VEGFR-2/VE-cadherin complex;

6) Tie 1/Tie 2 heterodimer (Brindle et al. (2000) J. Biol. Chem. 275: 39741-39746);

7) Tie 1 endodomain/Tie 2 heterodimer (Brindle et al. (2000), supra);

8) VEGF/PIGF heterodimer (Ferrara (2004), supra);

9) PDGFR homo and heterodimers (Hanahan et al. (2003) J. Clin. Invest. 111:1287-1295; PDGFR signaling is critical for pericyte-endothelial association (vessel maturation) in tumors);

10) EphA-1, 2, 3, 4, 5, 6, 7, 8, 10, EphB-1, 2, 3, 4, 6 homo and heterodimers (Chen et al. (2002) Mol. Cancer Res. 1:2-11; and Herbst et al. (2002), supra; Ephrins must be tethered to membranes to activate their receptors (Ephs); Ephrins are involved in adult and developmental sprouting angiogenesis, juxtacrine cell-to-cell contacts, adhesion to extracellular matrix, and migration; and Eph receptors are overexpressed in many types of tumor cells and tumor-associated endothelial cell);

11) FLT3 dimers;

12) FGFR-1, 2, 3, 4 homo and heterodimers (Claesson-Welsh et al. (2001) TRENDS in Pharm Sci, Vol. 22 No. 4: 201-207; Herbst et al. (2002), supra; FGFs are potent angiogenic molecules and stimulate endothelial cell mitosis, migration, morphogenesis, and survival);

13) Stat3 complexes and phosphorylated Stat3

14) BAD complexes and phosphorylated BAD (Zachary (2003) Biochemical Society Transactions 31:1171-1177);

15) Rsk complexes and phosphorylated Rsk;

16) PI3K complexes and phosphorylated PI3K (Rahimi et al. (2001) J. Biol. Chem. 276:17686-17692);

17) Fak complexes and phosphorylated Fak (Claesson-Welsh et al. (2004). J. Biol. Chem. Mar. 16, 2004);

18) Src complexes and phosphorylated Src (Fujita et al. (2002) BMC Biochemistry 3:32);

19) P70S6K complexes and phosphorylated P70S6K;

20) SHC complexes and phosphorylation (Park et al. (2004) Proc. Natl. Acad. Sci. 101:2345-2350);

21) Stat1 complexes and phosphorylated Stat1;

22) Stat5 complexes and phosphorylated Stat5;

23) Akt complexes and phosphorylated Akt (Ferrara (2004), supra);

24) Erk complexes and phosphorylated Erk (Ferrara (2004), supra);

25) Jnk complexes and phosphorylated Jnk (Zachary (2003), supra);

26) P38 complexes and phosphorylated P38 (Zachary (2003), supra);

27) MEK complexes and phosphorylated MEK (Ferrara (2004), supra);

28) PLC-γ complexes and phosphorylated PLC-γ (Shibuya et al. (2001). "A single autophosphorylation site on KDR/Flk-1 is essential for VEGF-A-dependent activation of PLC-γ and DNA synthesis in vascular endothelial cells");

29) Shb complexes and phosphorylated Shb (Claesson-Welsh et al. (2004), supra); and 30) Her-1, 2, 3, 4 homodimers and heterodimers.

It is noted that such cellular components or protein complexes can be detected by the methods of the present invention on any cells that contribute to or promote angiogenesis, including, e.g., endothelial cells, stroma cells or tumor cells. While detection on endothelial cells is exemplified throughout, it should be well understood by the skilled artisan that the methods of the present invention can be applied to any cells suspected of contributing to or promote angiogenesis, e.g., stroma cells or tumor cells.

In addition, the cellular components participating in angiogenesis signaling pathways also include secreted angiogenic factors and intercellular adhesion molecules. Studies have revealed that activation of endothelial cells increase the expression of surface adhesion molecules, express and release procoagulant factors, and secrete vasoactive compounds including endothelins, nitric oxide, and prostaglandins. All of these substances have been implicated in the pathophysiology of a variety of diseases (Corti et al. "Endothelial dysfunction and hypertension" In: Vascular Endothelium in Human Physiology and Pathophysiology, edited by Vallance P. J. T. and Webb D. J. Amsterdam: Harwood, 2000, pp. 109-128; Goligorsky et al. (2001) Hypertension 37:744-874; Haller (1997) Drugs 53:1-10; Naicker et al. (2001) Pharmacol Ther. 90:61-88; Smith et al. (1993) Physiol Pharmacol. 71:76-87; Vapaatalo et al. (2001) Med Sci Monit. 7:1075-1085). Specific examples of the cellular components include surface adhesion molecules, procoagulant factors, endothelins, growth factor receptors, nitric oxide, eNOS, iNOS, PGI2, tissue factors, heme oxygenase (HO), such as HO-1, tPA, MnSOD, Cu/Zn SOD, TGF-β, COX-1, COX-2, VCAM, such as VCAM-1, ICAM, such as ICAM-1, VEGF, E-selectin, and P-selectin.

2. Preparation of Samples

Samples containing cellular components of endothelial cells may come from a wide variety of sources for use with the present invention, including cell cultures, animal or plant tissues, patient biopsies, patient blood, bodily fluid, and the like. Preferably, samples are from humans. Samples are prepared for assays of the invention using conventional techniques, which may depend on the source from which a sample is taken.

1) Isolation of Circulating Endothelial Cells and Circulating Endothelial Cell Progenitors Circulating endothelial cells (CEC) and circulating endothelial cell progenitors (CECP) have been used as surrogate markers of tumor angiogenesis. Mancuso et al. (2001) Blood 97:3658-3661; and Monestiroli et al. (2001) Cancer Res. 4341-4344. According to the present invention, multiple cellular components and their interactions in CEC and CECP are analyzed to provide information for assessing angiogenesis, monitoring disease status, predicting treatment response, etc.

CEC and CECP can be isolated from blood specimens by using various techniques available in the art. Blood specimens can be obtained using methods of sampling known in the art, such as venipuncture. Venous blood can be drawn into vessels, such as tubes, and optionally treated with silicon and EDTA for subsequent analysis. As used herein, the terms "blood sample" and "blood specimen" are used interchangeably to refer to a volume of blood that is preferably, although not necessarily, removed from the patient's peripheral circulatory system.

The blood specimen may be obtained by isolating a volume of blood from the bloodstream. however, other means for sampling the patient's blood can be utilized, such as in-dwelling systems. For example, an in-dwelling catheter can be utilized to remove a volume of blood.

The blood specimen is treated to remove lower molecular weight contaminants, for example, by dialysis. Spectra/Por membrane dialysis tubing with a desired molecular weight cut-off (MWCO) can be utilized. Other products that can be utilized include hollow fiber concentration systems consisting of regenerated cellulose fibers for larger volumes; a multiple dialyzer apparatus with a sample size for one to five milliliters; and a multiple microdialyzer apparatus, convenient for samples in plates with 96 wells, for example. Other equivalent techniques include passage through a column holding a resin or mixture of resins suitable for removal of low molecular weight materials. Resins such as BIOGEL (BIORAD, Hercules, Calif.) and SEPHAROSE (PHARMACIA, Piscataway, N.J.) and others are well-known to the skilled artisan. The technique of dialysis, or equivalent techniques with the same function, are intended to remove low molecular weight contaminants from the blood specimen.

Specific antibodies (e.g., polyclonal or monoclonal antibodies) raised to a particular cellular component of CEC or CECP, such as VEGFR, can be used to isolate CEC or CECP in blood specimens. The term "antibody" as used herein, includes monoclonal and polyclonal antibodies as well as antibody fragments which bind specifically but reversibly to the described epitope. It is preferred that the antibody or antibody fragment is derived from a monoclonal antibody or antibody fragment. Preparation of monoclonal and polyclonal antibodies to an antigen representing an endothelial cell activation marker can be achieved using any known method, and for example, those described in Zola, H. (1988) "Monoclonal Antibodies—A manual of techniques" CRC Press, and Antibodies: A Laboratory Manual, Harlow & Lane; Cold Spring Harbor (1988), incorporated herein by reference. Specific high affinity binding proteins can be used in place of antibodies, and can be made according to methods known to those in the art. For example, proteins that bind specific DNA sequences may be engineered (U.S. Pat. No. 5,096,815), and proteins that bind a variety of other targets, particularly protein targets (U.S. Pat. No. 5,233,409; U.S. Pat. No. 5,403,484) can be engineered and used in the present invention. Antibodies and/or binding proteins can be incorporated into large scale diagnostic or assay protocols that can involve immobilization of the antibody or binding protein onto a surface, such as a multi-well plate assay, or on beads, for example.

General techniques to be used in performing various immunoassays are known to those of ordinary skill in the art. General descriptions of these procedures are provided in manuals of the art (Ishikawa, E. et al., (1988) Enzyme Immunoassay, Igaku-shoin, Tokyo, N. Y.; Hallow, E. et al., Antibodies: A Laboratory Manual, CSH Press, N.Y.).

In a preferred embodiment, CEC and/or CECP are isolated by immunomagnetic isolation or enrichment involving monoclonal antibodies against a CEC or CECP cellular component coupled to magnetic beads. Immunomagnetic isolation or enrichment may be carried out using a variety of techniques and materials known in the art, as disclosed in the following representative references that are incorporated by reference: Terstappen et al., U.S. Pat. No. 6,365,362; Terstappen et al., U.S. Pat. No. 5,646,001; Rohr et al., U.S. Pat. No. 5,998,224; Kausch et al., U.S. Pat. No. 5,665,582; Kresse et al., U.S. Pat. No. 6,048,515; Kausch et al., U.S. Pat. No. 5,508,164; Miltenyi et al., U.S. Pat. No. 5,691,208; Molday, U.S. Pat. No. 4,452,773; Kronick, U.S. Pat. No. 4,375,407; Radbruch et al., chapter 23, in Methods in Cell Biology, Vol, 42 (Academic Press, New York, 1994); Uhlen et al., Advances in Biomagnetic Separation (Eaton Publishing, Natick, 1994); Safarik et al., J. Chromatography B, 722: 33-53 (1999); Miltenyi et al., Cytometry, 11: 231-238 (1990); Nakamura et al., Biotechnol. Prog., 17: 1145-1155 (2001); Moreno et al., Urology, 58: 386-392 (2001); Racila et al., Proc. Natl. Acad. Sci., 95: 4589-4594 (1998); Zigeuner et al., J. Urology, 169: 701-705 (2003); Ghossein et al., Seminars in Surgical Oncology, 20: 304-311 (2001).

The preferred magnetic particles for use in carrying out this invention are particles that behave as colloids. Such particles are characterized by their sub-micron particle size, which is generally less than or about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool.

Magnetic particles having the above-described properties can be prepared by modification of base materials described in U.S. Pat. Nos. 4,795,698, 5,597,531 and 5,698,271, all of which patents are incorporated by reference.

In a particular embodiment, substantially pure CEC and CECP are isolated by using the immunomagnetic isolation/enrichment technique described in Kinzler et al. (2000) Science 289:1197-1202, which is herein incorporated by reference. Briefly, the epithelial and hematopoietic cell fractions in the peripheral blood samples are sequentially removed via negative selection via antibody-linked magnetic beads (Ber-EP4 beads-Epithelial, CD45 beads-Pan leukocyte, CD64 beads-Macrophages, and CD14 beads-Monocytes, CD 146 beads-endothelial cells). The remaining cells are stained with P1H12 antibodies (need to provide info on P1P12 antibody) and are isolated via positive selection with magnetic beads.

2) Preparation of Samples Containing Endothelium

Also according to the present invention, multiple cellular components and their interactions in endothelial cells in endothelium (e.g., tumor endothelium) are analyzed to provide information for assessing angiogenesis, monitoring disease status and predicting treatment response.

The endothelium is located at the interface between the blood and the vessel wall, and is composed of endothelial cells. Each endothelial cell is anchored to an underlying basal lamina; and individuals cells are anchored together by adhesion junctions. The tissue samples containing endothelium can be prepared from biopsy and medical specimen of any type of tissue containing blood vessels, the guidance for which is provided in the following references: Bancroft J D & Stevens A, eds. Theory and Practice of Histological Techniques (Churchill Livingstone, Edinburgh, 1977); Pearse, Histochemistry. Theory and applied. $4^{th}$ ed. (Churchill Livingstone, Edinburgh, 1980).

Examples of tissue samples that contain endothelium include, but are not limited to, breast, prostate, ovary, colon, lung, endometrium, stomach, salivary gland or pancreas. The tissue sample can be obtained by a variety of procedures including, but not limited to surgical excision, aspiration or biopsy. The tissue may be fresh or frozen. In one embodiment, assays of the invention are carried out on tissue samples that have been fixed and embedded in paraffin or the like; therefore, in such embodiments a step of deparaffination is carried out. A tissue sample may be fixed (i.e. preserved) by conventional methodology [See e.g., "Manual of Histological Staining Method of the Armed Forces Institute of Pathology," $3^{rd}$ edition (1960) Lee G. Luna, H T (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, a tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may have a thickness in a range from about three microns to about twelve microns, and preferably, a thickness in a range of from about 5 microns to about 10 microns. In one aspect, a section may have an area of from about 10 $mm^2$ to about 1 $cm^2$. Once cut, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De® (CMS, Houston, Tex.) may be used. For mapping tumor endothelium, the sample preparation method described in Schnitzer et al. (2004) Nature 429:629-636 may be used.

3. Assays for Measuring Cellular Components and their Complexes

A variety of assays may be used to detect protein-protein interactions and measure multiple proteins simultaneously.

1) Immunoaffinity-Based Methods

In one embodiment, immunoaffinity-based methods, such as immunoprecipitation or ELISA, is used to detect complexes of cellular components in endothelial cells in a test sample containing CEC, CECP or endothelium. For example, to detect the protein complex formed by VEGFR2 and VE-cadherin, anti-VEGFR2 antibody can be used to immunoprecipitate complexes comprising VEGFR2 from CEC, and the resulting immunoprecipitant is then probed for the presence of VE-cadherin by immunoblotting.

In other embodiments, ELISA or antibody "sandwich"-type assays can be used to detect complexes of cellular components in endothelial cells in a test sample containing CEC, CECP or endothelium. For example, antibodies to VEGFR2 are immobilized on a solid support, contacted with CEC lysate, washed, and then exposed to antibody against VE-cadherin. Binding of the latter antibody, which may be detected directly or by a secondary antibody conjugated to a detectable label, indicates the presence of the complex of VEGFR2 and VE-cadherin in CEC.

2) Cross-Linking Assays

Chemical or UV cross-linking may also be used to covalently join heterodimers on the surface of living cells. Hunter et al., Biochem. J., 320:847-53. Examples of chemical cross-linkers include dithiobis(succinimidyl) propionate (DSP) and 3,3'dithiobis(sulphosuccinim-idyl) propionate (DTSSP). In one embodiment, cell extracts from chemically cross-linked endothelial cells are analyzed by SDS-PAGE and immunoblotted with antibodies to different cellular components. A supershifted band of the appropriate molecular weight most likely represents complex formation. This result may be confirmed by subsequent immunoblotting.

3) Fluorescence Resonance Energy Transfer (FRET)

FRET may also be used to detect complexes of cellular components in endothelial cells in a test sample containing CEC, CECP or endothelium. FRET detects protein conformational changes and protein-protein interactions in vivo and in vitro based on the transfer of energy from a donor fluorophore to an acceptor fluorophore. Selvin, Nat. Struct. Biol., 7:730-34 (2000). Energy transfer takes place only if the donor fluorophore is in sufficient proximity to the acceptor fluorophore. In a typical FRET experiment, two proteins or two sites on a single protein are labeled with different fluorescent probes. One of the probes, the donor probe, is excited to a higher energy state by incident light of a specified wavelength. The donor probe then transmits its energy to the second probe, the acceptor probe, resulting in a reduction in the donor's fluorescence intensity and an increase in the acceptor's fluorescence emission. To measure the extent of energy transfer, the donor's intensity in a sample labeled with donor and acceptor probes is compared with its intensity in a sample labeled with donor probe only. Optionally, acceptor intensity is compared in donor/acceptor and acceptor only samples. Suitable probes are known in the art and include, for example, membrane permeant dyes, such as fluorescein and rhodamine, organic dyes, such as the cyanine dyes, and lanthanide atoms. Selvin, supra. Methods and instrumentation for detecting and measuring energy transfer are also known in the art. Selvin, supra.

FRET-based techniques suitable for detecting and measuring protein-protein interactions in individual cells are also known in the art. For example, donor photobleaching fluorescence resonance energy transfer (pbFRET) microscopy and fluorescence lifetime imaging microscopy (FLIM) may be used to detect the dimerization of cell surface receptors. Selvin, supra; Gadella & Jovin, J. Cell Biol., 129:1543-58 (1995).

For example, antibodies against VEGFR2 and VE-cadherin are directly labeled with two different fluorophores. Endothelial cell lysates are contacted with the differentially labeled antibodies, which act as donors and acceptors for FRET in the presence of VEGFR2 and VE-cadherin heterodimer. Energy transfer is detected and the presence of heterodimers is determined if the labels are found to be in close proximity.

4) Assays Using Releasable Molecular Tags

In some preferred embodiments, assays using releasable molecular tags are used to detect protein-protein interactions, such as protein dimer formation, and measure multiple proteins simultaneously.

Many advantages are provided by measuring dimer populations using releasable molecular tags (such as with eTag™ assays, as described below), including (1) separation of released molecular tags from an assay mixture provides greatly reduced background and a significant gain in sensitivity; and (2) the use of molecular tags that are specially designed for ease of separation and detection provides a convenient multiplexing capability so that multiple receptor complex components may be readily measured simultaneously in the same assay. Assays employing such tags can have a variety of forms and are disclosed in the following references: Singh et al., U.S. Pat. No. 6,627,400; U.S. patent publications Singh et al., 2002/0013126; and 2003/0170915, and Williams et al., 2002/0146726; and Chan-Hui et al., International patent publication WO 2004/011900, all of which are incorporated herein by reference. For example, a wide variety of separation techniques may be employed that can distinguish molecules based on one or more physical, chemical, or optical differences among molecules being separated including but not limited to electrophoretic mobility, molecular weight, shape, solubility, pKa, hydrophobicity, charge, charge/mass ratio, polarity, or the like. In one aspect, molecular tags in a plurality or set differ in electrophoretic mobility and optical detection characteristics and are separated by electrophoresis. In another aspect, molecular tags in a plurality or set may differ in molecular weight, shape, solubility, pKa, hydrophobicity, charge, polarity, and are separated by normal phase or reverse phase HPLC, ion exchange HPLC, capillary electrochromatography, mass spectroscopy, gas phase chromatography, or like technique.

Sets of molecular tags are provided that are separated into distinct bands or peaks by a separation technique after they are released from binding compounds. Identification and quantification of such peaks provides a measure or profile of the kinds and amounts of receptor dimers. Molecular tags within a set may be chemically diverse; however, for convenience, sets of molecular tags are usually chemically related. For example, they may all be peptides, or they may consist of different combinations of the same basic building blocks or monomers, or they may be synthesized using the same basic scaffold with different substituent groups for imparting different separation characteristics, as described more fully below. The number of molecular tags in a plurality may vary depending on several factors including the mode of separation employed, the labels used on the molecular tags for detection, the sensitivity of the binding moieties, the efficiency with which the cleavable linkages are cleaved, and the like. In one aspect, the number of molecular tags in a plurality for measuring populations of receptor dimers is in the range of from 2 to 10. In other aspects, the size of the plurality may be in the range of from 2 to 8, 2 to 6, 2 to 4, or 2 to 3.

Protein dimers (e.g., VEGFR, Tie dimers) may be detected in assays having homogeneous formats or a non-homogeneous, i.e. heterogeneous, format. In a homogeneous format, no step is required to separate binding compounds specifically bound to target complexes from unbound binding compounds. In a preferred embodiment, homogeneous formats employ reagent pairs comprising (i) one or more binding compounds with releasable molecular tags and (ii) at least one cleaving probe that is capable of generating an active species that reacts with and releases molecular tags within an effective proximity of the cleaving probe.

Protein dimers may also be detected by assays employing a heterogeneous format. Heterogeneous techniques normally involve a separation step, where intracellular complexes having binding compounds specifically bound are separated from unbound binding compounds, and optionally, other sample components, such as proteins, membrane fragments, and the like. Separation can be achieved in a variety of ways, such as employing a reagent bound to a solid support that distinguishes between complex-bound and unbound binding compounds. The solid support may be a vessel wall, e.g., microtiter well plate well, capillary, plate, slide, beads, including magnetic beads, liposomes, or the like. The primary characteristics of the solid support are that it (1) permits segregation of the bound and unbound binding compounds and (2) does not interfere with the formation of the binding complex, or the other operations in the determination of receptor dimers. Usually, in fixed samples, unbound binding compounds are removed simply by washing.

With detection using molecular tags in a heterogeneous format, after washing, a sample may be combined with a solvent into which the molecular tags are to be released. Depending on the nature of the cleavable bond and the method of cleavage, the solvent may include any additional reagents for the cleavage. Where reagents for cleavage are not required, the solvent conveniently may be a separation buffer, e.g. an electrophoretic separation medium. For example, where the cleavable linkage is photolabile or cleavable via an active species generated by a photosensitizer, the medium may be irradiated with light of appropriate wavelength to release the molecular tags into the buffer.

In either format, if the assay reaction conditions interfere with the separation technique employed, it may be necessary to remove, or exchange, the assay reaction buffer prior to cleavage and separation of the molecular tags. For example, in some embodiments, assay conditions include salt concentrations (e.g. required for specific binding) that degrade separation performance when molecular tags are separated on the basis of electrophoretic mobility. In such embodiments, an assay buffer is replaced by a separation buffer, or medium, prior to release and separation of the molecular tags.

Assays employing releasable molecular tags and cleaving probes can be made in many different formats and configurations depending on the complexes that are detected or measured. Based on the present disclosure, it is a design choice for one of ordinary skill in the art to select the numbers and specificities of particular binding compounds and cleaving probes.

Figure 4A:
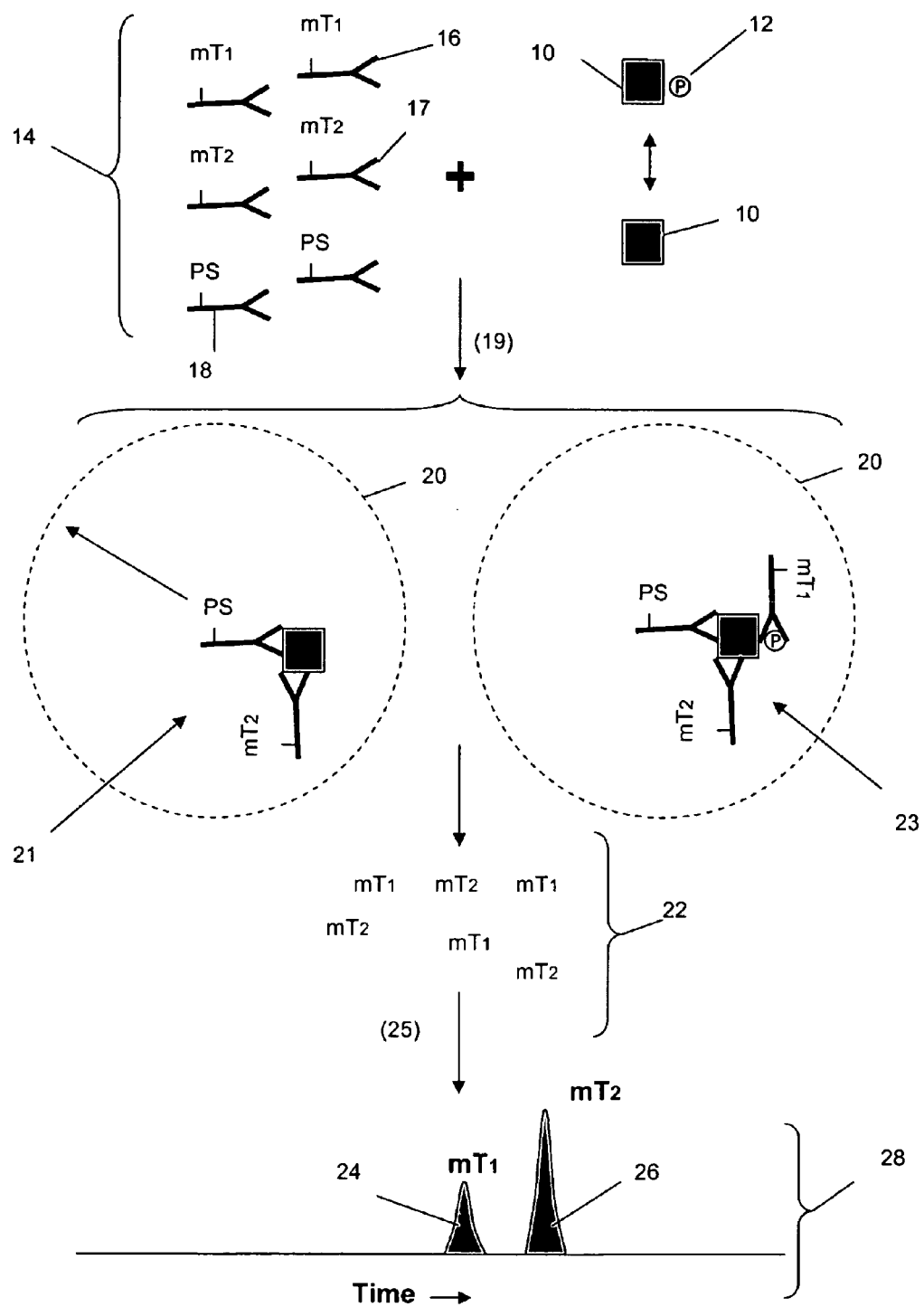
FIGS. 4A-4F illustrate diagrammatically the use of releasable molecular tags to measure receptor dimer populations.

In one aspect of the invention, the use of releasable molecular tags to measure components of signaling pathways is shown diagrammatically in FIGS. 4A-H. The operation of such assays to provide ratiometric measurements is illustrated in FIG. 4A. Effector protein (10) exists in two states in a cell, one having a post-translational modification, e.g. such as a phosphate group (12), and the other not having such a post-translational modification. Reagents (14) of the invention, comprising cleaving probes (18) (in this illustration having photosensitizer "PS" attached) and binding compounds (16 and 17), are mixed (19) with a sample containing both the activated and inactivated forms of effector protein (10) under conditions that permit the specific binding of cleaving probes (18) and binding compounds (16 and 17) to their respective antigenic determinants on the activated and inactivated forms of effector protein (10) resulting in the formation of either complex (21) or complex (23). After binding, and optionally washing or buffer exchange, cleaving probes (18) are activated to generate an active species that, e.g. in the case of singlet oxygen, diffuses out from a photosensitizers to an effective proximity (20). Cleavable linkages within this proximity are cleaved and molecular tags are released (22). Released molecular tags (22) are then separated (25) and a separation profile (28), such as an electropherogram, is produced, in which peak (24) is identified and correlated to molecular tag, "$mT_1$" and peak (26) is identified and correlated to molecular tag, "$mT_2$." In one aspect, a ratiometric measure of activated effector protein (10) is provided as the ratio of areas of peaks (24) and (26).

Figure 4B:
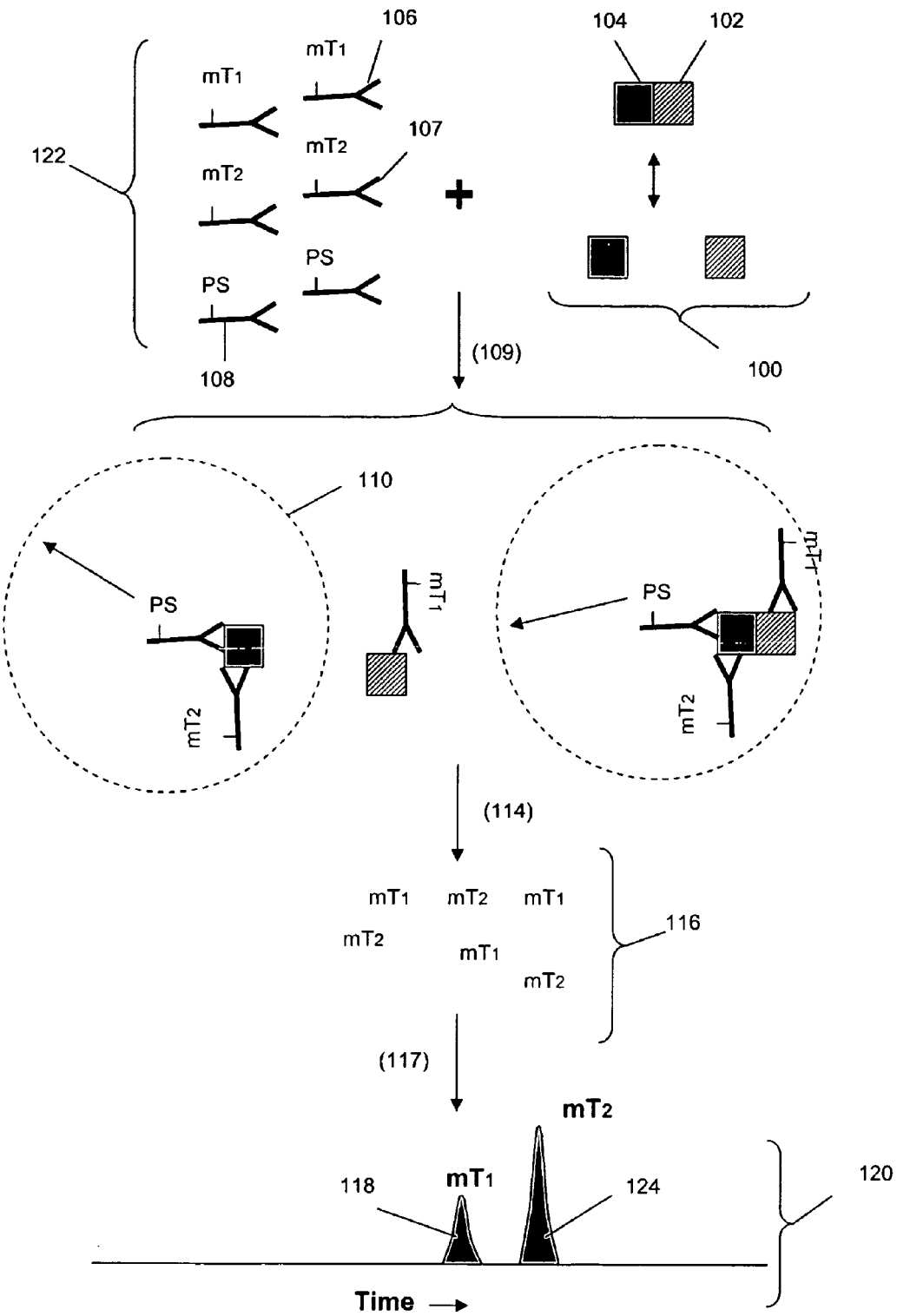

A method of measuring signaling complexes comprising heterodimers is illustrated in FIG. 4B. Signaling complex (100) forms by the binding of proteins (104) and (102), e.g. Akt and PDK 1. Reagents (122) of the invention, comprising cleaving probes (108) (in this illustration having photosensitizer "PS" attached) and binding compounds (106 and 107), are mixed (109) with a sample containing complex (100) under conditions that permit the specific binding (112) of cleaving probes (108) and binding compounds (106 and 107) to their respective antigenic determinants on complex (100) that are on different proteins of the complex. After binding, and optionally washing or buffer exchange, cleaving probes (108) are activated to generate an active species that, e.g. in the case of singlet oxygen, diffuses out from a photosensitizers to an effective proximity (110). Cleavable linkages within this proximity are cleaved and molecular tags are released (114). Released molecular tags (116) are then separated (117) and a separation profile (120), such as an electropherogram, is produced, in which peak (118) is identified and correlated to molecular tag, "$mT_1$" and peak (124) is identified and correlated with molecular tag, "$mT_2$." By employing additional binding compounds and molecular tags, additional complexes may be measured. As with the ratiometric measure of an activated effector protein, the amount of heterodimeric complexes may be provided as a ratio of peak areas. FIG. 4D illustrates the analogous measurements for cell surface receptors that form heterodimers in cell surface membrane (161).

Figure 4C:
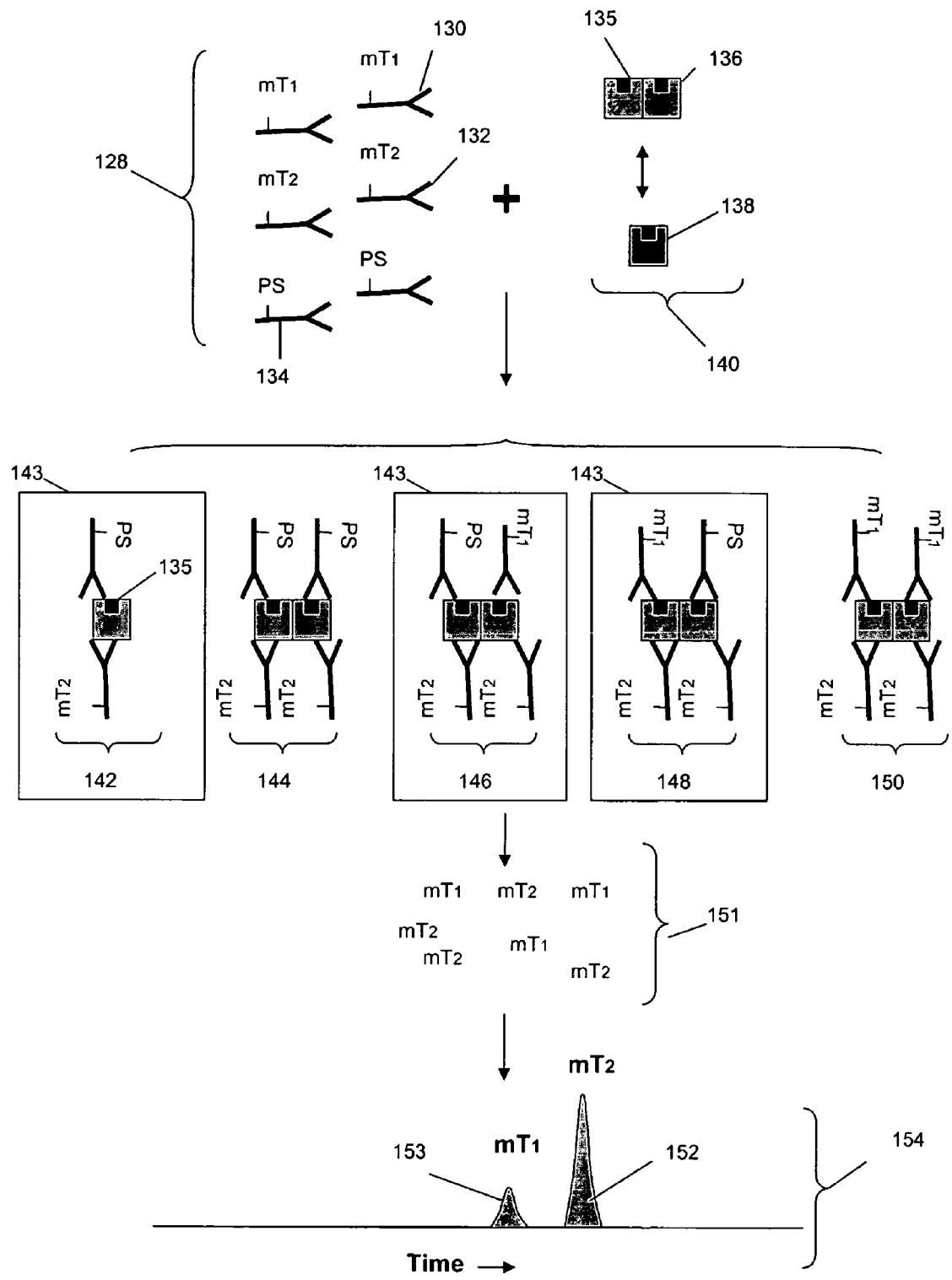
Figure 4D:
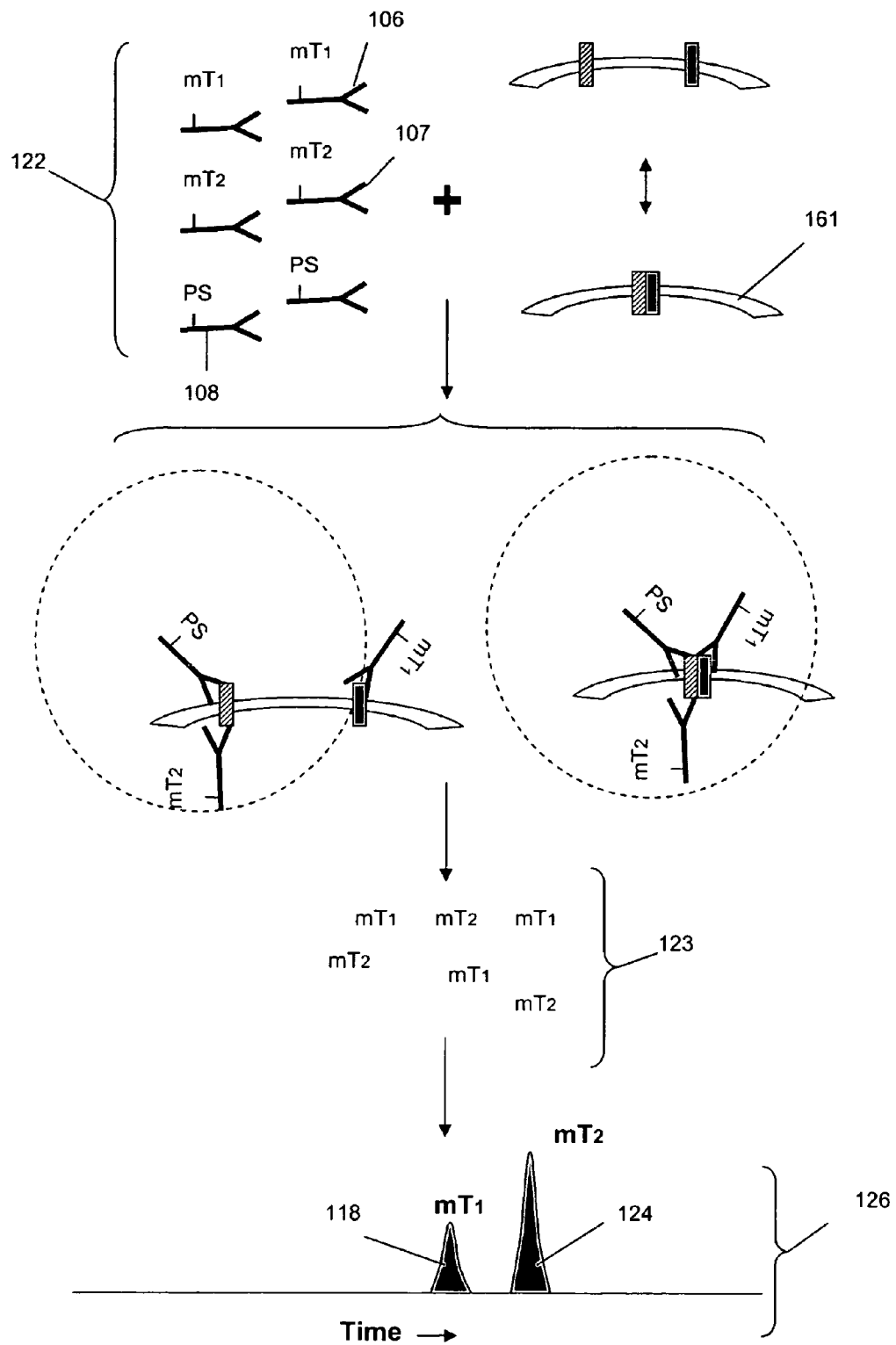

Homodimeric as well as heterodimeric complexes may be measured as illustrated in FIG. 4C. As above, an assay may comprise three reagents (128): cleaving probes (134), first binding compound (130), and second binding compound (132). First binding compound (130) and cleaving probe (134) are constructed to be specific for the same antigenic determinant (135) on protein (138) that exists (140) in a sample as either a homodimer (136) or a monomer (138). After reagents (128) are combined with a sample under conditions that promote the formation of stable complexes between the reagents and their respective targets, multiple complexes (142 through 150) form in the assay mixture. Because cleaving probe (134) and binding compound (130) are specific for the same antigenic determinant (135), four different combinations (144 through 150) of reagents may form complexes with homodimers. Of the complexes in the assay mixture, only those (143) with both a cleaving probe (134) and at least one binding compound will contribute released molecular tags (151) for separation and detection (154). In this embodiment, the size of peak (153) is proportional to the amount of homodimer in the assay mixture, while the size of peak (152) is proportional to the total amount of protein (138) in the assay mixture, both in monomeric form (142) or in homodimeric form (146 and 148).

Figure 4E:
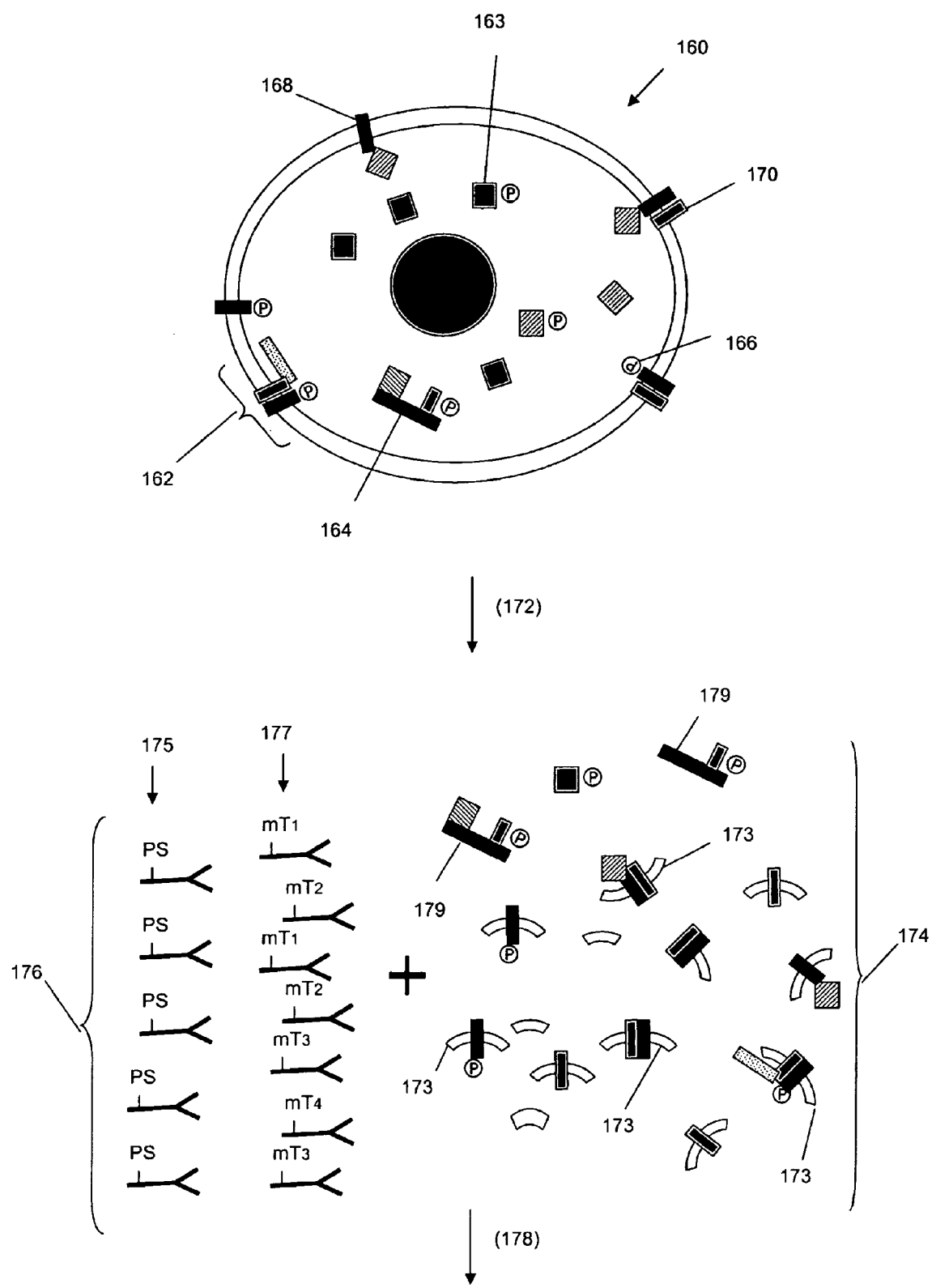
Figure 4F:
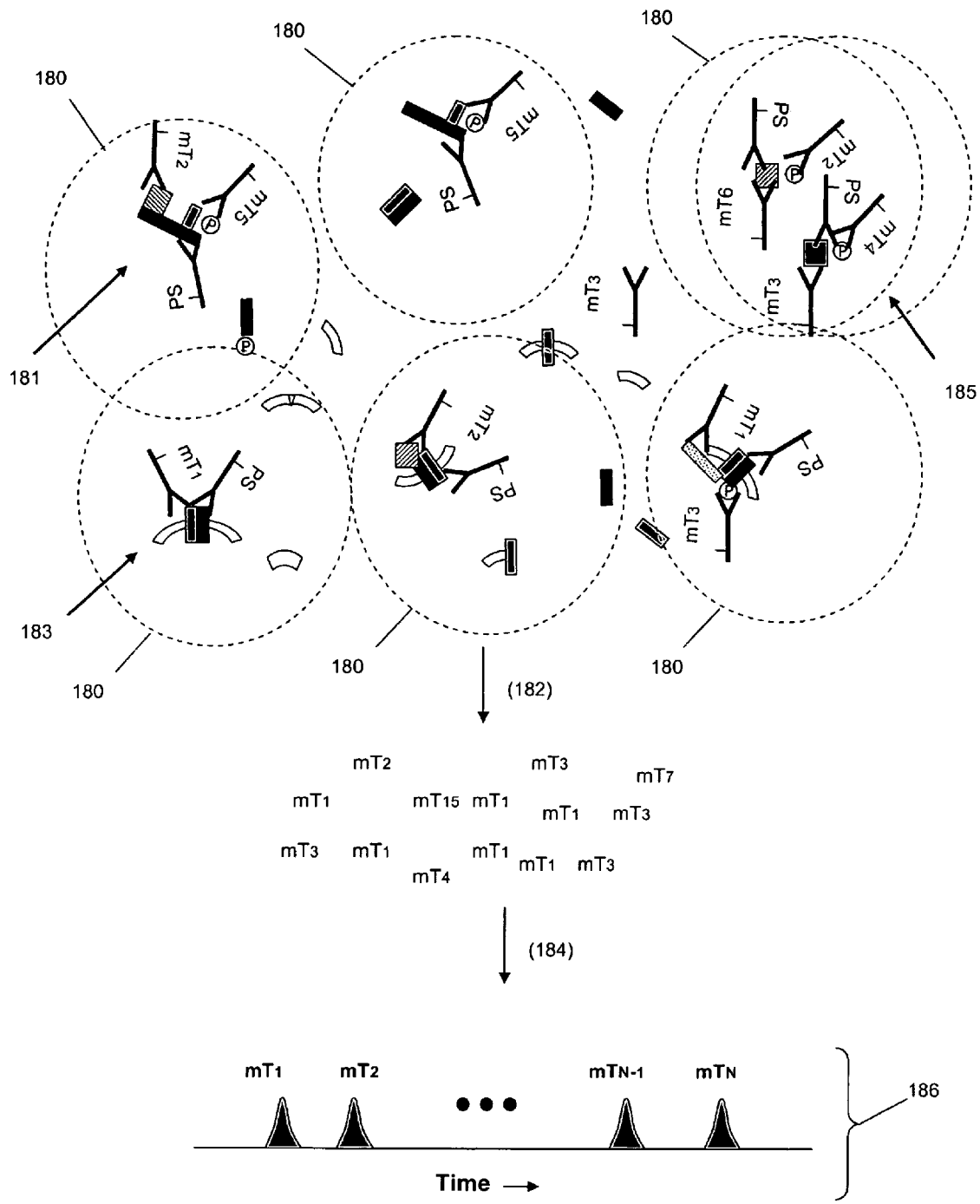

Another aspect of the invention is illustrated in FIGS. 4E and 4F, which provides for the simultaneous detection or measurement of multiple complexes, dimers, and activated effector proteins in a cellular sample. Cells (160), which may be from a sample from in vitro cultures or from a specimen of patient tissue, are lysed (172) to form lysate (174) in which cellular components are rendered accessible, such components including molecular complexes associated with the cell membrane (173), and/or within the cytosol (179), and/or within the cell nucleus. Complexes associated with signaling pathways include, but are not limited to, surface receptor complexes, such as receptor dimers (162 or 170), receptor complexes including adaptor or scaffold molecules of various types (162, 168, or 170), dimers and higher order complexes of intracellular proteins (164), phosphorylation sites of proteins in such complexes (166), phosphorylated effector proteins (163), and the like. After lysing, the resulting lysate (174) is combined with assay reagents (176) that include multiple cleaving probes (175) and multiple binding compounds (177). Assay conditions are selected (178) that allow reagents (176) to specifically bind to their respective targets, so that upon activation cleavable linkages within the effective proximity (180) of the cleavage-inducing moieties are cleaved and molecular tags are released (182). Also illustrated are intracellular complexes, e.g. signaling complexes (181), receptor dimers (183), and effector proteins (185). As above, after cleavage, the released molecular tags are separated (184) and identified in a separation profile (186), such as an electropherogram, and based on the number and quantities of molecular tags measured, a profile is obtained of the selected molecular complexes, protein dimers, and/or effector proteins in the cells of the sample.

One skilled in the art would understand that dimers may be measured in either lysates of cells or tissues, or in fixed samples whose membranes have been permeabilized or removed by the fixing process. In such cases, binding compounds may be specific for either extracellular or intracellular domains of cell surface membrane receptors.

Figure 4G:
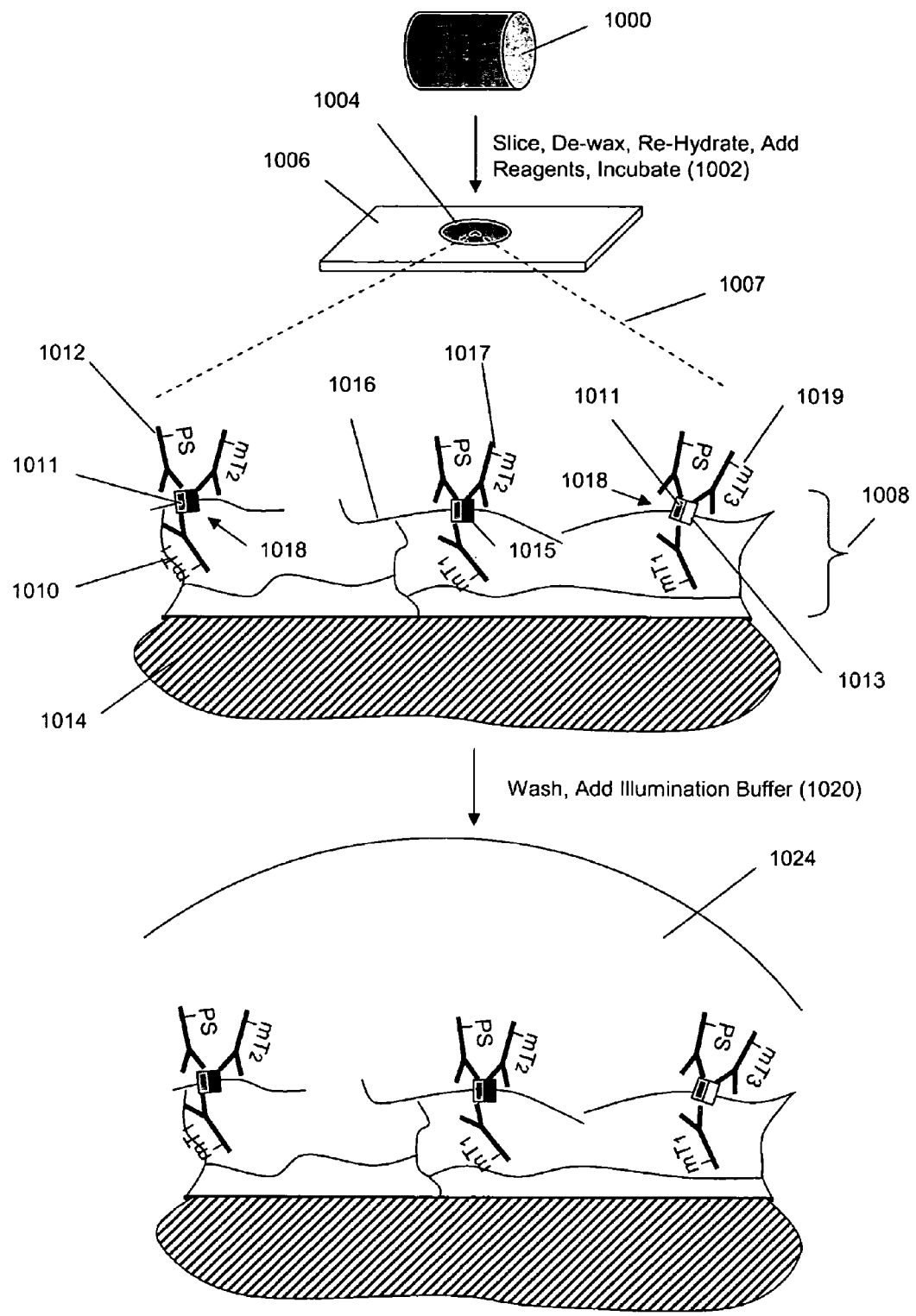
FIGS. 4G-4H illustrate diagrammatically the use of releasable molecular tags to measure cell surface receptor complexes in fixed tissue specimens.
Figure 4H:
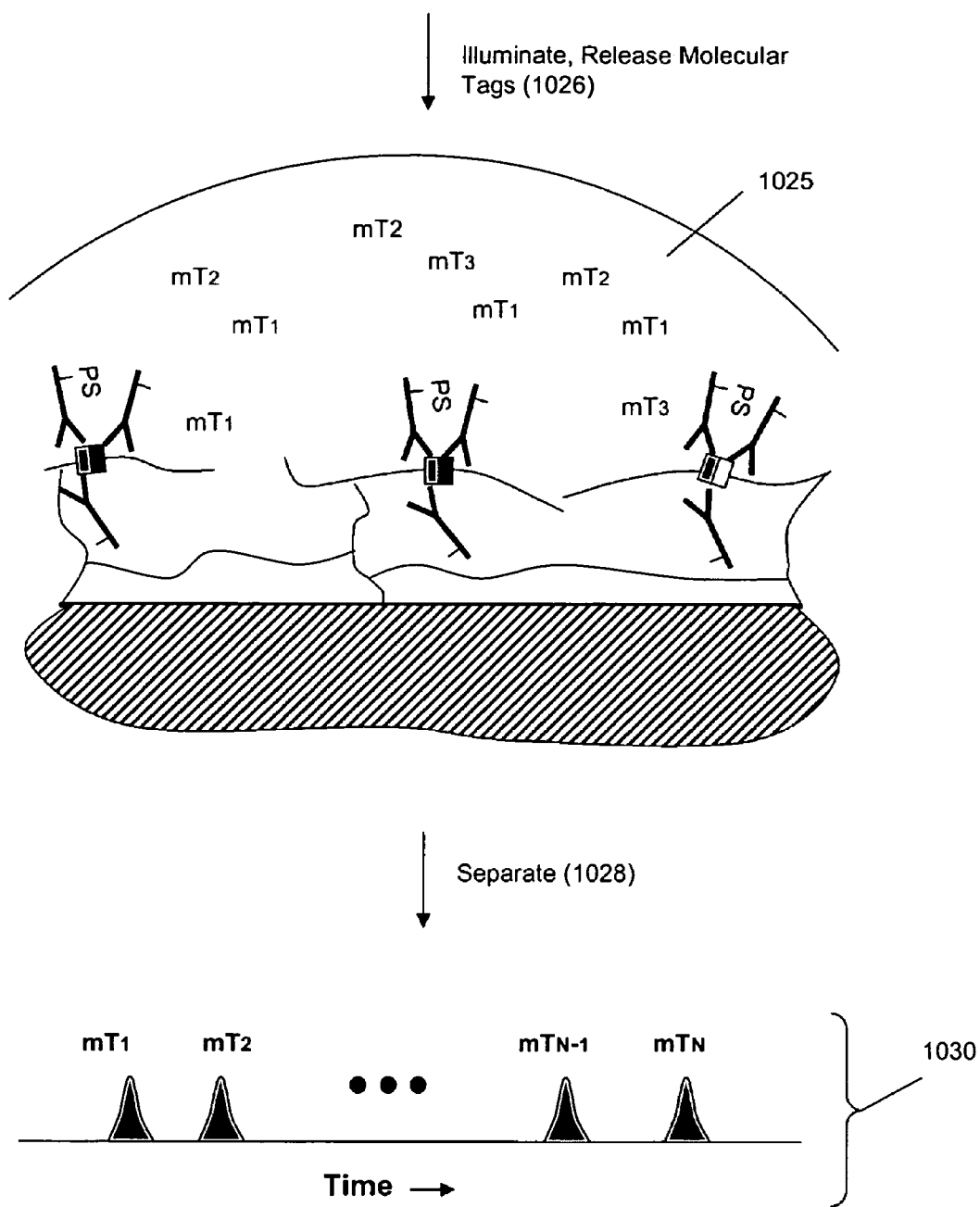

FIGS. 4G and 4H illustrate an embodiment of the invention for measuring receptor complexes in fixed or frozen tissue samples. Fixed tissue sample (1000), e.g. a formalin-fixed paraffin-embedded sample, is sliced to provide a section (1004) using a microtome, or like instrument, which after placing on surface (1006), which may be a microscope slide, it is de-waxed and re-hydrated for application of assay reagents. Enlargement (1007) shows portion (1008) of section (1004) on portion (1014) of microscope slide (1006). Receptor dimer molecules (1018) are illustrated as embedded in the remnants of membrane structure (1016) of the fixed sample. In accordance with this aspect of the invention, cleaving probe and binding compounds are incubated with the fixed sample so that they bind to their target molecules. For example, cleaving probes (1012) (illustrated in the figure as an antibody having a photosensitizer ("PS") attached) and first binding compound (1010) (illustrated as an antibody having molecular tag "$mT_1$" attached) specifically bind to receptor (1011) common to all of the dimers shown, second binding compound (1017) (with "$mT_2$") specifically binds to receptor (1015), and third binding compound (1019) (with "$mT_3$") specifically binds to receptor (1013). After washing to remove binding compounds and cleaving probe that are not specifically bound to their respective target molecules, buffer (1024) (referred to as "illumination buffer" in the figure) is added. For convenience, buffer (1024) may be contained on section (1004), or a portion thereof, by creating a hydrophobic barrier on slide (1006), e.g. with a wax pen. After illumination of photosensitizers and release of molecular tags (1026), buffer (1024) now containing release molecular tags (1025) is transferred to a separation device, such as a capillary electrophoresis instrument, for separation (1028) and identification of the released molecular tags in, for example, electropherogram (1030).

Measurements made directly on tissue samples, particularly as illustrated in FIGS. 4G and 4H, may be normalized by including measurements on cellular or tissue targets that are representative of the total cell number in the sample and/or the numbers of particular subtypes of cells in the sample. The additional measurement may be preferred, or even necessary, because of the cellular and tissue heterogeneity in patient samples, particularly tumor samples, which may comprise substantial fractions of normal cells. For example, in FIG. 4H, values for the total amount of receptor (1011) may be given as a ratio of the following two measurements: area of peak (1032) of molecular tag ("$mT_1$") and the area of a peak corresponding to a molecular tag correlated with a cellular or tissue component common to all the cells in the sample, e.g. tubulin, or the like. Accordingly, detection methods based on releasable molecular tags may include an additional step of providing a binding compound (with a distinct molecular tag) specific for a normalization protein, such as tubulin.

Figure 6:
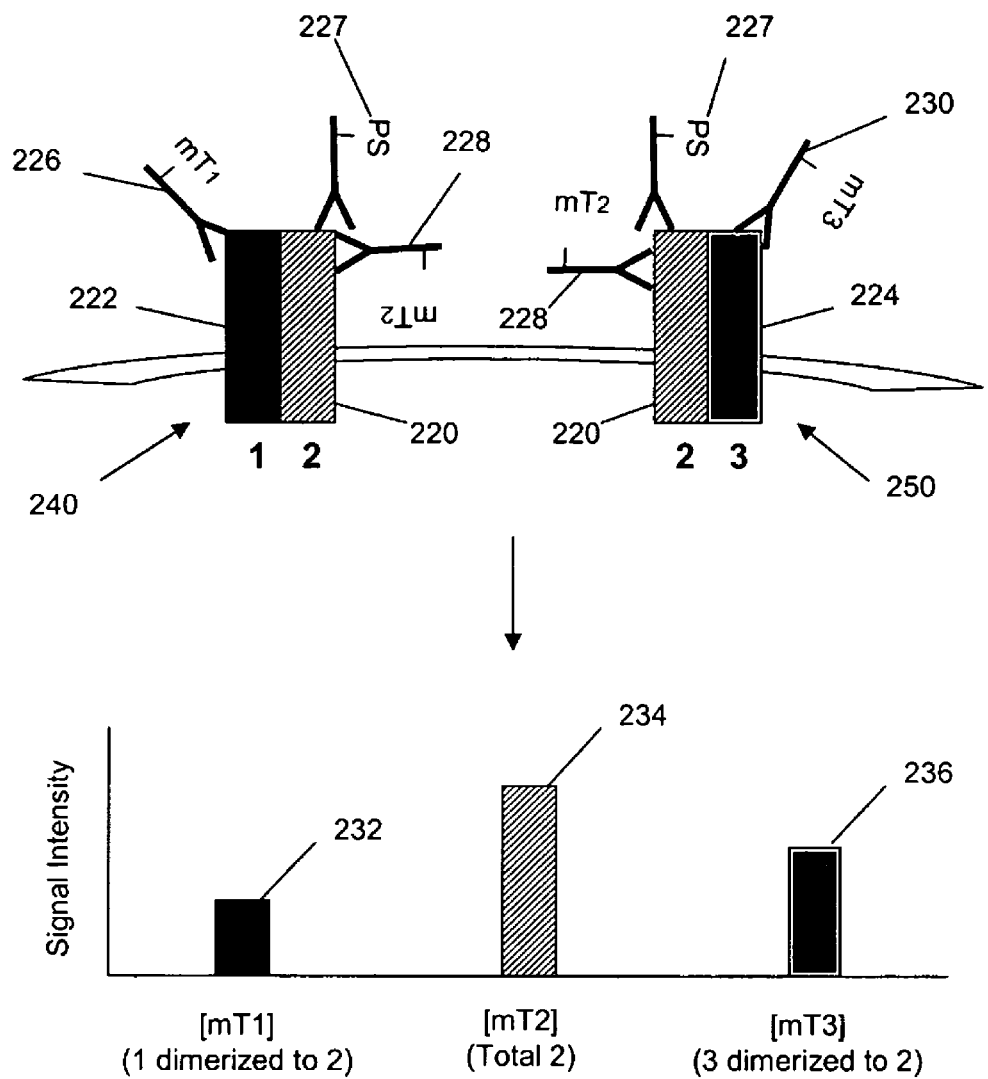
FIG. 6 illustrates an embodiment for measuring relative amounts of receptor dimers containing a common component receptor.

A preferred embodiment for measuring relative amounts of receptor dimers containing a common component receptor is illustrated in FIG. 6. In this assay design, two different receptor dimers ("1-2" (240) and "2-3" (250)) each having a common component, "2," may be measured ratiometrically with respect to the common component. An assay design is shown for measuring receptor heterodimer (240) comprising receptor "1" (222) and receptor "2" (220) and receptor heterodimer (250) comprising receptor "2" (220) and receptor "3" (224). A key feature of this embodiment is that cleaving probe (227) is made specific for the common receptor of the pair of heterodimers. Binding compound (228) specific for receptor "2" provides a signal (234) related to the total amount of receptor "2" in the assay, whereas binding compound (226) specific for receptor "1" and binding compound (230) specific for receptor "3" provide signals (232 and 236, respectively) related only to the amount of receptor "1" and receptor "3" present as heterodimers with receptor "2," respectively. The design of FIG. 6 may be generalized to more than two receptor complexes that contain a common component by simply adding binding compounds specific for the components of the additional complexes.

A. Binding Compounds and Molecular Tags

As mentioned above, mixtures containing pluralities of different binding compounds may be provided, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specific binding or stable complex formation with an analyte of interest, such as a complex of proteins. In one aspect, a binding compound, which can be represented by the formula below, comprises one or more molecular tags attached to a binding moiety.

$$B\text{-}(L\text{-}E)_k$$

wherein B is binding moiety; L is a cleavable linkage; and E is a molecular tag. In homogeneous assays, cleavable linkage, L, may be an oxidation-labile linkage, and more preferably, it is a linkage that may be cleaved by singlet oxygen. The moiety "-$(L\text{-}E)_k$" indicates that a single binding compound may have multiple molecular tags attached via cleavable linkages. In one aspect, k is an integer greater than or equal to one, but in other embodiments, k may be greater than several hundred, e.g. 100 to 500, or k is greater than several hundred to as many as several thousand, e.g. 500 to 5000. Usually each of the plurality of different types of binding compound has a different molecular tag, E. Cleavable linkages, e.g. oxidation-labile linkages, and molecular tags, E, are attached to B by way of conventional chemistries.

Preferably, B is an antibody binding composition that specifically binds to a target, such as a predetermined antigenic determinant of a target protein, such as a cell surface receptor. Such compositions are readily formed from a wide variety of commercially available antibodies, both monoclonal and polyclonal, specific for proteins of interest. In particular, antibodies specific for epidermal growth factor receptors are disclosed in the following patents, all of which are incorporated by references: U.S. Pat. Nos. 5,677,171; 5,772,997; 5,968,511; 5,480,968; 5,811,098. U.S. Pat. No. 6,488,390, incorporated herein by reference, discloses antibodies specific for a G-protein coupled receptor, CCR4. U.S. Pat. No. 5,599,681, incorporated herein by reference, discloses antibodies specific for phosphorylation sites of proteins. Commercial vendors, such as Cell Signaling Technology (Beverly, Mass.), Biosource International (Camarillo, Calif.), and Upstate (Charlottesville, Va.), also provide monoclonal and polyclonal antibodies specific for many receptors.

Cleavable linkage, L, can be virtually any chemical linking group that may be cleaved under conditions that do not degrade the structure or affect detection characteristics of the released molecular tag, E. Whenever a cleaving probe is used in a homogeneous assay format, cleavable linkage, L, is cleaved by a cleavage agent generated by the cleaving probe that acts over a short distance so that only cleavable linkages in the immediate proximity of the cleaving probe are cleaved. Typically, such an agent must be activated by making a physical or chemical change to the reaction mixture so that the agent produces a short lived active species that diffuses to a cleavable linkage to effect cleavage. In a homogeneous format, the cleavage agent is preferably attached to a binding moiety, such as an antibody, that targets prior to activation the cleavage agent to a particular site in the proximity of a binding compound with releasable molecular tags. In such embodiments, a cleavage agent is referred to herein as a cleavage-inducing moiety, which is discussed more fully below.

In a non-homogeneous format, because specifically bound binding compounds are separated from unbound binding compounds, a wider selection of cleavable linkages and cleavage agents are available for use. Cleavable linkages may not only include linkages that are labile to reaction with a locally acting reactive species, such as hydrogen peroxide, singlet oxygen, or the like, but also linkages that are labile to agents that operate throughout a reaction mixture, such as base-labile linkages, photocleavable linkages, linkages cleavable by reduction, linkages cleaved by oxidation, acid-labile linkages, peptide linkages cleavable by specific proteases, and the like. References describing many such linkages include Greene and Wuts, Protective Groups in Organic Synthesis, Second Edition (John Wiley & Sons, New York, 1991); Hermanson, Bioconjugate Techniques (Academic Press, New York, 1996); and Still et al., U.S. Pat. No. 5,565,324.

In one aspect, commercially available cleavable reagent systems may be employed with the invention. For example, a disulfide linkage may be introduced between an antibody binding composition and a molecular tag using a heterofunctional agent such as N-succinimidyl 3-(2-pyridyldithio)propionate (SPDP), succinimidyloxycarbonyl-α-methyl-α-(2-pyridyldithio)toluene (SMPT), or the like, available from vendors such as Pierce Chemical Company (Rockford, Ill.). Disulfide bonds introduced by such linkages can be broken by treatment with a reducing agent, such as dithiothreitol (DTT), dithioerythritol (DTE), 2-mercaptoethanol, sodium borohydride, or the like. Typical concentrations of reducing agents to effect cleavage of disulfide bonds are in the range of from 10 to 100 mM. An oxidatively labile linkage may be introduced between an antibody binding composition and a molecular tag using the homobifunctional NHS ester cross-linking reagent, disuccinimidyl tartarate (DST)(available from Pierce) that contains central cis-diols that are susceptible to cleavage with sodium periodate (e.g., 15 mM periodate at physiological pH for 4 hours). Linkages that contain esterified spacer components may be cleaved with strong nucleophilic agents, such as hydroxylamine, e.g., 0.1 N hydroxylamine, pH 8.5, for 3-6 hours at 37° C. Such spacers can be introduced by a homobifunctional cross-linking agent such as ethylene glycol bis(succinimidylsuccinate)(EGS) available from Pierce (Rockford, Ill.). A base labile linkage can be introduced with a sulfone group. Homobifunctional cross-linking agents that can be used to introduce sulfone groups in a cleavable linkage include bis[2-(succinimidyloxycarbonyloxy)ethyl]sulfone (BSOCOES), and 4,4-difluoro-3,3-dinitrophenylsulfone (DFDNPS). Exemplary basic conditions for cleavage include 0.1 M sodium phosphate, adjusted to pH 11.6 by addition of Tris base, containing 6 M urea, 0.1% SDS, and 2 mM DTT, with incubation at 37° C. for 2 hours. Photocleavable linkages include those disclosed in Rothschild et al., U.S. Pat. No. 5,986,076.

When L is oxidation labile, L may be a thioether or its selenium analog; or an olefin, which contains carbon-carbon double bonds, wherein cleavage of a double bond to an oxo group, releases the molecular tag, E. Illustrative oxidation labile linkages are disclosed in Singh et al., U.S. Pat. No. 6,627,400; and U.S. patent publications Singh et al., 2002/0013126; and 2003/0170915, and in Willner et al., U.S. Pat. No. 5,622,929, all of which are incorporated herein by reference.

Molecular tag, E, in the present invention may comprise an electrophoric tag as described in the following references when separation of pluralities of molecular tags are carried out by gas chromatography or mass spectrometry: Zhang et al., Bioconjugate Chem., 13: 1002-1012 (2002); Giese, Anal. Chem., 2: 165-168 (1983); and U.S. Pat. Nos. 4,650,750; 5,360,819; 5,516,931; 5,602,273; and the like.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. Preferred structures of E are described more fully below. E may comprise a detection group for generating an electrochemical, fluorescent, or chromogenic signal. In embodiments employing detection by mass, E may not have a separate moiety for detection purposes. Preferably, the detection group generates a fluorescent signal.

B. Attaching Molecular Tags to Binding Moieties

Extensive guidance can be found in the literature for covalently linking molecular tags to binding compounds, such as antibodies, e.g. Hermanson, Bioconjugate Techniques, (Academic Press, New York, 1996), and the like. In one aspect of the invention, one or more molecular tags are attached directly or indirectly to common reactive groups on a binding compound. Common reactive groups include amine, thiol, carboxylate, hydroxyl, aldehyde, ketone, and the like, and may be coupled to molecular tags by commercially available cross-linking agents, e.g. Hermanson (cited above); Haugland, Handbook of Fluorescent Probes and Research Products, Ninth Edition (Molecular Probes, Eugene, Oreg., 2002). In one embodiment, an NHS-ester of a molecular tag is reacted with a free amine on the binding compound.

Figure 5A:
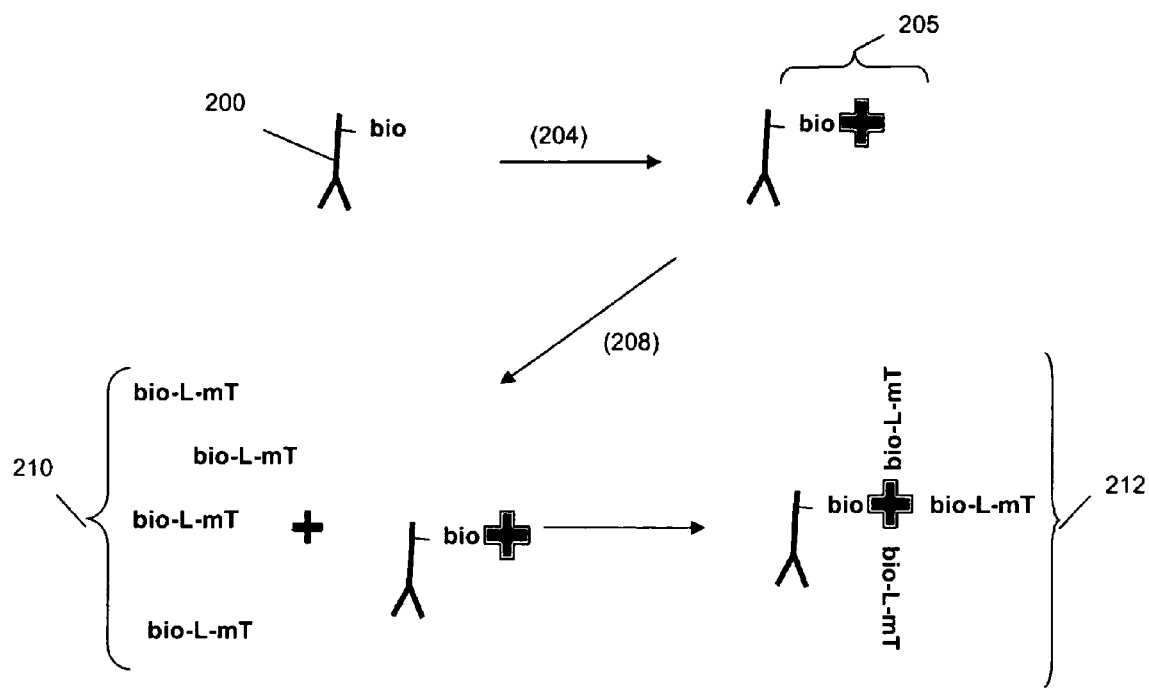
FIGS. 5A-5E illustrate diagrammatically methods for attaching molecular tags to antibodies.

In another embodiment illustrated in FIG. 5A, binding compounds comprise a biotinylated antibody (200) as a binding moiety. Molecular tags are attached to binding moiety (200) by way of avidin or streptavidin bridge (206). Preferably, in operation, binding moiety (200) is first reacted with a target complex, after which avidin or streptavidin is added (204) to form antibody-biotin-avidin complex (205). To such complexes (205) are added (208) biotinylated molecular tags (210) to form binding compound (212).

Figure 5B:
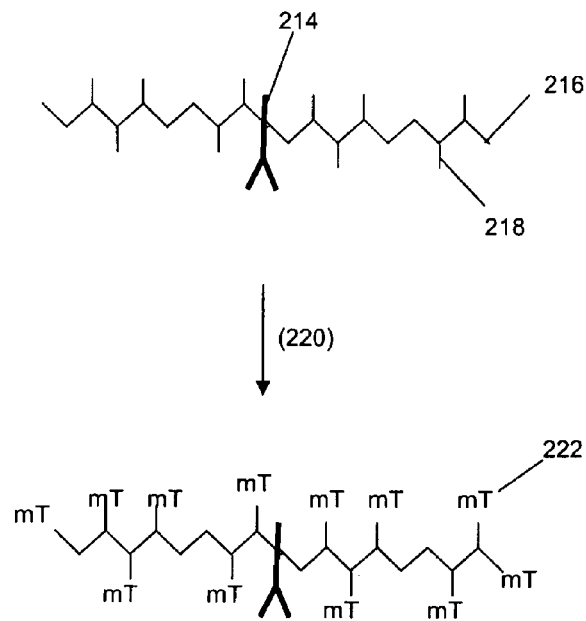

In still another embodiment illustrated in FIG. 5B, binding compounds comprise an antibody (214) derivatized with a multi-functional moiety (216) that contains multiple functional groups (218) that are reacted (220) molecular tag precursors to give a final binding compound having multiple molecular tags (222) attached. Exemplary multi-functional moieties include aminodextran, and like materials.

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment or assay. Factors that may affect such design choices include, but are not limited to, antibody affinity and avidity for a particular target, relative prevalence of a target, fluorescent characteristics of a detection moiety of a molecular tag, and the like.

C. Separation of Released Molecular Tags

Molecular tags within a plurality are selected so that each has a unique separation characteristic and/or a unique optical property with respect to the other members of the same plurality. In one aspect, the chromatographic or electrophoretic separation characteristic is retention time under set of standard separation conditions conventional in the art, e.g. voltage, column pressure, column type, mobile phase, electrophoretic separation medium, or the like. In another aspect, the optical property is a fluorescence property, such as emission spectrum, fluorescence lifetime, fluorescence intensity at a given wavelength or band of wavelengths, or the like. Preferably, the fluorescence property is fluorescence intensity. For example, each molecular tag of a plurality may have the same fluorescent emission properties, but each will differ from one another by virtue of a unique retention time. On the other hand, or two or more of the molecular tags of a plurality may have identical migration, or retention, times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more. Preferably, in such conventional apparatus, the electrophoretic mobilities of molecular tags of a plurality differ by at least one percent, and more preferably, by at least a percentage in the range of from 1 to 10 percent. Molecular tags are identified and quantified by analysis of a separation profile, or more specifically, an electropherogram, and such values are correlated with the amounts and kinds of receptor dimers present in a sample. For example, during or after electrophoretic separation, the molecular tags are detected or identified by recording fluorescence signals and migration times (or migration distances) of the separated compounds, or by constructing a chart of relative fluorescent and order of migration of the molecular tags (e.g., as an electropherogram). Preferably, the presence, absence, and/or amounts of molecular tags are measured by using one or more standards as disclosed by Williams et al., U.S. patent publication No. 2003/0170734A1, which is incorporated herein by reference.

Pluralities of molecular tags may also be designed for separation by chromatography based on one or more physical characteristics that include but are not limited to molecular weight, shape, solubility, pKa, hydrophobicity, charge, polarity, or the like, e.g. as disclosed in U.S. patent publication No. 2003/0235832, which is incorporated by reference. A chromatographic separation technique is selected based on parameters such as column type, solid phase, mobile phase, and the like, followed by selection of a plurality of molecular tags that may be separated to form distinct peaks or bands in a single operation. Several factors determine which HPLC technique is selected for use in the invention, including the number of molecular tags to be detected (i.e. the size of the plurality), the estimated quantities of each molecular tag that will be generated in the assays, the availability and ease of synthesizing molecular tags that are candidates for a set to be used in multiplexed assays, the detection modality employed, and the availability, robustness, cost, and ease of operation of HPLC instrumentation, columns, and solvents. Generally, columns and techniques are favored that are suitable for analyzing limited amounts of sample and that provide the highest resolution separations. Guidance for making such selections can be found in the literature, e.g. Snyder et al., Practical HPLC Method Development, (John Wiley & Sons, New York, 1988); Millner, "High Resolution Chromatography: A Practical Approach", Oxford University Press, New York (1999), Chi-San Wu, "Column Handbook for Size Exclusion Chromatography", Academic Press, San Diego (1999), and Oliver, "HPLC of Macromolecules: A Practical Approach, Oxford University Press", Oxford, England (1989). In particular, procedures are available for systematic development and optimization of chromatographic separations given conditions, such as column type, solid phase, and the like, e.g. Haber et al., J. Chromatogr. Sci., 38: 386-392 (2000); Outinen et al., Eur. J. Pharm. Sci., 6: 197-205 (1998); Lewis et al., J. Chromatogr., 592: 183-195 and 197-208 (1992); and the like. An exemplary HPLC instrumentation system suitable for use with the present invention is the Agilent 1100 Series HPLC system (Agilent Technologies, Palo Alto, Calif.).

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, 8$^{th}$ ed., (Molecular Probes, Eugene, 2002); Lee et al., U.S. Pat. No. 6,191,278; Lee et al., U.S. Pat. No. 6,372,907; Menchen et al., U.S. Pat. No. 6,096,723; Lee et al., U.S. Pat. No. 5,945,526; Lee et al., Nucleic Acids Research, 25: 2816-2822 (1997); Hobb, Jr., U.S. Pat. No. 4,997,928; Khanna et al., U.S. Pat. No. 4,318,846; and the like. Preferably, D is a fluorescein or a fluorescein derivative.

D. Cleavage-Inducing Moiety Producing Active Species

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al., Meth. Enzymol., 319: 226-241 (2000).

An important consideration in designing assays employing a cleavage-inducing moiety and a cleavable linkage is that they not be so far removed from one another when bound to a receptor complex that the active species generated by the cleavage-inducing moiety cannot efficiently cleave the cleavable linkage. In one aspect, cleavable linkages preferably are within 1000 nm, and preferably within 20-200 nm, of a bound cleavage-inducing moiety. More preferably, for photosensitizer cleavage-inducing moieties generating singlet oxygen, cleavable linkages are within about 20-100 nm of a photosensitizer in a receptor complex. The range within which a cleavage-inducing moiety can effectively cleave a cleavable linkage (that is, cleave enough molecular tag to generate a detectable signal) is referred to herein as its "effective proximity." One of ordinary skill in the art recognizes that the effective proximity of a particular sensitizer may depend on the details of a particular assay design and may be determined or modified by routine experimentation.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al., FEBS Lett., 355: 287 (1994) (peroxidases and oxygenases); Kanofsky, J. Biol. Chem. 258: 5991-5993 (1983)(lactoperoxidase); Pierlot et al., Meth. Enzymol., 319: 3-20 (2000)(thermal lysis of endoperoxides); and the like. Attachment of a binding agent to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970).

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructing of such compositions, particularly for antibodies as binding agents, is available in the literature, e.g. in the fields of photodynamic therapy, immunodiagnostics, and the like. The following are exemplary references: Ullman, et al., Proc. Natl. Acad. Sci. USA 91, 5426-5430 (1994); Strong et al., Ann. New York Acad. Sci., 745: 297-320 (1994); Yarmush et al., Crit. Rev. Therapeutic Drug Carrier Syst., 10: 197-252 (1993); Pease et al., U.S. Pat. No. 5,709,994; Ullman et al., U.S. Pat. No. 5,340,716; Ullman et al., U.S. Pat. No. 6,251,581; McCapra, U.S. Pat. No. 5,516,636; and the like.

A large variety of light sources are available to photoactivate photosensitizers to generate singlet oxygen. Both polychromatic and monochromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like. By way of example, a photoactivation device disclosed in Bjornson et al., International patent publication WO 03/051669 is employed. Briefly, the photoactivation device is an array of light emitting diodes (LEDs) mounted in housing that permits the simultaneous illumination of all the wells in a 96-well plate. A suitable LED for use in the present invention is a high power GaAlAs IR emitter, such as model OD-880W manufactured by OPTO DIODE CORP. (Newbury Park, Calif.).

Examples of photosensitizers that may be utilized in the present invention are those that have the above properties and are enumerated in the following references: Singh and Ullman, U.S. Pat. No. 5,536,834; Li et al., U.S. Pat. No. 5,763,602; Martin et al., Methods Enzymol., 186: 635-645 (1990); Yarmush et al., Crit. Rev. Therapeutic Drug Carrier Syst., 10: 197-252 (1993); Pease et al., U.S. Pat. No. 5,709,994; Ullman et al., U.S. Pat. No. 5,340,716; Ullman et al., U.S. Pat. No. 6,251,581; McCapra, U.S. Pat. No. 5,516,636; Thetford, European patent publ. 0484027; Sessler et al., SPIE, 1426: 318-329 (1991); Magda et al., U.S. Pat. No. 5,565,552; Roelant, U.S. Pat. No. 6,001,673; and the like.

As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically.

Figure 5C:
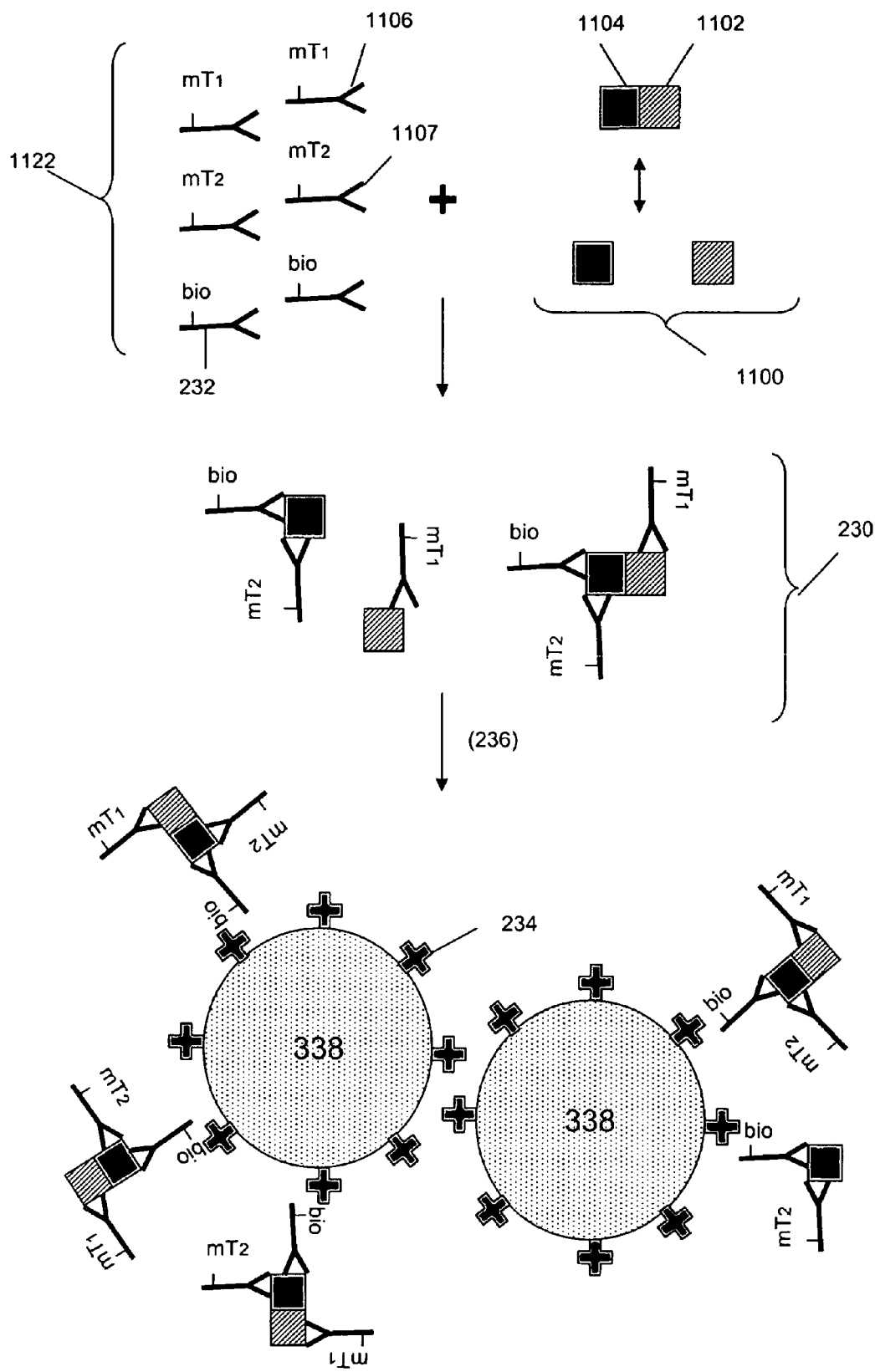
Figure 5D:
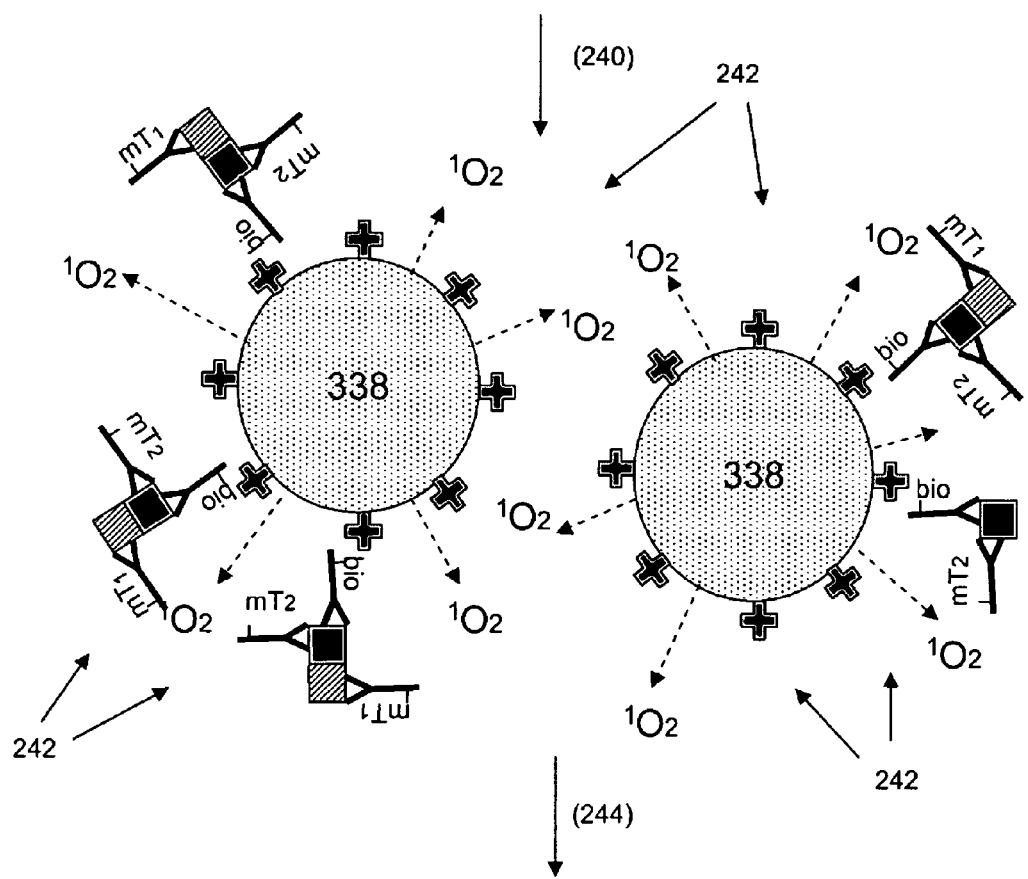
Figure 5D:
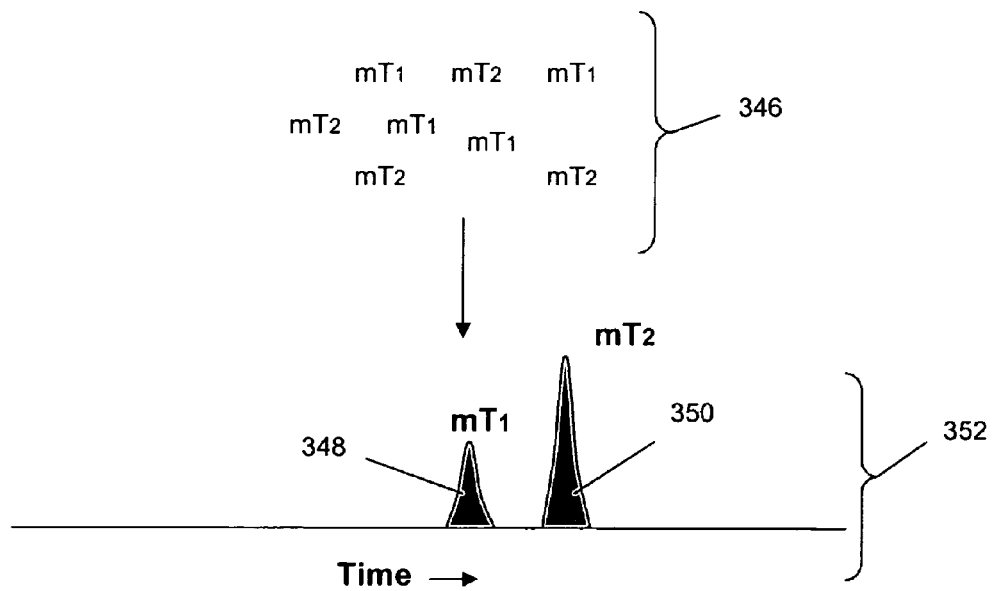

In one embodiment, a photosensitizer is incorporated into a latex particle to form photosensitizer beads, e.g. as disclosed by Pease et al., U.S. Pat. No. 5,709,994; Pollner, U.S. Pat. No. 6,346,384; and Pease et al., PCT publication WO 01/84157. Alternatively, photosensitizer beads may be prepared by covalently attaching a photosensitizer, such as rose bengal, to 0.5 micron latex beads by means of chloromethyl groups on the latex to provide an ester linking group, as described in J. Amer. Chem. Soc., 97: 3741 (1975). Use of such photosensitizer beads is illustrated in FIGS. 5C and 5D. As described in FIG. 4B for heteroduplex detection, complexes (230) are formed after combining reagents (1122) with a sample (1100). This reaction may be carried out, for example, in a conventional 96-well or 384-well microtiter plate, or the like, having a filter membrane that forms one wall, e.g. the bottom, of the wells that allows reagents to be removed by the application of a vacuum. This allows the convenient exchange of buffers, if the buffer required for specific binding of binding compounds is different that the buffer required for either singlet oxygen generation or separation. For example, in the case of antibody-based binding compounds, a high salt buffer is required. If electrophoretic separation of the released tags is employed, then better performance is achieved by exchanging the buffer for one that has a lower salt concentration suitable for electrophoresis. In this embodiment, instead of attaching a photosensitizer directly to a binding compound, such as an antibody, a cleaving probe comprises two components: antibody (232) derivatized with a capture moiety, such as biotin (indicated in FIG. 5C as "bio") and photosensitizer bead (338) whose surface is derivatized with an agent (234) that specifically binds with the capture moiety, such as avidin or streptavidin. Complexes (230) are then captured (236) by photosensitizer beads (338) by way of the capture moiety, such as biotin. Conveniently, if the pore diameter of the filter membrane is selected so that photosensitizer beads (338) cannot pass, then a buffer exchange also serves to remove unbound binding compounds, which leads to an improved signal. As illustrated in FIG. 5D, after an appropriate buffer for separation has been added, if necessary, photosensitizer beads (338) are illuminated (240) so that singlet oxygen is generated (242) and molecular tags are released (244). Such released molecular tags (346) are then separated to form separation profile (352) and dimers are quantified ratiometrically from peaks (348) and (350). Photosensitizer beads may be used in either homogeneous or heterogeneous assay formats.

Figure 5E:
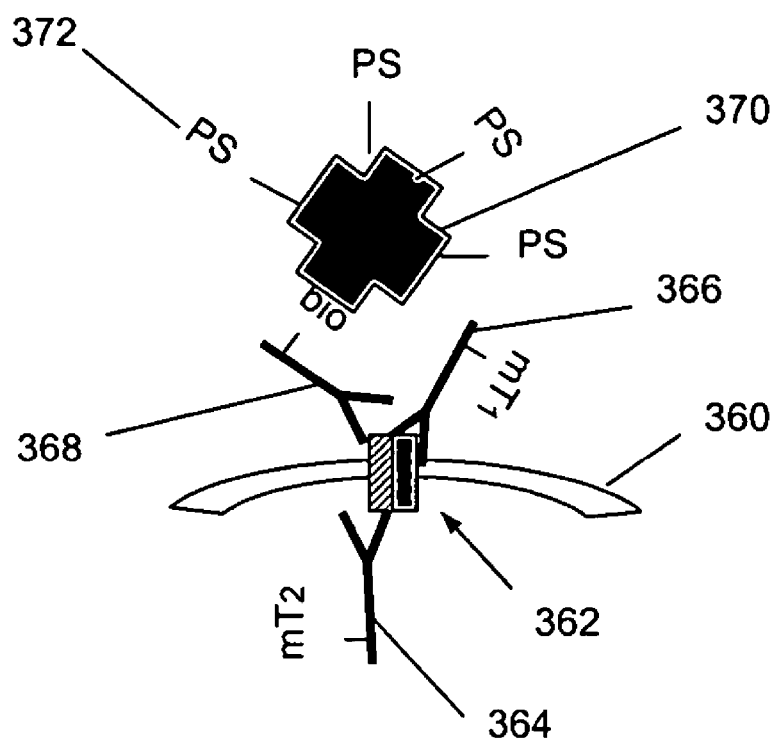

Preferably, when analytes, such as cell surface receptors, are being detected or antigen in a fixed sample, a cleaving probe may comprise a primary haptenated antibody and a secondary anti-hapten binding protein derivatized with multiple photosensitizer molecules. A preferred primary haptenated antibody is a biotinylated antibody, and preferred secondary anti-hapten binding proteins may be either an anti-biotin antibody or streptavidin. Other combinations of such primary and secondary reagents are well known in the art, e.g. Haugland, Handbook of Fluorescent Probes and Research Reagents, Ninth Edition (Molecular Probes, Eugene, Oreg., 2002). An exemplary combination of such reagents is illustrated in FIG. 5E. There binding compounds (366 and 368) having releasable tags ("$mT_1$" and "$mT_2$" in the Figure), and primary antibody (368) derivatized with biotin (369) are specifically bound to different epitopes of receptor dimer (362) in membrane (360). Biotin-specific binding protein (370), e.g. streptavidin, is attached to biotin (369) bringing multiple photosensitizers (372) into effective proximity of binding compounds (366 and 368). Biotin-specific binding protein (370) may also be an anti-biotin antibody, and photosensitizers may be attached via free amine group on the protein by conventional coupling chemistries, e.g. Hermanson (cited above). An exemplary photosensitizer for such use is an NHS ester of methylene blue prepared as disclosed in Shimadzu et al., European patent publication 0510688.

E. Assay Conditions

The following general discussion of methods and specific conditions and materials are by way of illustration and not limitation. One of ordinary skill in the art will understand how the methods described herein can be adapted to other applications, particularly with using different samples, cell types and target complexes.

In conducting the methods of the invention, a combination of the assay components is made, including the sample being tested, the binding compounds, and optionally the cleaving probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages, and may require incubations before the complete mixture has been assembled, or before the cleaving reaction is initiated.

The amounts of each reagent are usually determined empirically. The amount of sample used in an assay will be determined by the predicted number of target complexes present and the means of separation and detection used to monitor the signal of the assay. In general, the amounts of the binding compounds and the cleaving probe are provided in molar excess relative to the expected amount of the target molecules in the sample, generally at a molar excess of at least 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of oligomeric cell surface complexes, the compound may be added to the cells prior to, simultaneously with, or after addition of the probes, depending on the effect being monitored.

The assay mixture is combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° C. to 70° C., usually from about 15° C. to 45° C., more usually 25° C. to 37° C.

After assembly of the assay mixture and incubation to allow the probes to bind to cell surface molecules, the mixture is treated to activate the cleaving agent to cleave the tags from the binding compounds that are within the effective proximity of the cleaving agent, releasing the corresponding tag from the cell surface into solution. The nature of this treatment will depend on the mechanism of action of the cleaving agent. For example, where a photosensitizer is employed as the cleaving agent, activation of cleavage will comprise irradiation of the mixture at the wavelength of light appropriate to the particular sensitizer used.

Following cleavage, the sample is then analyzed to determine the identity of tags that have been released. Where an assay employing a plurality of binding compounds is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

As mentioned above, in some embodiments, if the assay reaction conditions may interfere with the separation technique employed, it may be necessary to remove, or exchange, the assay reaction buffer prior to cleavage and separation of the molecular tags. For example, assay conditions may include salt concentrations (e.g. required for specific binding) that degrade separation performance when molecular tags are separated on the basis of electrophoretic mobility. Thus, such high salt buffers may be removed, e.g. prior to cleavage of molecular tags, and replaced with another buffer suitable for electrophoretic separation through filtration, aspiration, dilution, or other means.

4. Disease Associated with Undesirable Angiogenesis

According to the present invention, multiple cellular components and their interactions in endothelial cells are analyzed to provide information for assessing angiogenesis and monitoring the disease status.

As used herein, the term "disease status" includes, but is not limited to, the following features: likelihood of contracting a disease, presence or absence of a disease, prognosis of disease severity, and likelihood that a patient will respond to treatment by a particular therapeutic agent that acts through a receptor complex. In regard to cancer, "disease status" further includes detection of precancerous or cancerous cells or tissues, the selection of patients that are likely to respond to treatment by a therapeutic agent that acts through inhibition of angiogenesis, directly or indirectly.

Examples of diseases associated with undesirable angiogenesis include, but are not limited to, restenosis (e.g. coronary, carotid, and cerebral lesions), benign tumors, a various types of cancers such as primary tumors and tumor metastasis, hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors include, but are not limited to, hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.

Specific types of cancers or malignant tumors, either primary or secondary, include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian tumor, leiomyoma tumor, cervical dysplasia and in situ carcinoma, neuroblastoma, retinoblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, medulloblastoma, leukemias, lymphomas, malignant melanomas, epidermoid carcinomas, and other carcinomas and sarcomas.

Examples of the hematological disorder include, but are not limited to, acute myeloid leukemia, acute promyelocytic leukemia, acute lymphoblastic leukemia, chronic myelogenous leukemia, the myelodysplastic syndromes, and sickle cell anemia. The proliferative responses associated with organ transplantation include those proliferative responses contributing to potential organ rejections or associated complications. Specifically, these proliferative responses may occur during transplantation of the heart, lung, liver, kidney, and other body organs or organ systems.

Abnormal angiogenesis includes those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

Specific types of diseases associated with abnormal angiogenesis include retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid obstructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells.

The inflammatory bowel diseases also exhibit extra intestinal manifestations, such as skin lesions. Such lesions are characterized by inflammation and abnormal angiogenesis and can occur at many sites other the gastrointestinal tract. Inhibition of angiogenesis by the combination of a camptothecin compound and gemcitabine should reduce the influx of inflammatory cells and prevent the lesion formation.

Sarcoidois, another chronic inflammatory disease, is characterized as a multisystem granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using a combination of a camptothecin compound and gemcitabine to inhibit angiogenesis, such granulomas formation can be inhibited. Psoriasis, also a chronic and recurrent inflammatory disease, is characterized by papules and plaques of various sizes.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen radicals that lead to pannus growth and cartilage destruction. The factors involved in angiogenesis may actively contribute to, and help maintain, the chronically inflamed state of rheumatoid arthritis.

5. Examples of Antiangiogenic Agents

According to the present invention, multiple cellular components and their interactions in endothelial cells are analyzed to provide information for assessing angiogenesis and monitoring the disease status which includes an individual's response or resistance to the treatment of an antiangiogenic agent.

A wide variety of anti-angiogenic agents have been developed. Examples of anti-angiogenesis agents include, but are not limited to, retinoid acid and derivatives thereof, 2-methoxyestradiol, ANGIOSTATIN™ protein, ENDOSTATIN™ protein, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel, platelet factor 4, protamine sulphate (clupeine), sulphated chitin derivatives (prepared from queen crab shells), sulphated polysaccharide peptidoglycan complex (sp-pg), staurosporine, modulators of matrix metabolism, including for example, proline analogs ((1-azetidine-2-carboxylic acid (LACA), cishydroxyproline, d,1-3,4-dehydroproline, thiaproline], $\alpha,\alpha$-dipyridyl, .beta.-aminopropionitrile fumarate, 4-propyl-5-(4-pyridinyl)-2 (3h)-oxazolone; methotrexate, mitoxantrone, heparin, interferons, 2 macroglobulin-serum, chimp-3, chymostatin, $\exists$-cyclodextrin tetradecasulfate, eponemycin; fumagillin, gold sodium thiomalate, d-penicillamine (CDPT), $\exists$-1-anticollagenase-serum, $\alpha$2-antiplasmin, bisantrene, lobenzarit disodium, n-(2-carboxyphenyl-4-chloroanthronilic acid disodium or "CCA", thalidomide; angostatic steroid, cargboxynaminolmidazole; metalloproteinase inhibitors such as BB94. Other anti-angiogenesis agents include antibodies, preferably monoclonal antibodies against these angiogenic growth factors: bFGF, aFGF, FGF-5, VEGF isoforms, VEGF-C, HGF/SF and Ang-1/Ang-2. Ferrara N. and Alitalo, K. "Clinical application of angiogenic growth factors and their inhibitors" (1999) Nature Medicine 5:1359-1364.

Mechanistically, according to Kerbel and Folkman (2002) (Nature Rev. 2:727-739) there are two classes of antiangiogenic agents: direct and indirect angiogenesis inhibitors. Examples of direct angiogenesis inhibitors that are undergoing clinical trials are listed in Table 1; and those of indirect angiogenesis inhibitors in Table 2.

Direct angiogenesis inhibitors, such as vitaxin, angiostatin and others, prevent vascular endothelial cells from proliferating, migrating or avoiding cell death in response to a spectrum of pro-angiogenic proteins, including VEGF, bFGF, IL-8, platelet-derived growth factor (PDGF) and PD-EGF (Table 1). Direct angiogenesis inhibitors are the least likely to induce acquired drug resistance, because they target genetically stable endothelial cells rather than unstable mutating tumor cells. Kerbel (1991) Bioessays 13:31-36. Tumors that are treated with direct-acting anti-angiogenic therapy did not develop drug resistance in mice (Boehm et al. (1997) Nature 390:404-407).

Indirect angiogenesis inhibitors generally prevent the expression of or block the activity of a tumor protein that activates angiogenesis, or block the expression of its receptor on endothelial cells (Table 2). Many of these tumor-cell proteins are the products of oncogenes that drive the angiogenic switch. The activities of oncogene and tumor-suppressor gene products were initially studied in in vitro assays that monitored cancer-cell proliferation, apoptosis resistance, immortalization and anchorage independence. Kerbel et al. (1998) Mol. Med. 4: 286-296. Because the increased cancer-cell proliferation and decreased apoptosis that was associated with oncogene activation in vitro correlated so well with tumor growth in vivo, there was no reason to suspect that these new anticancer drugs (for example, signal-transduction inhibitors such as trastuzumab (HERCEPTIN)) could also block the angiogenic output of a tumor. But activating mutations in oncogenes, as well as in the anti-apoptotic factor BCL2, have been shown to cause tumor cells to upregulate angiogenic proteins and to downregulate inhibitors of angiogenesis. Fernandez et al. (2001) J. Natl. Cancer Inst. 93:33-38.

TABLE 1

| Drug | Endothelia-cell target | Reference(s) |
|---|---|---|
| Angiostatin | Binds to ATP synthase, angiomotin and annexin II on endothelial cells to inhibit endothelial-cell proliferation and migration | Troyanovsky et al. (2001) J. Cell Biol. 152: 1247-1254 |
| Bevacizumab (Avastin) | Recombinant humanized monoclonal antibody against vascular endothelial growth factor (VEGF) | Bevacizumab (2002) Drugs R. D. 3: 28-30 |
| Arresten | Believed to bind integrin-$\alpha_1\beta_1$ to inhibit endothelial-cell proliferation, migration, tube formation and neovascularization | Colorado et al. (2000) Cancer Res. 60: 2520-2526 |
| Canstatin | Believed to bind integrin-$\alpha_v\beta_3$ to inhibit endothelial-cell proliferation, migration and tube formation | Kamphaus et al. (2000) J. Biol. Chem. 275: 1209-1215 |
| Combretastatin | Microtubules: induces reorganization of the actin cytoskeleton and early membrane blebbing in human endothelial cells | Kanthou et al. (2002) Blood 99: 2060-2069 |
| Endostatin | Believed to target integrin-$\alpha_5\beta_1$ to inhibit endothelial-cell proliferation and migration, and induce apoptosis of proliferating endothelial cells (R. Kalluri, personal communication); endostatin does not affect wound healing | Dixelius et al. (2000) Blood 95: 3403-3411 O'Reilly et al. (1997) Cell 88: 277-285 |
| NM-3 | An isocoumarin small-molecule inhibitor of VEGF. It was shown to selective inhibit endothelial-cell proliferation, sprouting and tube formation in vitro | Reimer et al. (2002) Cancer Res. 62: 789-795 |
| Thrombospondin | Blocks endothelial-cell migration and neovascularization in the cornea, but might not be specific for endothelial cells | Dameron et al. (1994) Science 265: 1582-1584. |
| Tumstatin | Binds to integrin $\alpha_v\beta_3$ endothelial cells; inhibits endothelial-cell proliferation and neovascularization | Maeshima et al. (2001) J. Biol. Chem. 276: 15240-15248. Maeshima et al. (2002) Science 295: 140-143 |
| 2-methoxyestradiol | Inhibits micro-tubule function in proliferating endothelial cells, resulting in endothelial-cell apoptosis | D'Amato et al. (1994) Proc. Natl. Acad. Sci. 91: 4082-4085 |
| Vitaxin | A humanized monoclonal antibody against integrin $\alpha_v\beta_3$ | Gutheil et al. (2002) Clin. Cancer Res. 6: 3056-3061 |

TABLE 2

| Cancer-cell target | Pro-angiogenic proteins | Drug | Reference(s) |
|---|---|---|---|
| EGF receptor tyrosine kinase | VEGF; bFGF; TGF-$\alpha$ | ZD1839 (Iressa); ZD6474; OSI774 (Tarceva); CI1033; PKI1666; IMC225 (Erbitux) | Ciardiello et al. (2001) Clin. Cancer Res. 7: 1459-1465. |
| VEGF receptor | VEGF receptor on endothelium | PTK787; ZD6474; SU6668; SU11248; Semaxanib (SU5416); IMC-1C11 | Tille t al. (2001) J. Pharmacol. Exp. Ther. 299: 1073-1086. Hoekman (2001) Cancer J. 7: S134-S138. |
| PDGF receptor | PDGF receptor | PTK787; SU11248; SU6668 | Tille t al. (2001) J. Pharmacol. Exp. Ther. 299: 1073-1086. |
| ERBB-2(HER-2/neu receptor tyrosine kinase) | VEGF, angiopoietin-1, TGF-$\beta$, PAI1; upregulates thrombospondin-1 | Herceptin | Kerbel et al. (1998) Mol. Med. 4: 286-296. Izumi (2002) Nature 416: 279-280. |
| Interferon (IFN)-$\alpha$ receptor | Inhibits expression of bFGF by cancer cells | IFN-$\alpha$ | Singh et al. (1996) Proc. Natl. Acad. Sci. 92: 4562-4566. |

TABLE 2-continued

| Cancer-cell target | Pro-angiogenic proteins | Drug | Reference(s) |
|---|---|---|---|
| FGF receptor | FGF Receptor | SU11248; SU6668 | Tille t al. (2001) J. Pharmacol. Exp. Ther. 299: 1073-1086. |

In the clinic, antiangiogenic drugs are often combined with other therapeutic agents to achieve maximum therapeutic efficacy and/or to reduce drug toxicity, especially in the treatment of heterogenous diseases such as cancer.

Examples of such therapeutic agents that can be combined with antiangiogenic agents include, but are not limited to, alkylating agents, antibiotic agents, antimetabolic agents, hormonal agents, plant-derived agents, and biologic agents.

The alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death.

The antibiotic agents are a group of drugs that are produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death.

The antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), and asparaginase.

The hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. Biologic agents are a group of biomolecules that elicit cancer/tumor regression when used alone or in combination with chemotherapy and/or radiotherapy.

Examples of biologic agents include, but are not limited to, immuno-modulating proteins such as cytokines, monoclonal antibodies against tumor antigens, tumor suppressor genes, and cancer vaccines. Combination therapy including a camptothecin compound, gemcitabine and the biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon α (IFN-α) demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins include, but are not limited to, interleukin 2 (IL-2), and interleukin 4 (IL-4), interleukin 12 (IL-12).

Interferon α include more than 23 related subtypes with overlapping activities, all of the IFN-α subtypes within the scope of the present invention. IFN-α has demonstrated activity against many solid and hematologic malignancies, the later appearing to be particularly sensitive. Examples of interferons include, but are not limited to, interferon α interferon ∃ (fibroblast interferon) and interferon γ (fibroblast interferon).

Other cytokines include those cytokines that exert profound effects on hematopoiesis and immune functions. Examples of such cytokines include, but are not limited to erythropoietin (epoietin α), granulocyte-CSF (filgrastin), and granulocyte, macrophage-CSF (sargramostim).

Other immuno-modulating agents other than cytokines may also be used in conjunction with CPT and a COX-2 inhibitor to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

An example of monoclonal antibodies against tumor antigens is RITUXAN® (Rituximab) that is raised against CD20 on lymphoma cells and selectively deplete normal and malignant CD20+ pre-B and mature B cells. RITUXAN® is used as single agent for the treatment of patients with relapsed or refractory low-grade or follicular, CD20+, B cell non-Hodgkin's lymphoma.

Other examples of anti-cancer antibodies include, but are not limited to, MYLOTARG® (gemtuzumab ozogamicin) which is an monoclonal antibody approved for treating acute myeloid leukemia (AML), CAMPATH® (alemtuzumab) for B cell chronic lymphocytic leukemia, ZEVALIN® (ibritumomab yiuxetan) for non-Hodgkin's lymphoma (NHL), PANOREX® (edrecolomab) for colorectal cancer, BEXXAR® (tositumomab) for treating NHL, ERBITUX® (cetuximab) which is a monoclonal antibody targeting epidermal growth factor (EGF) and for treating various cancers, and pemtumomab for treating ovarian cancer.

Tumor suppressor genes are genes that function to inhibit the cell growth and division cycles, thus preventing the development of neoplasia. Mutions in tumor suppressor genes cause the cell to ignore one or more of the components of the network of inhibitory signals, overcoming the cell cycle check points and resulting in a higher rate of controlled cell growth—cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 are found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), α-fetoprotein (AFP), carcinoembryonic antigen (CEA) (produced by colon cancers and other adenocarcinomas, e.g. breast, lung, gastric, and pancreas cancer s), melanoma associated antigens (MART-1, gp100, MAGE 1,3 tyrosinase), papillomavirus E6 and E7 fragments, whole cells or portions/lysates of autologous tumor cells and allogeneic tumor cells.

An adjuvant may be used to augment the immune response to TAAs. Examples of adjuvants include, but are not limited to, bacillus Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

The following example serves to more fully describe the manner of using the above-described invention. It is understood that the example in no way serves to limit the scope of this invention, but rather is presented for illustrative purpose. All references cited herein are incorporated by reference in their entirety.

EXAMPLES

Sources of Materials Used in Examples

Antibodies specific for receptors, adaptor molecules, and normalization standards are obtained from commercial vendors, including Labvision, Cell Signaling Technology, and BD Biosciences. All cell lines were purchased from ATCC or Cambrex Bio Science Walkersvile, Inc. (Walkersville, Md.). All human snap-frozen tissue samples were purchased from either William Bainbridge Genome Foundation (Seattle, Wash.) or Bio Research Support (Boca Raton, Fla.) and were approved by Institutional Research Board (IRB) at the supplier.

Figure 11A:
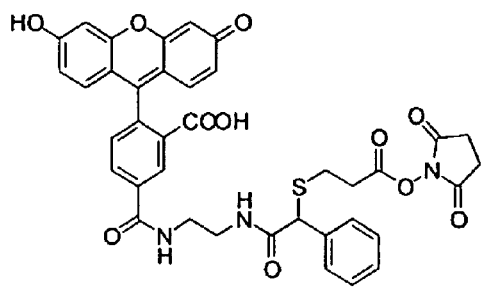
FIGS. 11A and 11B show formulas for NHS esters of various molecular tags used with the invention.
Figure 11A:
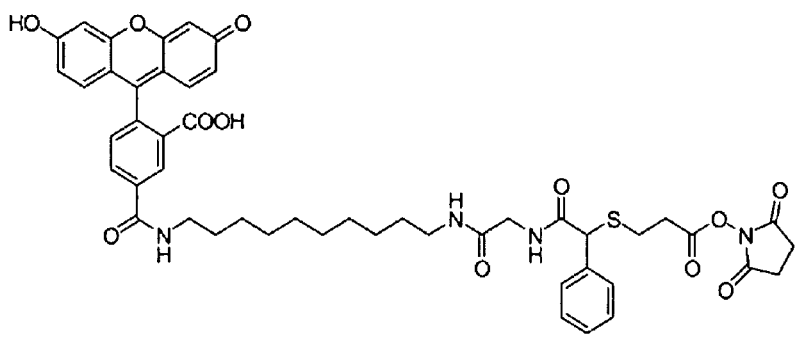
Figure 11A:
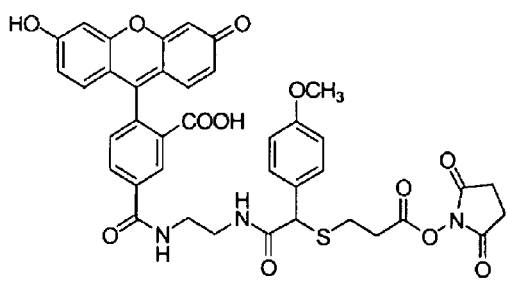
Figure 11A:
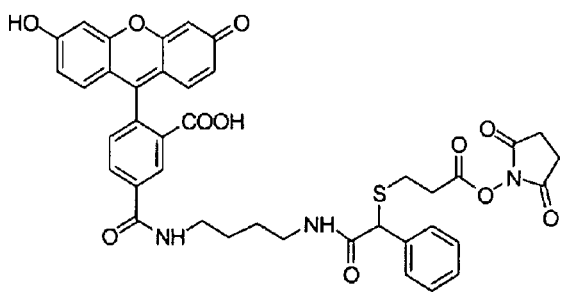
Figure 11B:
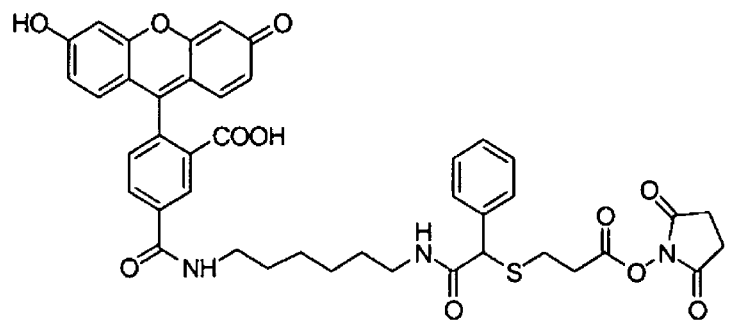
Figure 11B:
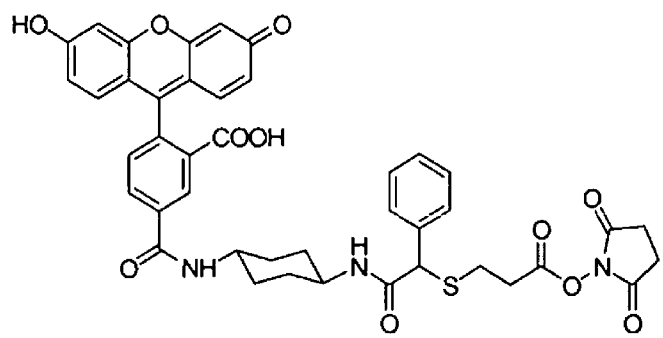
Figure 11B:
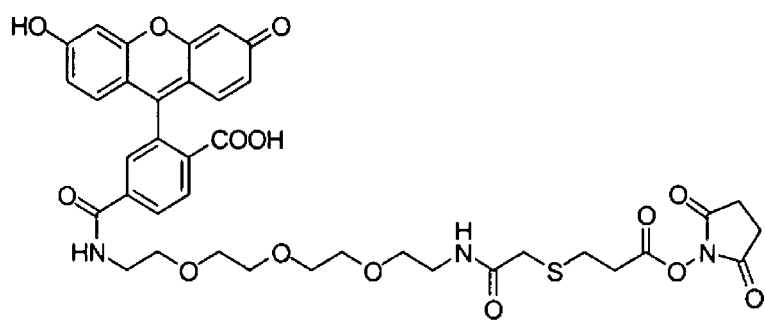

The molecular tag-antibody conjugates used below are formed by reacting NHS esters of the molecular tag with a free amine on the indicated antibody using conventional procedures. Molecular tags, identified below by their "Pro_N" designations, are either disclosed in the following references: Singh et al., U.S. patent publications, Nos. 2003/017915 and 2002/0013126, all of which are incorporated by reference, or their formulas are shown in FIGS. 11A and 11B. The latter molecular tags are synthesized and attached to binding compounds as taught in the two above references. Briefly, binding compounds below are molecular tag-monoclonal antibody conjugates formed by reacting an NHS ester of a molecular tag with free amines of the antibodies in a conventional reaction.

Example 1

Immunomagnetic Isolation of Human Endothelial Cells

Substantially pure CEC and CECP can be isolated by using the immunomagnetic isolation/enrichment technique described in Kinzler et al. (2000) Science 289:1197-1202. Briefly, the epithelial and hematopoietic cell fractions in the peripheral blood samples are sequentially removed via negative selection via antibody-linked magnetic beads (BerEP4 beads-Epithelial, CD45 beads-Pan leukocyte, CD64 beads-Macrophages, and CD14 beads-Monocytes). The remaining cells are stained with P1H12 antibodies and are isolated via positive selection with magnetic beads.

In this example, CEC and CECP were isolated by using a protocol modified from Voest et al. (2004) Annals of Oncology 15:139-145 as follows:

1) Magnetic beads (Dynal M450 IgG$_1$, Dynal AS, Oslo, Norway) were conjugated to a monoclonal antibody for CD146, MCAM, an endothelial cell surface junction protein.

2) Whole blood was diluted 1:3 with 0.9% NaCl and incubated for 30 min with 20 uL ($2.8 \times 10^6$) antibody-coupled magnetic beads at 4° C. on a roller bench.
3) Unbound cells were removed by magnetic separation using a MPC-L magnet (Dynal, AS)
4) The beads-bound cell fraction was rinsed with phosphate-buffered saline-bovine serum albumin (PBS-BSA 0.1%). Cells are now ready for lysis.

Human umbilical vein endothelial cells (HUVEC) were isolate from U937 by using CD146 conjugated magnetic beads following the protocols listed below.

Isolation of HUVEC from U937 using CD146 Conjugated Magnetic Beads

I. Wash Beads
1) Vortex to resuspend beads in storage buffer.
2) Pipette 350 uL beads (30 mg/mL) to 1.5 mL Tube.
3) Capture beads with magnet for 60 seconds. Remove supernatant.
4) Remove tube from magnet. Add 1.5 mL 0.1% BSA in PBS (pH 7.4).
5) Vortex to resuspend beads.
6) Capture beads with magnet for 60 seconds. Remove supernatant.
7) Repeat Steps 4-6. (Wash 1 more time with BSA/PBS).
8) Resuspend beads in 350 uL 0.1% BSA in PBS (pH 7.4).
9) Beads are 30 mg/mL final concentration.

II. Incubation of Sample
1) Add 25 uL beads to each cel mixture (1 mL cells/sample)
2) Incubate the sample for 30 min @ 4° C. with gentle rotation.
3) Add 500 uL PBS +0.1% BSA
4) Capture beads with magnet for 2 min. Remove supernatant.
5) Remove tube from magnet. Add 1.5 mL 0.1% BSA in PBS (pH 7.4).
6) Vortex to resuspend beads.
7) Capture beads with magnet for 2 min. Remove supernatant.
8) Repeat Steps 5-7. (Wash 3 more times with BSA/PBS).
9) After the 4th wash resuspend the beads in 100 uL freshly made Lysis Buffer.
10) Incubate on ice for 30 min.
11) Spin cells in microfuge at max rpm for 10 min.
12) Remove supernatant to new tube for assay or storage at −70° C.

Example 2

Lysis of CEC or CECP

The isolated CEC or CECP were lysed according to the following protocol:
Protocol
Step
1) Seed 2 15 cm dishes with $6 \times 10^6$ cells in 20 mL EGM
2) Prepare fresh lysis buffer
3) Starting now, always work on ice. Aspirate the medium.
4) Add 600 ul of fresh lysis buffer.
5) Swirl the plates to distribute the buffer evenly.
6) Scrap the cells.
7) Collect the crude lysate in 1.5-ml tube.
8) Wait for 30 min.
9) Spin down at 4 C at 14000 rpm for 10 min
10) Collect the supernatant in 1.5-ml new tube.
11) Store at −80 C for later use.

The lysis buffer was prepared by mixing the following reagents:

| Lysis buffer | | 10 ml | | |
|---|---|---|---|---|
| | Reagents | Stock con. | Final conc | Vol |
| 1) | 10% triton X-100 | 10 | 1 | 1.00 |
| 2) | 1M Tris pH 7.5 | 1 | 0.05 | 0.50 |
| 3) | 1M NaF | 1 | 0.05 | 0.50 |
| 4) | 5M NaCl | 5 | 0.1 | 0.20 |
| 5) | 2M B-Glycerolphosphate | 1 | 0.05 | 0.50 |
| 6) | 0.1M Na3VO4 | 0.1 | 0.001 | 0.10 |
| 7) | 1 mg/ml pepstatin | 1 | 0.01 | 0.10 |
| 8) | Complete mini protease | | | 1 tablet |
| 9) | 0.5M EDTA | 0.5 | 0.005 | 0.10 |
| | | | Total (ml) | 3.00 |
| | | | Water (ml) | 7.00 |

Example 3

Analysis of Cell Lysate for Protein Complexes of Angiogenic Receptors and Phosphorylation of Downstream Effector Proteins Protein complexes formed by angiogenic receptors (e.g., VEGFR, Tie), such as the homodimers and heterodimers formed by VEGFR, were measured in cell lysates from CEC, CECP, and cell lines such as human umbilical vein endothelial cells (HUVEC), and human vulval carcinoma cell line (A431). Measurements were made using three binding compounds and a cleaving probe by using the following protocol.
1) Add Lysis Buffer and Lysate into 96-well PCR plate to 30 uL final volume.
2) Add 5 uL antibody mix to each well.
3) Incubate reactions at RT for 2 hours on plate shaker.
4) Add 5 uL steptavidin-scissor mix to each well in dark room. Mix is 32.5×. Added 15 uL to 472.5 uL Dilution Buffer (1% BSA in PBS)
5) Incubate reactions at RT for 45 minutes on plate shaker in dark room.
6) Pre-wet 96-well 2 micron membrane filter plates with 100 uL Exchange Buffer I
7) Drain filter plate and add the 40 uL reactions in the dark room.
8) Drain the plate and add 150 uL Exchange Buffer I (1×PBS, 0.5% Triton 1000) per well.
9) Drain the plate and add 150 uL Exchange Buffer 11 (0.005 PBS) per well. Repeat this step one more time.
10) Drain the plate and add 30 uL Illumination Buffer (0.005 PBS) w/CE standard to each well.
11) Illuminate for 15 min at RT.
12) Transfer the entire reaction to clean 96-well PCR plate.
13) Aliquot 9 uL to CE plate and run.

Example 4

Analysis of Cell Lysates for VEGFR2 Homodimerization and Receptor Phosphorylation In this example, VEGFR2-VEGFR2 homodimers and phosphorylation states were measured in cell lysates from several cell lines after treatment with various concentrations of vascular endothelial growth factor (VEGF). Measurements were made using three binding compounds and a cleaving probe as described below.

Sample Preparation:
1. Serum-starve human umbilical vein endothelial cell line (HUVEC) culture overnight before use.
2. Stimulate cell lines with VEGF in culture media for a set period of time (1, 3, 5, 9, 14 minutes) at 37° C. Exemplary doses of VEGF are 0, 2, 10, 25, 50, 250, 1000 ng/mL.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.)
5. Collect supernatants as lysates and aliquot for storage at −80° C. until use.

Figure 7A:
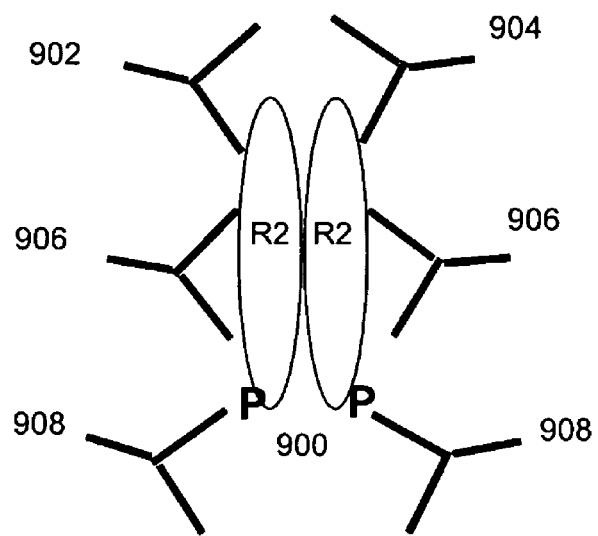
FIG. 7A illustrates diagrammatically an embodiment for measuring VEGFR2-VEGFR2 homodimers and VEGFR2 phosphorylation.

Assay:
Assay design: As illustrated diagrammatically in FIG. 7A, VEGFR2-VEGFR2 (R2-R2) homodimers (900) are quantified ratiometrically based on the binding of a cleaving probe (902), a first bind compound (904) which is specific for the same antigenic determinant on VEGFR2 as the cleaving probe, a second binding compound (906) which is specific for a different antigenic determinant on VEGFR2 from the cleaving probe, and a third binding compound (908) which is specific for phosphorylated tyrosine. A photosensitizer is attached to the cleaving probe (902) via an avidin-biotin linkage, and the first, second, and third binding compounds are labeled with molecular tags Pro10, Pro14, and Pro2, respectively.

The total assay volume was 40 ul. The lysate volume was adjusted to 30 ul with lysis buffer. The antibodies are diluted in lysis buffer up to 10 ul. Typically ~5000 to 15000 cell-equivalent of lysates is used per reaction. The detection limit is ~1000 cell-equivalent of lysates.

Procedure: Final concentrations of pre-mixed binding compounds (i.e. molecular tag- or biotin-antibody conjugates) in reaction:
Pro10_anti-VEGFR2: 0.25 ug/ml (VEGFR2 homodimer)
Pro14_anti-VEGFR2: 0.25 ug/ml (total VEGFR2)
Pro2_anti-phospho-Tyr: 0.0125 ug/ml (phosphorylation)
Biotin_anti-VEGFR2: 0.25 ug/ml
1. To assay 96-well, add 10 ul antibody mix to 30 ul lysate and incubate for 1 hour at RT.
2. Add 2 ul streptavidin-derivatized cleaving probe (final 2 ug/well) to assay well and incubate for 45 min.
3. Add 150 ul of wash buffer to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an ABI3100 CE instrument with a 22 cm capillary (injection conditions: 5 kV, 75 sec, 30° C.; run conditions: 425 sec, 30° C.).

Assay buffers are as follows:

| Lysis Buffer (made fresh and stored on ice) | | |
|---|---|---|
| Final | ul | Stock |
| 1% Triton X-100 | 1000 | 10% |
| 20 mM Tris-HCl (pH 7.5) | 200 | 1 M |
| 100 mM NaCl | 200 | 5 M |
| 50 mM NaF | 500 | 1 M |
| 50 mM Na beta-glycerophosphate | 1000 | 0.5 M |
| 1 mM Na$_3$VO$_4$ | 100 | 0.1 M |
| 5 mM EDTA | 100 | 0.5 M |
| 10 ug/ml pepstatin | 100 | 1 mg/ml |
| 1 tablet (per 10 ml) Roche Complete protease inhibitor (#1836170) | N/A | N/A |
| Water | 6500 | N/A |
| | 10 ml | Total |

| Wash buffer (stored at 4° C.) | | |
|---|---|---|
| Final | ml | Stock |
| 1% NP-40 | 50 | 10% |
| 1x PBS | 50 | 10x |
| 150 mM NaCl | 15 | 5 M |
| 5 mM EDTA | 5 | 0.5 M |
| Water | 380 | N/A |
| | 500 ml | Total |

| Illumination buffer: | | |
|---|---|---|
| Final | ul | Stock |
| 0.005x PBS | 50 | 1x |
| CE std | 3 | 100x |
| 10 mM Tris-HCl (pH 8.0) | | 0.1 M |
| 10 pM A160 | | 1 nM |
| 10 pM A315 | | 1 nM |
| 10 pM HABA | | 1 nM |
| Water | 10,000 | N/A |
| | 10 ml | Total |

Data Analysis:
1. Normalize relative fluorescence units (RFU) signal of each molecular tag against CE reference standard A315 (a fluorescein-derivatized deoxyadenosine monophosphate that has known peak position relative to molecular tags from the assay upon electrophoretic separation).
2. Subtract RFU of "no lysate" background control from corresponding molecular tag signals.
3. Report homodimerization of VEGFR2 as the corresponding RFU ratiometric to RFU from Pro14_anti-VEGFR2 from assay wells using biotin_anti-VEGFR2.
4. Report receptor phosphorylation for VEGFR2 as RFU from Pro2_PT100 anti-phospho-Tyr ratiometric to RFU from Pro14_anti-VEGFR2 from assay wells using biotin_anti-VEGFR2.

Figure 7B:
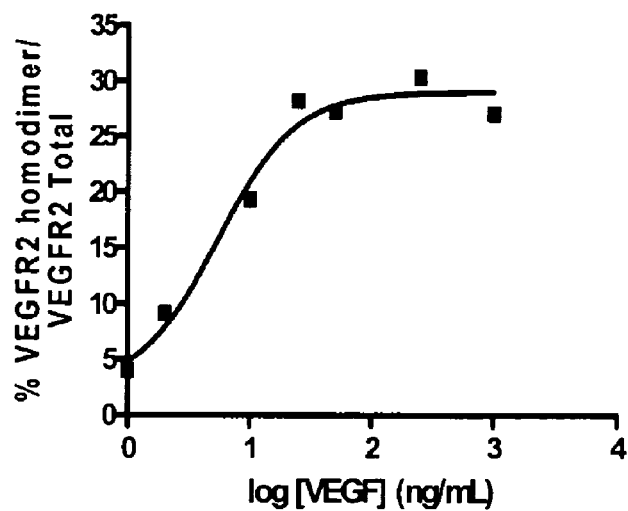
FIGS. 7B-D show measurements of VEGFR2-VEGFR2 homodimers and VEGFR2 phosphorylation in HUVEC cells in response to VEGF treatment.
Figure 7C:
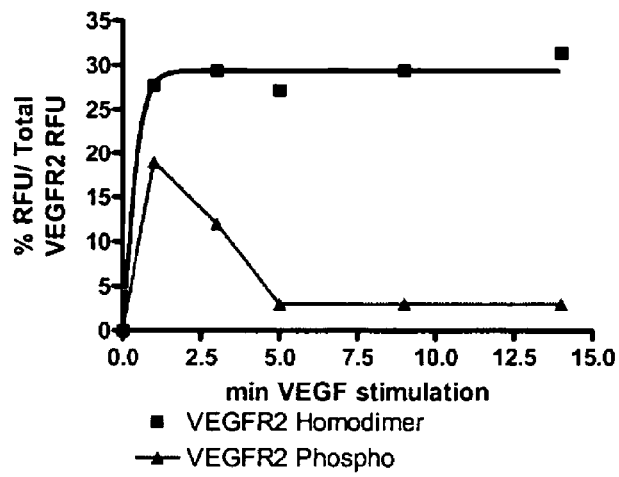
Figure 7D:
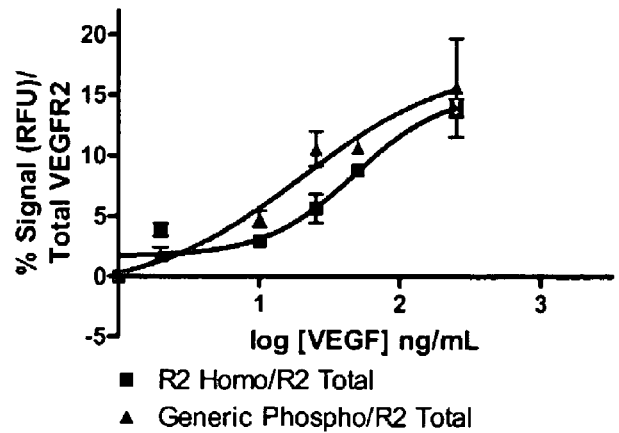

Results of the assays are illustrated in FIGS. 7B-D. FIG. 7B shows the quantity of VEGFR2-VEGFR2 homodimers increases on HUVEC cells with increasing concentrations of VEGF at a 5 min stimulation time. FIG. 7C shows VEGFR2-VEGFR2 homodimers form by 1 minute of VEGF stimulation, and remain after up to 14 minutes of stimulation. However VEGFR2 phosphorylation is transient, peaking at 1 minute of stimulation and decreasing to background level by 5 minutes.

FIG. 7D shows the quantity of VEGFR2-VEGFR2 homodimers and VEGFR2 phosphorylation increases on HUVEC cells with increasing concentrations of VEGF at a 1 min stimulation time.

Example 5

Analysis of Cell Lysates for Tie2 Homodimerization

In this example, Tie2-Tie2 homodimers were measured in cell lysates from several cell lines after treatment with various concentrations of angiopoietin-1 (Ang-1). Measurements were made using three binding compounds and a cleaving probe as described below.

Sample Preparation:
1. Serum-starve human umbilical vein endothelial cell line (HUVEC) culture overnight before use.
2. Stimulate cell lines with 200 ng/mL Ang-1 in culture media for a set period of time (10, 30 minutes) at 37° C.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.)
5. Collect supernatants as lysates and aliquot for storage at −80° C. until use.

Assay:
Assay design: As illustrated diagrammatically in FIG. 4C, Tie2-Tie2 homodimers are quantified ratiometrically based on the binding of cleaving probe (134) and binding compounds (130), and (132). A photosensitizer indicated by "PS" is attached to cleaving probe (134) via an avidin-biotin linkage, and binding compounds (130), and (132) are labeled with molecular tags Pro10, and Pro14, respectively.

The total assay volume was 40 ul. The lysate volume was adjusted to 30 ul with lysis buffer. The antibodies were diluted in lysis buffer up to 10 ul. Typically ~5000 to 15000 cell-equivalent of lysates was used per reaction. The detection limit was ~1000 cell-equivalent of lysates.

Procedure: Final concentrations of pre-mixed binding compounds (i.e. molecular tag- or biotin-antibody conjugates) in reaction:
Pro10_anti-Tie2: 0.25 ug/ml (Tie2 homodimer)
Pro14_anti-Tie2: 0.25 ug/ml (total Tie2)
Biotin_anti-Tie2: 0.25 ug/ml
1. To assay 96-well, add 10 ul antibody mix to 30 ul lysate and incubate for 1 hour at RT.
2. Add 2 ul streptavidin-derivatized cleaving probe (final 2 ug/well) to assay well and incubate for 45 min.
3. Add 150 ul of wash buffer to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an ABI3100 CE instrument with a 22 cm capillary (injection conditions: 5 kV, 75 sec, 30° C.; run conditions: 425 sec, 30° C.).

Assay buffers are as previously described.

Data Analysis:
1. Normalize relative fluorescence units (RFU) signal of each molecular tag against CE reference standard A315 (a fluorescein-derivatized deoxyadenosine monophosphate that has known peak position relative to molecular tags from the assay upon electrophoretic separation).
2. Subtract RFU of "no lysate" background control from corresponding molecular tag signals.
3. Report homodimerization of Tie2 as the corresponding RFU ratiometric to RFU from Pro14_anti-Tie2 from assay wells using biotin_anti-Tie2.

Figure 8A:
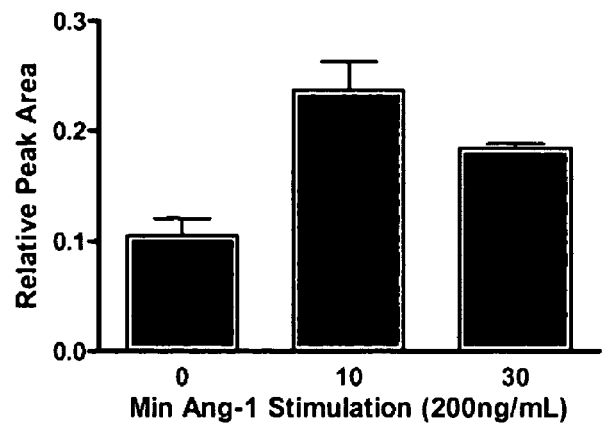
FIGS. 8A-B show measurements of Tie2-Tie2 homodimer and Tie2 in HUVEC cells in response to Ang-1 treatment.
Figure 8B:
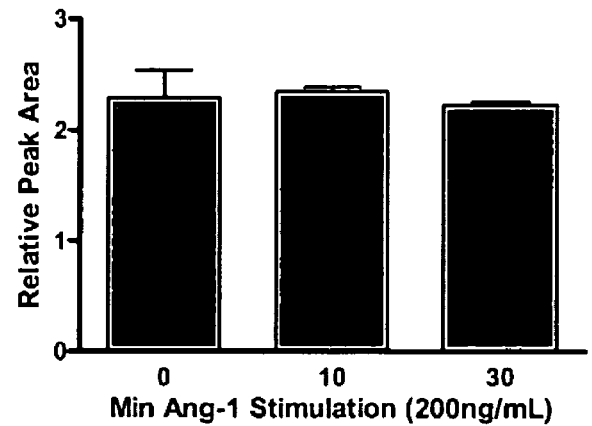

Results of the assays are illustrated in FIGS. 8A and 8B. FIG. 8A shows the quantity of Tie2-Tie2 homodimers increase on HUVEC cells with 200 ng/mL of Ang-1 at 10 min of stimulation, and decreases from that level after 30 min Ang-1 stimulation. FIG. 8B shows that the total amount of Tie2 receptor on the HUVEC cell does not change with Ang-1 treatment.

Example 6

Analysis of Cell Lysates for VEGFR2 after Endothelial Cell Isolation

Sample Preparation:
1. Magnetic beads (Dynal M450 IgG$_1$, Dynal AS, Oslo, Norway) were conjugated to a monoclonal antibody for CD146, MCAM, an endothelial cell surface junction protein.
2. HUVEC are removed from cell culture flask by trypsin-EDTA treatment and re-suspended in PBS containing 0.1% BSA.
3. U937 (human histiocytic lymphoma cell line) cells in culture are spun down in a centrifuge and re-suspended in PBS containing 0.1% BSA.
4. Mixtures of HUVEC and U-937 were made with a final number of cells being 2,000,000 cells/mixture. The percent concentration of HUVEC to U-937 respectively varied from 100/0, 90/10, 75/25, 50/50, 25/75, 10/90, 1/99, 0.1/99.9, 0.01/99.99, 0.001/99.999, 0/100.
5. Half of each of the cell mixtures (1,000,000 cells) were simply spun in a microfuge and lysed using previously described protocol in 100 uL freshly made lysis buffer.
6. The CD146-conjugated beads are added to the other half of cell mixtures at 750 ug/mL. The cells are then incubated for 30 min at 4° C. rotating gently.
7. Unbound cells are removed using magnetic separation using Dynal MPC-L magnet.
8. Bound cells are washed 4 times with PBS containing 0.1% BSA.
9. After the 4$^{th}$ wash resuspend cells in 100 uL freshly made lysis buffer and lysed using previously described protocol.
10. Bicinchoninic acid (BCA) (Pierce cat # 23225) is used to quantify the protein concentration of each lysate.

Assay:
Assay design: VEGFR2 receptors are quantified ratiometrically based on the binding of cleaving probe and a binding compound. A photosensitizer indicated by "PS" is attached to cleaving probe via an avidin-biotin linkage, and the binding compound is labeled with molecular tag Pro14.

The total assay volume was 40 ul. The lysate volume was adjusted to 30 ul with lysis buffer. The antibodies were diluted in lysis buffer up to 10 ul. Typically ~5000 to 15000 cell-equivalent of lysates was used per reaction. The detection limit was ~1000 cell-equivalent of lysates.

Procedure: Final concentrations of pre-mixed binding compounds (i.e. molecular tag- or biotin-antibody conjugates) in reaction:
Pro14_anti-VEGFR2: 0.25 ug/ml (total VEGFR2)
Biotin_anti-VEGFR2: 0.25 ug/ml
1. To assay 96-well, add 10 ul antibody mix to 30 ul lysate and incubate for 1 hour at RT.
2. Add 2 ul streptavidin-derivatized cleaving probe (final 2 ug/well) to assay well and incubate for 45 min.
3. Add 150 ul of wash buffer to 96-well filter plate (Millipore MAGVN2250) and incubate for 1 hr at RT for blocking.
4. Empty filter plate by vacuum suction. Transfer assay reactions to filter plate and apply vacuum to empty.

5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an ABI3100 CE instrument with a 22 cm capillary (injection conditions: 5 kV, 75 sec, 30° C.; run conditions: 425 sec, 30° C.).

Assay buffers are as previously described:

Data Analysis:
1. Normalize relative fluorescence units (RFU) signal of each molecular tag against CE reference standard A315 (a fluorescein-derivatized deoxyadenosine monophosphate that has known peak position relative to molecular tags from the assay upon electrophoretic separation).
2. Subtract RFU of "no lysate" background control from corresponding molecular tag signals.

Figure 9A:
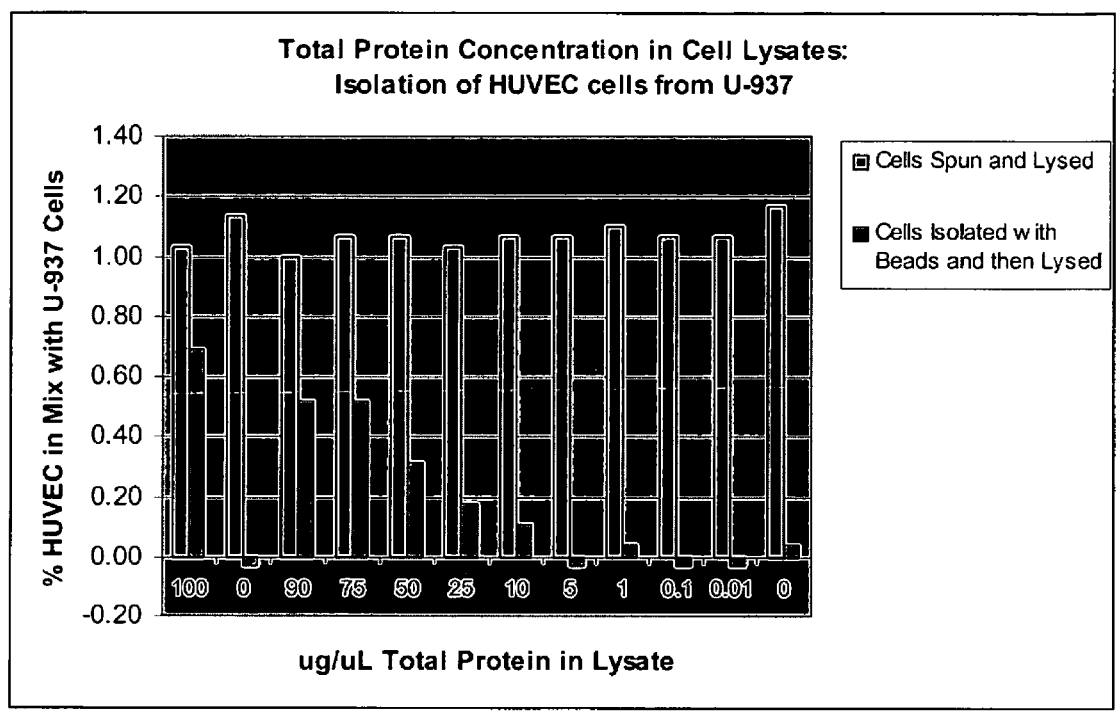
FIGS. 9A-B show measurements of VEGFR2 in HUVEC cells isolated from a mixture U-937 and HUVEC cells.
Figure 9B:
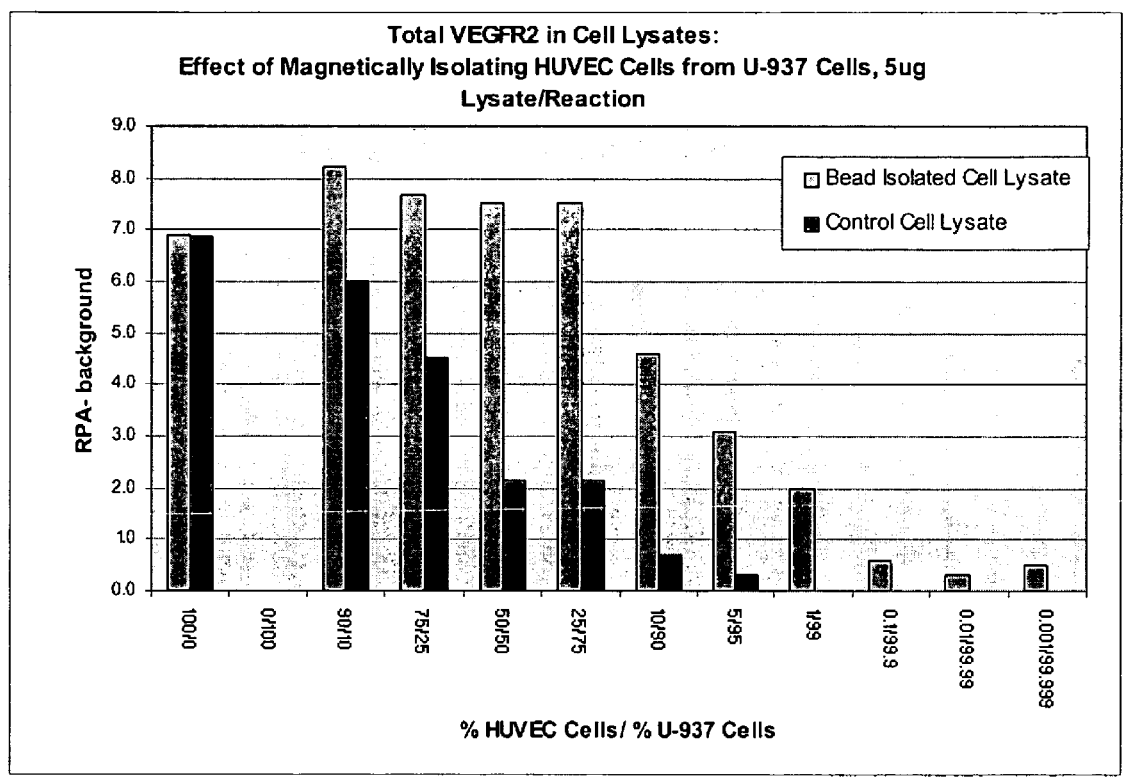

Results of the assays are illustrated in FIGS. 9A and 9B. FIG. 9A shows the protein concentration of the lysates. The data shows a clear trend of lower protein concentrations correlating with higher concentrations of U-937 cells in the isolated cell lysates. Conversely the higher concentration of HUVEC in the mixture results in a higher protein concentration in the lysates made from cells that have been immunogenically isolated. Lysates that have not been magnetically isolated show no change in protein concentration, as expected. FIG. 9B shows the presence of VEGFR2 receptors in the cell mixtures in 5 ug of lysate. The 100/0 and 0/100 HUVEC/U-937 columns clearly show that VEGFR2 is only expressed in HUVEC cells, and not in U-937 cells. This ensures that the VEGFR2 seen in other mixtures come exclusively from HUVEC. Isolation of endothelial cells enhances the sensitivity of VEGFR2 assay from 50,000 cells/assay to 2,000-5,000 cells/assay. This is a 10-25 fold increase in sensitivity.

Example 7

Analysis of Cell Lysates for Erk, BAD, and RSK Phosphorylation

As shown in FIG. 3, in response to VEGF, phosphorylation of various proteins downstream of the VEGFR2 pathways (e.g., MEK, Erk, RSK, BAD, and Akt) is increased. In this example, Erk, BAD and RSK phosphorylation states were measured in cell lysates from several cell lines after treatment with various concentrations of vascular endothelial growth factor (VEGF). Measurements were made using two binding compounds and a cleaving probe for each target protein as described below.

Sample Preparation:
1. Serum-starve human umbilical vein endothelial cell line (HUVEC) culture overnight before use.
2. Stimulate cell lines with VEGF in culture media for a set period of time (1, 3, 5, 9, 14 minutes) at 37° C. Exemplary doses of VEGF are 0, 2, 10, 25, 50, 250, 1000 ng/mL.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.)
5. Collect supernatants as lysates and aliquot for storage at −80° C. until use.

Assay:
Assay design: Erk, BAD and RSK phosphorylation states are quantified ratiometrically based on the binding of a cleaving probe and two binding compounds. A photosensitizer is attached to the cleaving probe via an avidin-biotin linkage, and two binding compounds are labeled with molecular tags Pro44 and Pro32 for targeting Erk, Pro52 and Pro46 for targeting BAD, or Pro36 and Pro53 for targeting RSK.

The total assay volume was 40 ul. The lysate volume was adjusted to 30 ul with lysis buffer. The antibodies were diluted in lysis buffer up to 10 ul. Typically ~5000 to 15000 cell-equivalent of lysates was used per reaction. The detection limit was ~1000 cell-equivalent of lysates.

Procedure: Final concentrations of pre-mixed binding compounds (i.e. molecular tag- or biotin-antibody conjugates) in reaction:
biotin_anti-Erk, 20 nM
Pro44_anti-Erk (Total), 5 nM
Pro32_anti-phospho-Erk (Phosphorylation), 5 nM
biotin_anti-BAD, 20 nM
Pro52_anti-BAD (Total), 5 nM
Pro46_anti-Phospho-BAD (Phosphorylation), 5 nM
Biotin_anti-RSK, 20 nM
Pro36_anti-RSK (Total), 5 nM
Pro53_anti-phospho-RSK (Phosphorylation), 5 nM 1. Prime the filter plate (Millipore MAGVN2250) with 50 µl of Assay Buffer.
2. Add 20 µl of Antibody mixture.
3. Add 10 µl of Lysate and incubate for 1 h
4. Add 2 µg streptavidin-derivatized cleaving probe to each assay well, and incubate for another 30 min.
5. Empty filter plate by vacuum suction.
6. Add 200 µl of Wash buffer and empty filter plate by vacuum suction.
7. Repeat step 6 one more time.
8. Add 50 µl of illumination buffer containing CE standard.
9. Illuminate the plate for 10 min.
10. Transfer 20 µl to the 96 well plates and run CE using ABI-3100.

Assay buffers are as previously described.

Data Analysis:
1. Normalize relative fluorescence units (RFU) signal of each molecular tag against CE reference standard A315 (a fluorescein-derivatized deoxyadenosine monophosphate that has known peak position relative to molecular tags from the assay upon electrophoretic separation).
2. Subtract RFU of "no lysate" background control from corresponding molecular tag signals.
3. Report phosphorylation of Erk as the corresponding RFU ratiometric to RFU from Pro44_anti-Erk from assay wells using biotin_anti-Erk.
4. Report phosphorylation of RSK as the corresponding RFU ratiometric to RFU from Pro36_anti-RSK from assay wells using biotin_anti-RSK.
5. Report phosphorylation of BAD as the corresponding RFU ratiometric to RFU from Pro52_anti-BAD from assay wells using biotin_anti-BAD.

Figure 10A:
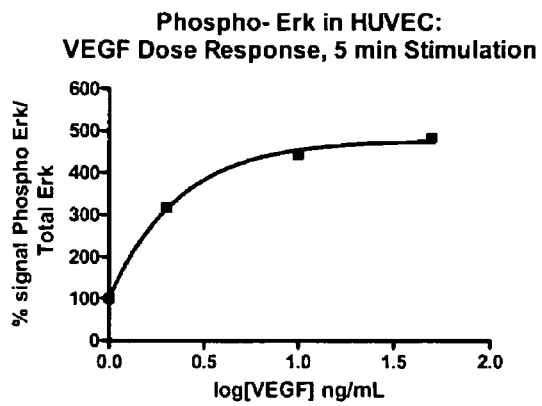
FIGS. 10A, 10B, and 10C show measurements of phosphorylation of Erk, RSK, and BAD respectively in HUVEC cells in response to VEGF treatment.
Figure 10B:
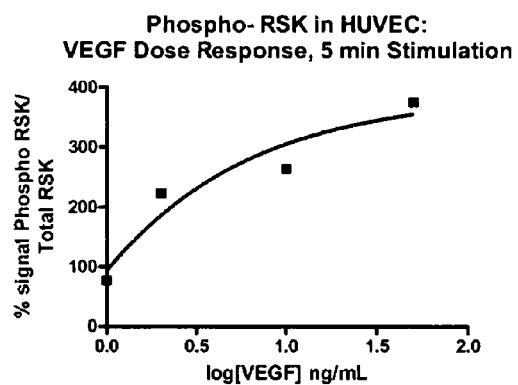
Figure 10C:
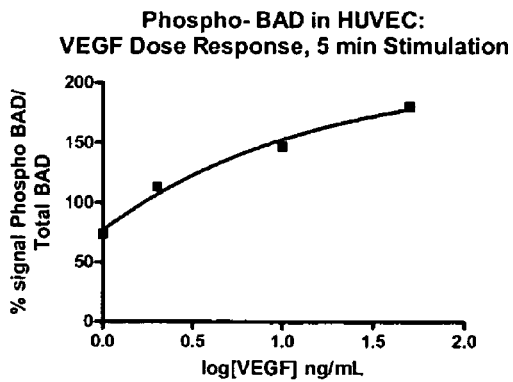

Results of the assays are illustrated in FIGS. 10A, 10B and 10C. FIGS. 10A, 10B, and 10C show that the phosphorylation state of Erk, RSK, and BAD respectively increases on HUVEC cells with increasing concentrations of VEGF at a 5 min stimulation time. It was also found that phosphorylation of Akt increased on HUVEC cells with increasing concentrations of VEGF (data not shown).

Example 8

Analysis of Expression of Angiogenic Genes and Proteins in Endothelial and Cancer Cell Lines In this example, expression of angiogenic genes and proteins in endothelial and cancer cell lines was analyzed by using a Taqman assay and an assay using releasable molecular tags similar to the one in Example 3.

Example 9

Analysis of Gene and Protein Expression of Receptors in Endothelial and Cancer Cell Lines In this example gene and protein expression of receptors were measured in primary endothelial cell lines and human cancer cell lines. Gene expression data was obtained using real-time quantitative PCR (Taqman Assay), and protein expression was determined using the binding compounds and cleaving probes as described below. Genes assayed were VEGFR2, VEGFR1, Tie2, Her1, Her2, Her3, VEGFR3, PDGFRA, PDGFRB, Tie1, FGFR1, FGFR2, FGFR3, FGFR4, EphA1, EphA2, EphA3, EphA4, EphA5, EphA7, EphA8, EphB1, and EphB2. Proteins assayed were VEGFR2, VEGFR1, Tie2, Her1, Her2, and Her3.

Sample Preparation:

Primary endothelial cell lines were obtained from Cambrex Bio Science Walkersville, Inc. and were propagated in growth media as per manufacturer's recommendations. The endothelial cell lines were Human Umbilical Vein Endothelial Cells (HUVEC), Human Micro-Vascular Endothelial Cells, Dermal (HMVEC-d), Human Pulmonary Artery Endothelial Cells (HPAEC), and Human Micro-Vascular Endothelial Cells, Lung (HMVEC-L). The cancer cell lines tested were MCF7 and SKBR3 (human breast cancer cells), and 22RV1 (human prostate cancer cells), and were propagated per ATCC instructions in growth media.

RNA was isolated from the cells for gene expression profiling using TRIzol® Reagent (Invitrogen) following manufacturer's protocol.

Cells were lysed for protein expression profiling as follows.

1. Aspirate culture media, transfer onto ice, and add lysis buffer to lyse cells in situ.
2. Scrape and transfer lysate to microfuge tube. Incubate on ice for 30 min. Microfuge at 14,000 rpm, 4° C., for 10 min. (Centrifugation is optional.)
3. Collect supernatants as lysates and aliquot for storage at −80° C. until use.

Assay:

Gene Expression Assay design: Pre-developed Taqman probes were purchased from Applied BioSystems. Assays were performed on 5 ng of total RNA as per manufacturer's recommendations. Briefly, 10× primer-probe mix (ABI), RNA, and 2× Quantitect Probe RT-PCR Master Mix (Qiagen), 100× Quantitect RT Mix, and H$_2$O were combined to a final volume of 25 ul. Cycling conditions were 30 min at 48° C., 10 min at 95° C., and 40 cycles of 15 sec at 95° C. and 1 min at 60° C. Samples were run on the DNA Engine Opticon (MJ Research).

Protein Assay design: Receptors were quantified ratiometrically based on the binding of a cleaving probe and a binding compound. A photosensitizer is attached to the cleaving probe via an avidin-biotin linkage, and the binding compound is labeled with molecular tag Pro14.

The total assay volume was 40 ul. The lysate volume was adjusted to 30 ul with lysis buffer. The antibodies were diluted in lysis buffer up to 10 ul. Typically ~5000 to 15000 cell-equivalent of lysates was used per reaction. The detection limit is ~1000 cell-equivalent of lysates.

Procedure: Final concentrations of pre-mixed binding compounds (i.e. molecular tag- or biotin-antibody conjugates) in reaction:

Pro11_anti-VEGFR1: 0.25 ug/ml (total VEGFR1)
Biotin_anti-VEGFR1: 0.25 ug/ml
Pro14_anti-VEGFR2: 0.25 ug/ml (total VEGFR2)
Biotin_anti-VEGFR2: 0.25 ug/ml
Pro10_anti-Tie2: 0.25 ug/ml (total Tie2)
Biotin_anti-Tie2: 0.25 ug/ml
Pro10_anti-Her1: 0.1 ug/ml (total Her1)
Biotin_anti-Her1: 2 ug/ml
Pro14_anti-Her2: 0.1 ug/ml (total Her2)
Biotin_anti-Her2: 2 ug/ml
Pro99_anti-Her3: 0.1 ug/ml (total Her3)
Biotin_anti-Her3: 2 ug/ml 1. To assay 96-well, add 10 ul antibody mix to 30 ul lysate and incubate for 1 hour at RT.
2. Add 2 ul streptavidin-derivatized cleaving probe (final 2 ug/well) to assay well and incubate for 45 min.
3. Add 150 ul of wash buffer to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an ABI3100 CE instrument with a 22 cm capillary (injection conditions: 5 kV, 75 sec, 30° C.; run conditions: 425 sec, 30° C.).

Assay buffers are as previously described.

Data Analysis:

Gene Expression

1. The Cycle Threshold line was set using the Opticon Monitor software. The cycle number at which the fluorescent signal from cleaved signal probes crosses the threshold line is known as the Cycle Threshold (C(t)).

Protein Expression

1. Normalize relative fluorescence units (RFU) signal of each molecular tag against CE reference standard A315 (a fluorescein-derivatized deoxyadenosine monophosphate that has known peak position relative to molecular tags from the assay upon electrophoretic separation).
2. Subtract RFU of "no lysate" background control from corresponding molecular tag signals.

Results of the assays are summarized in Tables 3 and 4. Gene expression values were split into 3 categories: "+", which indicates a clear presence of a gene (C(t) of <32), "Low" which indicates a C(t) of 32-38, and "−" which indicates no gene detected (C(t) >38). Detection of a protein that has a signal above background level is represented in the table as a "+" and no protein detected is represented as a "−". "NT" indicates a sample was not tested. Of interest is the expression of VEGFR1, VEGFR2, and Tie2 (all of which are endothelial markers) in endothelial cells and not in the cancer cells.

TABLE 3

| Cell Line | VEGFR2 Gene | VEGFR2 Protein | VEGFR1 Gene | VEGFR1 Protein | Tie2 Gene | Tie2 Protein | Her1 Gene | Her1 Protein | Her2 Gene | Her2 Protein | Her3 Gene | Her3 Protein | VEGFR3 Gene | PDGFRA Gene | PDGFRB Gene | Tie1 Gene |
|---|---|---|---|---|---|---|---|---|---|---|---|---|---|---|---|---|
| HUVEC | + | + | + | - | + | + | + | + | + | + | + | + | + | - | - | + |
| HMVEC-d | + | + | Low | - | Low | - | + | NT | + | NT | + | NT | - | Low | + | - |
| HPAEC | + | + | + | - | + | + | + | NT | + | NT | + | NT | Low | - | - | + |
| HMVEC-L | + | + | + | - | + | + | + | NT | + | NT | - | NT | + | - | - | + |
| MCF-7 | Low | NT | - | NT | - | NT | + | + | + | + | + | + | Low | - | - | - |
| 22RV-1 | - | NT | - | NT | - | NT | + | + | + | + | + | + | Low | - | - | - |
| SKBR3 | - | NT | - | NT | - | NT | + | + | + | + | + | + | - | - | - | - |

TABLE 4

| Cell Line | FGFR1 Gene | FGFR2 Gene | FGFR3 Gene | FGFR4 Gene | EphA1 Gene | EphA2 Gene | EphA3 Gene | EphA4 Gene | EphA5 Gene | EphA7 Gene | EphA8 Gene | EphB1 Gene | EphB2 Gene |
|---|---|---|---|---|---|---|---|---|---|---|---|---|---|
| HUVEC | + | - | Low | Low | - | + | - | + | Low | - | - | Low | + |
| HMVEC-d | + | - | Low | Low | - | + | Low | Low | + | - | - | - | + |
| HPAEC | + | - | - | Low | - | + | - | + | - | - | - | Low | + |
| HMVEC-L | + | - | - | Low | - | + | - | + | Low | - | - | Low | + |
| MCF-7 | + | + | + | + | + | + | Low | + | - | + | - | Low | + |
| 22RV-1 | + | - | + | + | + | + | + | Low | Low | + | - | - | Low |
| SKBR3 | + | + | + | + | + | + | - | + | - | - | - | - | Low |

Example 10

Parallel Analysis of VEGFR2 Homodimerization in Cell Lysate and FFPE Samples

In this example, a parallel analysis of VEGFR2-VEGFR2 homodimers states were measured in cell lysates and formalin-fixed paraffin embedded ("FFPE") samples from the same treated and untreated human umbilical vein endothelial cells (HUVEC). This results presented herein demonstrate that VEGFR2 homodimers can be detected in cell lysate or FFPE sample format. Measurement was done following the protocol described below.

Sample Preparation:
1. Seed 6e+6 human umbilical vein endothelial cell line (HUVEC) in 15 cm cell culture dish. Seed a total of 22 plates.
2. Serum-starve human umbilical vein endothelial cell line (HUVEC) culture overnight before use. 2 plates will be used for harvesting stimulated and unstimulated cell lysate. 20 plates will be used for harvesting stimulated and unstimulated cell pellet for FFPE block.
3. Stimulate cell line with either 0 ng/ml or 500 ng/ml of VEGF in 1.5% FBS culture media for 1 minute. Stimulate one plate at a time.
4. Aspirate culture media, transfer onto ice, wash cells with 20 ml 1×PBS. For cell lysate, add 1 ml of lysis buffer to lyse cells in situ.
5. Scrape and transfer lysate to microfuge tube. Incubate on ice for 30 min. Microfuge at 14,000 rpm, 4° C., for 10 min.
6. Collect supernatants as lysates and aliquot for storage at −80° C. until use.
7. For FFPE block, aspirate culture media, transfer onto ice, wash cells with 20 ml 1×PBS and add 1 ml of 10% neutral buffered formalin to cells.
8. Scrape and transfer cells to 15 ml tube. Combine all stimulated HUVEC in one tube and unstimulated HUVEC in another tube. Formalin fixed cells at 4° C. for 16 hours. Spin cell at 3000 rpm at 4° C. for 5 min prior to FFPE block processing step.
9. Use Tissue-Tek automatic processor for processing the sample. Hydrate each formalin fixed sample using a series of alcohols with increasing concentration followed by treatment with Clear-rite (Xylene substitute) and paraffin.
10. Embed processed samples in a paraffin block using paraffin embedding station.
11. Cut 7 micron section and place on positively-charged glass slide, air dry at RT for 1 hour and heat slide in dry oven at 60° C. for 1 hour.

Assay:
Lysate assay: Assay performed as illustrated in example 4.
FFPE Assay:
1. Treat FFPE sections with 2× xylene, 2×100% ethanol, 2×70% ethanol, 2× water to remove the paraffin and rehydrate the sample.
2. Treat hydrated sections with protease 1 for 4 minutes at 37° C. to retrieval the epitope.
3. Block each section with 50 ul of 1.5% BSA blocking buffer for 1 hour. Aspirate blocking buffer, add 30 ul of antibody mix to each section and incubation overnight at 4° C. with shaking.
4. Wash each section with 50 ul of 1×PBST (1×PBS with 0.25% Triton-x-100) twice and follow by 1×PBS.
5. Aspirate 1×PBS, incubate each section with 30 ul of 2.5 ug/ml of streptavidin-scissor mix for 1 hour in dark.
6. Rinse slides with 3× water. Add 30 ul of illumination buffer to each section and illuminate for 2 hours at 4° C.
7. Following illumination, incubate slides are RT for 1 hour.
8. Remove illumination buffer from each section and analyze sample on CE instrument.

antibody conjugates in reaction:
Pro10_anti-VEGFR2: 2 ug/ml (VEGFR2 homodimer)
Biotin_anti-VEGFR2: 2 ug/ml (VEGFR2 homodimer)

Figure 12:
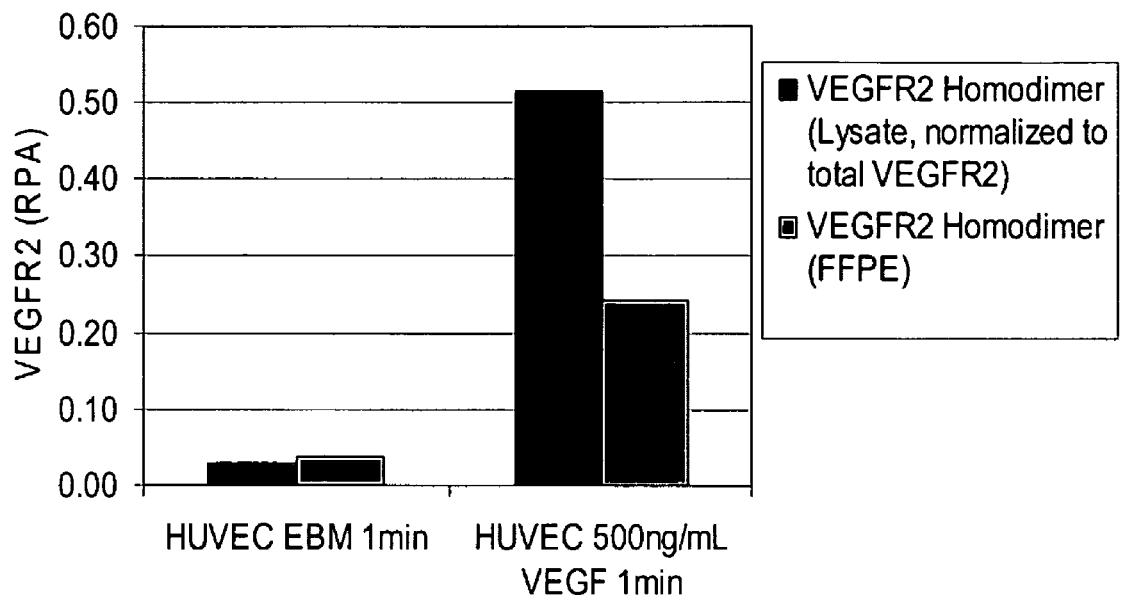
FIG. 12 shows measurement of VEGFR2-VEGFR2 homodimers in HUVEC cell lysate and in formalin-fixed paraffin embedded ("FFPE") samples.

Results of the comparison between lysate and FFPE assays are shown in FIG. 12. In the absence of VEGF stimulation, only basal levels of dimerization were detected in both formats. With VEGF stimulation both assays successfully detected a large increase in VEGFR2 homodimerization.

Example 11

Analysis of Xenograft Tissue Lysates for Total VEGFR2 Receptor and Homodimerization In this example, total VEGFR2 and VEGFR2 homodimerization was measured in mouse-human xenograft tissue created using a variety of human cell lines, including DU145, H522, H441, BT474, CALU-3, A549, MDA-MB-231, A431, H460, OVCAR-3 and HCT116. As controls, lysates of unstimulated and VEGF-stimulated HUVEC cultures were prepared. Measurements were made using two binding compounds and a cleaving probe as described below.

Because xenograft lysates potentially contained human and mouse forms of VEGFR2, an ELISA was performed to confirm that the VEGFR2 detected in this assay came from the human cells, and not mouse cells. It would be expected that the anti-VEGFR2 antibodies used here would react with human but not mouse VEGFR2 as the antibodies were raised in mice against recombinant human VEGFR2. In a 96-well plate, dilutions of recombinant mouse VEGFR2/Fc chimera (R&D Systems) or human VEGFR2/Fc chimera (R&D Systems) were made from 200 ng to 0.3 ng per well in phosphate buffered saline (PBS). Extra wells were included as protein-free controls. The proteins were allowed to adsorb for 1 hour at room temperature. The plates were blocked for 1 hour with 0.05% Tween 20 in PBS and then probed with the same 1 ug/ml Biotin_anti-VEGFR2 as used above. Following washes with 0.05% Tween 20 in PBS, retained Biotin_anti-VEGFR2 was detected with streptavidin-linked horseradish peroxidase followed by application of a chromogenic substrate that absorbs light at 460 nm. As shown in FIG. 12A, the cleaving probe was specific to human VEGFR2.

Control Sample Preparation:
1. Serum-starve human umbilical vein endothelial cell line (HUVEC) culture overnight before use.
2. Stimulate cell lines for 1 minute with media pre-warmed to 37° C. containing either or 200 ng/mL VEGF or no VEGF.
3. Aspirate culture media, transfer onto ice, and add cold lysis buffer to lyse cells in situ.
4. Scrape and transfer lysate to microfuge tube. Incubate on ice for 30 minutes.
5. Centrifuge at 14,000 rpm, 4° C., for 10 minutes.
6. Collect supernatants as lysates and aliquot for storage at −80° C. until use.

Tissue Preparation:
1. Finely mince tissue using razor blades.
2. Mix with 0.5-1 ml lysis buffer per 1 g tissue.
3. Further disrupt tissue with homogenizer using brief pulses.
4. Incubate on ice for 30 minutes.
5. Centrifuge at 14,000 rpm, 4° C., for 10 minutes.
6. Collect supernatants as lysates and aliquot for storage at −80° C. until use.

Assay:
The assay design was similar to that of Example 4, illustrated in FIG. 7A. VEGFR2-VEGFR2 (R2-R2) homodimers (900) were quantified based on the binding of a cleaving probe (902), a first binding compound (904) which was specific for the same antigenic determinant on VEGFR2 as the cleaving probe and a second binding compound (906) which was specific for a different antigenic determinant on VEGFR2 from the cleaving probe. A photosensitizer was attached to the cleaving probe (902) via an avidin-biotin linkage, and the first and second binding compounds were labeled with molecular tags Pro10 and Pro14, respectively.

The assay was run on serial dilutions of the lysate, typically from ~50 ug protein to ~0.5 ug plus a zero-protein control. Protein in each lysate sample was determined by a bicinchoninic assay (Pierce Biotechnology) against an albumin standard. The total assay volume was 40 ul. The lysate volume was adjusted to 30 ul with lysis buffer. The antibodies were diluted in lysis buffer to 5 ul. The streptavidin-derivatized cleaving probe was also diluted in lysis buffer to 5 ul.

Procedure: Final concentrations of pre-mixed binding compounds (i.e. molecular tag- or biotin-antibody conjugates) in reaction:
Pro10_anti-VEGFR2: 1.0 ug/ml (VEGFR2 homodimer)
Pro 14_anti-VEGFR2: 1.0 ug/ml (total VEGFR2)
Biotin_anti-VEGFR2: 1.0 ug/ml
9. In a 96-well assay plate, add 5 ul antibody mix to each 30 ul lysate and incubate for 1 hour at RT.
10. Add 5 ul streptavidin-derivatized cleaving probe (final 2.5 ug/well) to assay well and incubate for 45 min.
11. Add 150 ul of wash buffer to 96-well filter plate (Millipore MAGVN2250) and incubate for 1 hr at RT for blocking.
12. Empty filter plate by vacuum suction. Transfer assay reactions to filter plate and apply vacuum to empty.
13. Add 200 ul wash buffer and apply vacuum to empty. Repeat one time.
14. Add 200 ul illumination buffer and apply vacuum to empty. Repeat one time.
15. Add 30 ul illumination buffer and illuminate for 20 min.
16. Transfer 10 ul of each reaction to CE assay plate for analysis using an ABI3100 CE instrument with a 22 cm capillary (injection conditions: 5 kV, 75 sec, 30° C.; run conditions: 425 sec, 30° C.).

Lysis buffer composition and data analysis were identical to Example 4.

Figure 13A:
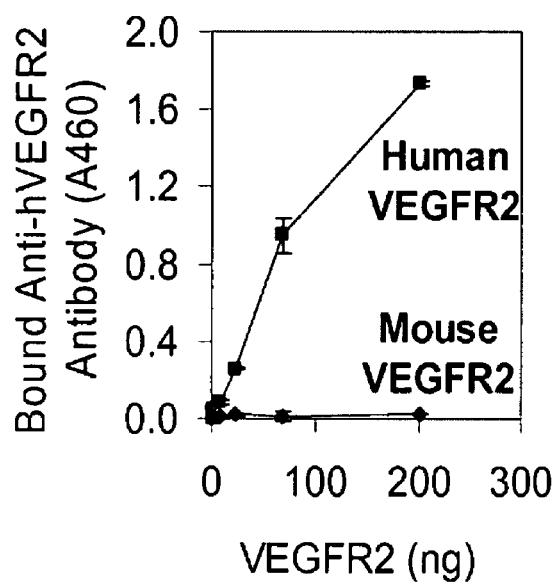
FIG. 13A shows specificity of the cleaving probe to human VEGFR2.
Figure 13B:
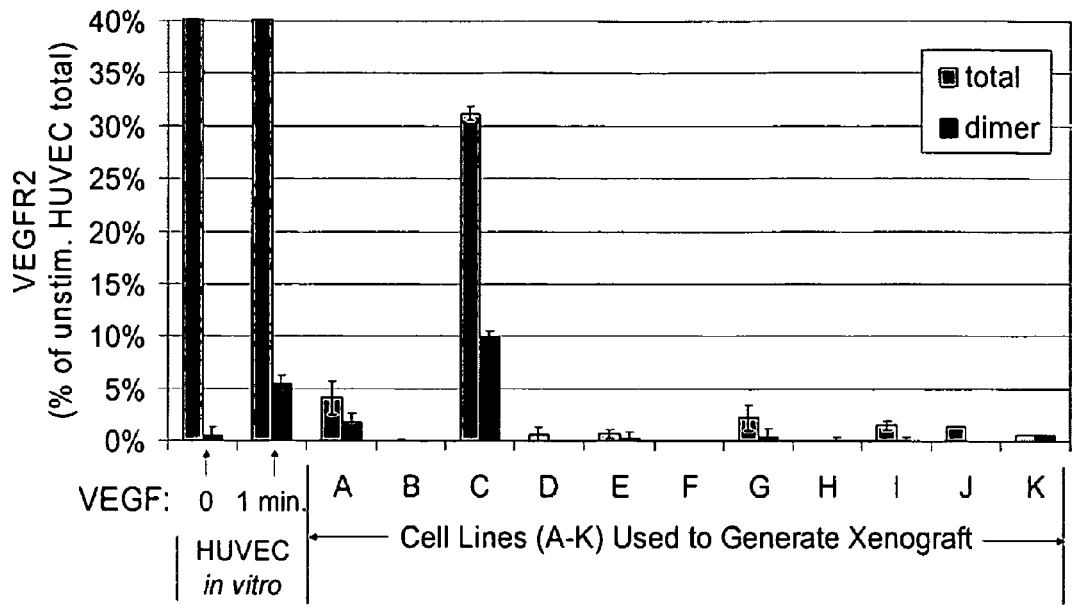
FIG. 13B shows results of xenograph screening for VEGFR2-VEGFR2 homodimers.

Various xenograft tissues were screened for total VEGFR2-VEGFR2 homodimers. Results of the xenograft screening are shown in FIG. 13B. Cell lines used to make the xenografts labeled A-K refer to cell lines DU145, H522, H441, BT474, CALU-3, A549, MDA-MB-231, A431, H460, OVCAR-3 and HCT116, respectively. The levels of VEGFR2 expression and dimerization varied greatly over the cell lines tested, with H441 giving the highest signals.

These results demonstrate that VEGFR2 dimers can be detected in samples obtained from tissues. In addition, these results indicate that this type of assay can be used in identifying cell lines for xenograph models that are useful in testing anti-angiogenic drug susceptibility. By FIG. 13B, cell line H441 can, for example, be useful in this regard. Further, this type of analysis can be useful in screening representative cell lines of various cancer types to identify classes of cancers that are particular susceptible to anti-angiogenic therapy. Such assays can also be used as part of diagnostics for assessing or predicting patient responsiveness to anti-angiogenic therapy.

Example 12

Analysis of Lung Cancer Tissue Lysates for Total VEGFR2 Receptor and Homodimerization In this example, total VEGFR2 and VEGFR2 homodimerization was measured in normal and cancerous lung tissue. Preparation of tissue lysates was identical to the preparation procedure of Example 11. The assay methods and analysis were also identical except that the HUVEC control cells were stimulated for 2 minutes.

Figure 14:
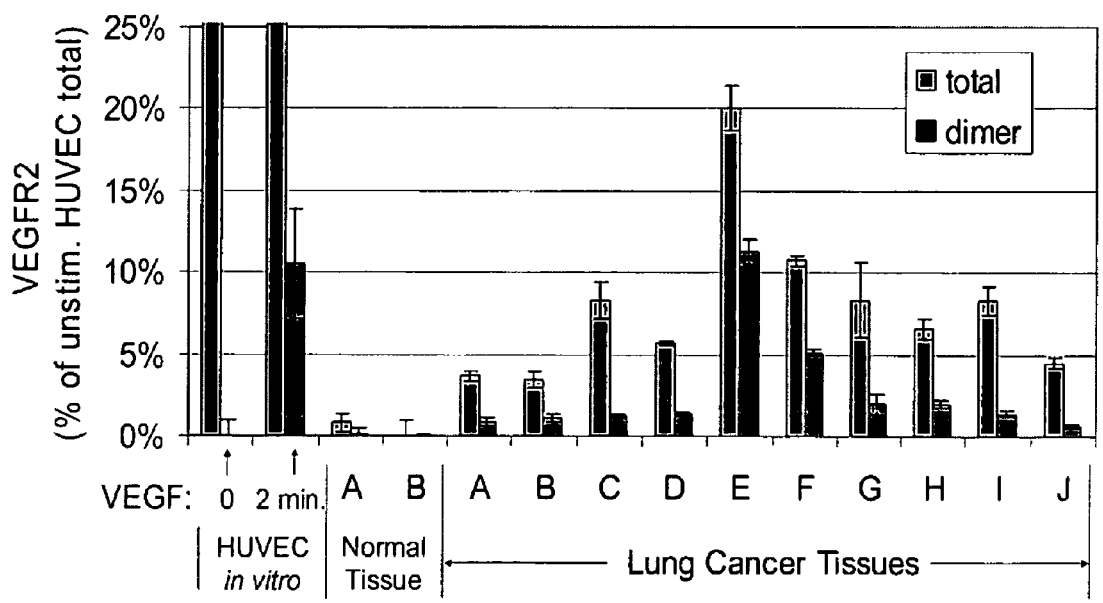
FIG. 14 shows measurement of VEGFR2-VEGFR2 homodimers in various lung cancer tissue and normal tissue samples.

As shown in FIG. 14, lung cancer tissues were found to have a wide variety of total VEGFR2, homodimer levels and ratios of homodimer to total receptor, while the normal tissue samples tested showed low levels of VEGFR2 expression and dimerization.

These results demonstrate that VEGFR2 dimers can be detected in samples obtained from human tumor tissues. Further, this assay illustrates the measurement of a marker that can be indicative of anti-angiogenic drug susceptibility. Assay employing this marker and others associated with the angiogenic state can be utilized in predicting clinical outcomes for a variety of anti-angiogenic therapies. This type of assay may also be used as a surrogate marker for response to anti-angiogenic and other anti-cancer therapy.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting activation of endothelial cells in a test sample, comprising:
   measuring the level of a protein complex that is formed between a first cellular component and a second cellular component independently selected from the group consisting of VEGF and PLGF that are cellular components in an angiogenesis signaling pathway present in the endothelial cells comprising mixing:
   (i) the test sample;
   (ii) a cleaving probe, which is capable of binding the first cellular component and has a cleavage-inducing moiety; and
   (iii) one or more binding compounds, wherein each of the binding compounds is capable of binding the first or the second cellular component and wherein each of the one or more binding compounds has one or more molecular tags each attached thereto by a cleavable linkage; wherein cleavage of the cleavable linkage(s) within effective proximity of the cleaving-inducing moiety of the cleaving probe releases the molecular tag(s), wherein detecting the released molecular tag(s) provides a measurement of the protein complex; and
   wherein a difference in the level of the protein complex relative to the level of the protein complex in a reference sample detects activation of endothelial cells in the test sample.

2. The method of claim 1, wherein the test sample contains circulating endothelial cells or circulating endothelial cell progenitors.

3. The method of claim 2, further comprising isolating circulating endothelial cells or circulating endothelial cell progenitors.

4. The method of claim 3, wherein circulating endothelial cells or circulating endothelial cell progenitors are isolated by immunomagnetic isolation.

5. The method of claim 1, wherein the test sample contains tumor endothelium.

6. The method of claim 1, wherein the test sample is a blood sample.

7. The method of claim 1, wherein the test sample is a fixed tissue sample.

8. The method of claim 1, wherein the molecular tag(s) attached to different binding compounds each have a different separation characteristic.

9. The method of claim 8, further comprising separating the released molecular tag(s).

10. The method of claim 1, wherein said step of mixing includes generating an active species by said cleavage-inducing moiety, wherein the active species cleaves said cleavable linkages within said effective proximity.

11. The method of claim 1, wherein the test sample is obtained from an individual who is suspected of having a disease associated with undesirable angiogenesis, and wherein detecting activation of endothelial cells in the test sample indicates that the individual has the disease.

12. A method for detecting activation of endothelial cells in a test sample, comprising:
   measuring in a test sample the levels of two or more different cellular components that participate in one or more angiogenesis signaling pathways and are selected from the group consisting of VEGF and PLGF wherein the measuring step includes:
   mixing (i) the test sample;
   (ii) a cleaving probe, which is capable of binding one of the two or more cellular components and has a cleavage-inducing moiety; and
   (iii) one or more binding compounds, wherein each of the two or more cellular components is bound by at least one member of the one or more molecular tags each attached thereto by a cleavable linkage; wherein cleavage of the cleavable linkage(s) within effective proximity of the cleaving-inducing moiety of the cleaving probe releases the molecular tag(s), wherein detecting the released molecular tag(s) provides a measurement of the levels of two or more different cellular components in the endothelial cells; and
   wherein a difference in the levels of the two or more different cellular components relative to reference levels of the two or more different cellular components indicates activation of endothelial cells in a test sample.

13. The method of claim 12, wherein the test sample contains circulating endothelial cells or circulating endothelial cell progenitors.

14. The method of claim 12, wherein the test sample contains tumor endothelium.

15. The method of claim 12, wherein the test sample is a blood sample.

16. The method of claim 12, wherein the test sample is a fixed tissue sample.

17. The method of claim 12, wherein the molecular tag(s) attached to different binding compounds each have a different separation characteristic.

18. The method of claim 17, further comprising separating the released molecular tag(s).

19. The method of claim 12, wherein said step of mixing includes generating an active species by said cleavage-inducing moiety, wherein the active species cleaves said cleavable linkages within said effective proximity.

* * * * *